(12) United States Patent
Cruz et al.

(10) Patent No.: US 7,947,281 B2
(45) Date of Patent: May 24, 2011

(54) CHIMERIC PROTEINS THAT INDUCE EFFECTS DIRECTED AGAINST VIRUSES

(75) Inventors: Lisset Hermida Cruz, Havana (CU); Rayner Rodriguez Diaz, Havana (CU); Laura Lazo Vazquez, Havana (CU); Aida Zulueta Morales, Havana (CU); Carlos Lopez Abarrategui, Havana (CU); Iris Valdes Prado, Havana (CU); Richardo de la C. Silva Rodriguez, Havana (CU); Glay Chinea Santiago, Havana (CU); Gerardo Enrique Guillen Nieto, Havana (CU); Maria Guadalupe Guzman Tirado, Havana (CU); Beatriz de la Caridad Sierra Vazquez, Havana (CU); Raul Rafael Espinosa Perez, Havana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 196 days.

(21) Appl. No.: 12/483,607

(22) Filed: Jun. 12, 2009

(65) Prior Publication Data

US 2009/0274718 A1 Nov. 5, 2009

Related U.S. Application Data

(62) Division of application No. 11/705,696, filed on Feb. 13, 2007, now Pat. No. 7,566,457, which is a division of application No. 10/484,114, filed as application No. PCT/CU02/00006 on Jul. 12, 2002, now Pat. No. 7,279,164.

(30) Foreign Application Priority Data

Jul. 16, 2001 (CU) .................................... 20010172

(51) Int. Cl.
*A61K 39/12* (2006.01)
*C07K 19/00* (2006.01)
*C12Q 1/70* (2006.01)

(52) U.S. Cl. ............... 424/186.1; 424/192.1; 424/218.1; 435/5; 530/350

(58) Field of Classification Search ........................ None
See application file for complete search history.

(56) References Cited

U.S. PATENT DOCUMENTS

| 7,279,164 B2 | 10/2007 | Hermida Cruz et al. |
| 2004/0259224 A1 | 12/2004 | Guirakhoo |

FOREIGN PATENT DOCUMENTS

| EP | 0474313 A2 | 3/1992 |
| EP | 1418180 A2 | 5/2004 |
| EP | 1454988 A1 | 9/2004 |
| WO | WO9306214 A1 | 4/1993 |
| WO | WO 96/37221 A1 | 11/1996 |
| WO | WO 97/26359 A1 | 7/1997 |
| WO | WO9743310 A1 | 11/1997 |
| WO | WO9823754 A1 | 6/1998 |
| WO | WO 9831814 A1 | 7/1998 |
| WO | WO9907733 A2 | 2/1999 |
| WO | WO9918216 A2 | 4/1999 |
| WO | WO 00/66791 A1 | 11/2000 |
| WO | WO2004052293 A2 | 6/2004 |
| WO | WO2005002501 A2 | 1/2005 |
| WO | WO2006078657 A2 | 7/2006 |
| WO | WO2006136697 A2 | 12/2006 |
| WO | WO2007124698 A2 | 11/2007 |

OTHER PUBLICATIONS

Blok, J., et al., "Variation of the Nucleotide and Encoded Amino Acid Sequences of the Envelope Gene from Eight Dengue-2 Viruses", Archives of Virology 1989, 105(1-2):39-53.

Lanciotti, Robert S., et al., "Molecular evolution and epidemiology of dengue-3 viruses", Journal of General Virology 1994, 75(1):65-75.

Lanciotti, Robert S., et al., "Molecular evolution and phylogeny of dengue-4 viruses", Journal of General Virology 1997, 78(9):2279-2286.

Silva, Ricardo, et al., "Characterisation of the 1pdA gene from *Neisseria meningitidis* by polymerase chain reaction, restriction fragment length polymorphism and sequencing", FEMS Microbiology Letters May 1999, 174 (1):191-199.

Tettelin, Herve, et al., "Complete Genome Sequence of *Neisseria meningitidis* Serogroup B Strain MC58", Science 2000, 287(5459):1809-1815.

Wang, Eryu, et al., "Evolutionary Relationships of Endemic/Epidemic and Sylvatic Dengue Viruses", Journal of Virology 2000, 74(7):3227-3234.

Chaturvedi et al., "Dengue Vaccines: Problems and Prospects," Indian J. Med. Res. vol. 121, May 2005, pp. 639-652.

Perez et al., "Safety and Preliminary Immunogenicity of the Recombinant Outer Membrane Protein P64K of *Neiseria meningitis* in Human Volunteers," Biotechnol. Appl. Biochem, 34, 121-125 (2001).

Pugachev et al., "New Developments in Flavivirus Vaccines with Special Attention to Yellow Fever," Curr Opin Infect Dis 18:387-394 (2005).

(Continued)

*Primary Examiner* — Mary E Mosher
(74) *Attorney, Agent, or Firm* — Hoffmann & Baron, LLP

(57) ABSTRACT

The present invention is related to the obtaining of chimeric chains coding for proteins capable of inducing, in the recipient, a serotype-specific and protective humoral immune response against the infection by the Dengue virus, thus eliminating the effects of the serotype-nonespecific viral immunoenhancement that causes hemorrhagies and clinical complications described for this kind of pathology. These chimeric chains of nucleic acids are composed by the specific combination of fragments belonging to the gene of a mutated protein from *Neisseria meningitidis* with dehydrogenase activity and fragments that codify for a region of the envelope (E) protein from the Dengue virus which, when inserted to an expression vector, give rise to chimeric proteins with particular properties. The resultant chimeric molecules from this invention are applicable to the pharmaceutical industry for the obtaining of vaccine preparations and diagnostic means of high serotype-specificity to be used in humans.

4 Claims, 13 Drawing Sheets

OTHER PUBLICATIONS

Figure 1:
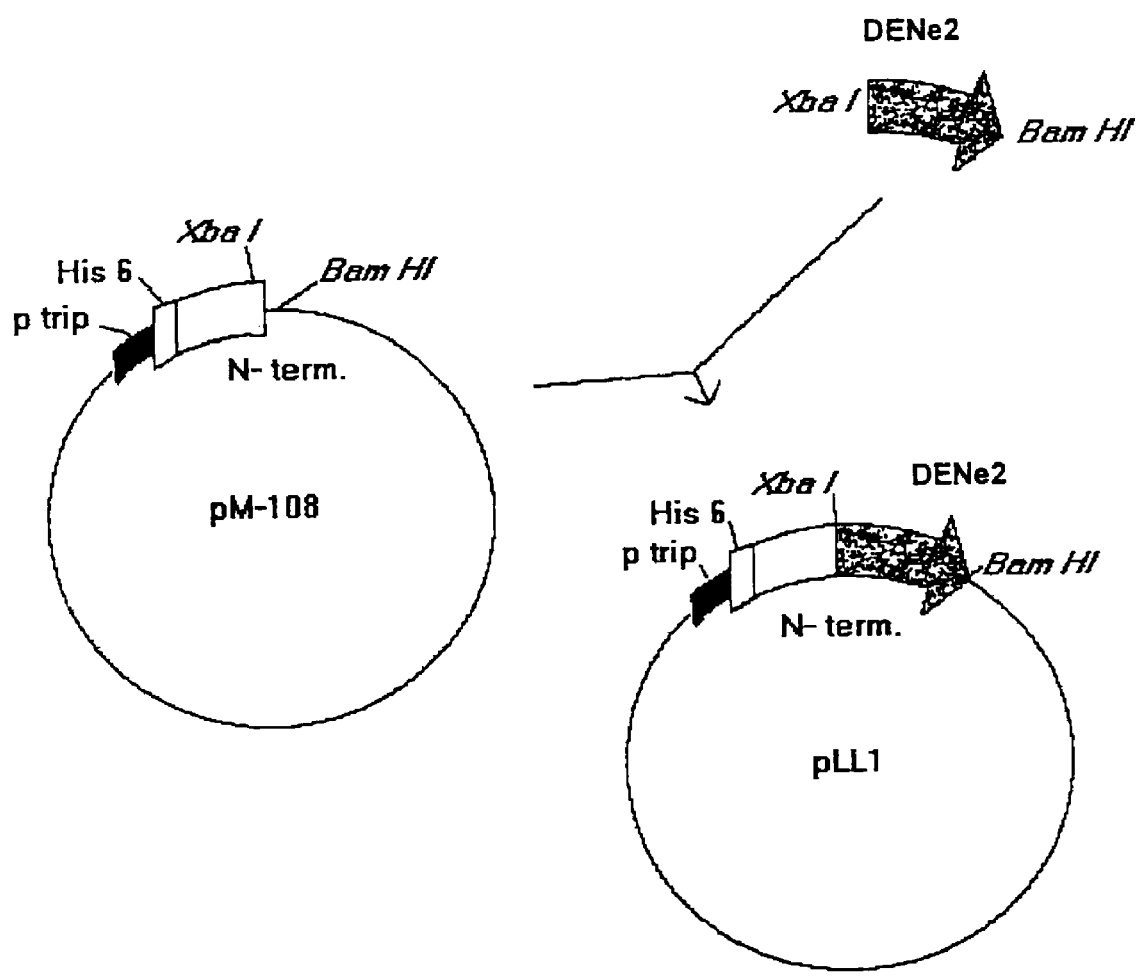

Silva et al., "Characterization of the IpdA Gene from *Neisseria meningitidis* by Polymerase Chain Reaction, Restriction Fragment Length Polymorphism and Sequencing," FEMS Microbiology Letters 174 (1999) 191-199.

Srivastava et al., "Mice Immunized with a Dengue Type 2 Virus E and NS1 Fusion Protein Made in *Escherichia coli* are Protected Against Lethal Dengue Virus Infection," Vaccine vol. 13, No. 13 (1995).

Database UniProt (online) Subname: Full=Polyprotein; XP002492705 retrieved from EBI accession No. UNIPROT: Q2QFY7 Database accession No. Q2QFY7 the whole document (Jan. 24, 2006).

Shiryaev Sergey A et al., "Cleavage Targets and the D-Arginine-Based Inhibitors of the West Nile Virus NS3 Processing Proteinase", Biochemical Journal, vol. 393, No. Part 2, 503-511 (2006).

Portal-Nunez S. et al., "Peptide Inhibitors of Hepatitis C Virus NS3 Protease" Antiviral Chemistry & Chemotherapy, Blackwell Scientific Publ. London, GB, vol. 14, No. 5, 225-233 (2003).

Deshayes S. et al., "Cell-Penetrating Peptides: Tools for Intracellular Delivery of Therapeutics", CMLS Cellular and Molecular Live Sciences, Birkhauser-Verlag, BA, vol. 62, No. 16, 1839-1849 (2005).

Murray, et al., "Processing of the Dengue Virus Type 2 Proteins prM and C-prM", Journal of General Virology, 74, 175-182 (1993).

Goncalvez et al., "Epitope Determinants of a Chimpanzee Fab Antibody that Efficiently Cross-Neutralizes Dengue Type 1 and Type 2 Viruses Map to Inside and in Close Proximity to Fusion Loop of the Dengue Type 2 Virus Envelope Glycoprotein", Journal of Virology, 78(23):12919-12928(2004).

Mason et al., "The Antigenic Structure of Dengue Type I Virus Envelope with NS1 Proteins Expressed in *Escherichia coli*", Journal of General Virology, 71, 2107-2114(1990).

Mota et al., "Induction of Protective Antibodies Against Dengue Virus by Tetravalent DNA Immunization of Mice with Domain III of the Envelope Protein", Vaccine 23, 3469-3476(2005).

Database EBI (Online) Envelope Glycoprotein (Fragment) Shu L. and Zuo, L. "No Title" XP002430600 Retrieved from UNIPROT/TREMBL accession No. Q7TLC5, Database accession No. Q7TLC5-Abstract, (2008).

Thullier et al., "A recombinant Fab Neutralizes Dengue Virus in Vitro", Journal of Biotechnology, Elsevier Science Publishers, vol. 69, No. 2-3, pps. 183-190 (1999) Abstract.

Monath, T. "Dengue and Yellow Fever—Challenges for the Development and Uses of Vaccines", N. Engl J. Med 357:22 2222-2225 (2007).

Mustafa et al., "Dengue Vaccine The Current Status", MJAFI, vol. 64, No. 2, 161-164 (2008).

Shresta, et al., "Murine Model for Denjue Virus-Induced Lethal Disease with Increased Vascular Permeability", Journal of Virology, 80:20, 10208-10217 (2006).

Irie et al., "Sequence analysis of cloned dengue virus type 2 genome (New Guinea-C strain)", Gene 75: 197-211 (1989).

Gruenberg et al., "Partial Nucleotide Sequence and Deduced Amino Sequence of the Structural Proteins of Dengue Virus Type 2, New Guinea C and PUO-218 Strains", J. gen Virol. 69, 1391-1398 (1988).

Zhao et al., "Cloning Full-Length Dengue Type 4 Viral DNA Sequences: Analysis of Genes Coding for Structural Proteins", Virol. 155:77-88 (1986).

Gaines et al., "Pathogen-Derived Resistance to Dengue Type 2 Virus in Mosquito Cells by Expression of the Premembrane Coding Region of the Viral Genome", Journal of Virology, p. 2132-2137 (1996).

Kaufman et al., "Monoclonal Antibodies for Dengue Virus PRM Glycoprotein Protect Mice Against Lethal Dengue Infection", Am. J. Trop. Med. Hyg., 41(5), pp. 576-580 (89-157) 1989.

Bray et al., "Dengue Virus Premembrane and Membrane Proteins Elicit a Protection Immune Response", Virology, 185, 505-508 (1991).

Randolph et al., "Acidotropic Amines Inhibit Proteolytic Processing of Flavivirus prM Protein", Virology 174, 450-458 (1990).

SEQUENCE LISTING

```
<160> NUMBER OF SEQ ID NOS: 54

<210> SEQ ID NO 1
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Xba-I primer for the
      amplification of DENe-2 fragment

<400> SEQUENCE: 1
cttctagaca ggctgcgcat ggaca                                          25

<210> SEQ ID NO 2
<211> LENGTH: 29
<212> TYPE: DNA
<213> ORGANISM: Escherichia coli
<220> FEATURE:
<221> NAME/KEY: primer_bind
<222> LOCATION: (1)..(29)
<223> OTHER INFORMATION: Sequence of the Bam-HI primer for the
      amplification of DENe-2 fragment

<400> SEQUENCE: 2
gtggatcctt accctcccag gcttccaaa                                      29

<210> SEQ ID NO 3
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-2 fragment

<400> SEQUENCE: 3
atgaattcac gcctcccaga gatcc                                          25
```

```
<210> SEQ ID NO 4
<211> LENGTH: 21
<212> TYPE: DNA
<213> ORGANISM: Escherichia coli
<220> FEATURE:
<221> NAME/KEY: primer_bind
<222> LOCATION: (1)..(21)
<223> OTHER INFORMATION: Sequence of the Bam-HI primer for the
      amplification of DENe-2 fragment

<400> SEQUENCE: 4
cttggatcca ggctgagaat g                                         21

<210> SEQ ID NO 5
<211> LENGTH: 31
<212> TYPE: DNA
<213> ORGANISM: Escherichia coli
<220> FEATURE:
<221> NAME/KEY: primer_bind
<222> LOCATION: (1)..(31)
<223> OTHER INFORMATION: Sequence of the Bam-HI primer for the
      amplification of DENe-2 fragment

<400> SEQUENCE: 5
gaggatcctt aaccacccag agacccaaaa t                              31

<210> SEQ ID NO 6
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Xba-I primer for the
      amplification of DENe-1 fragment

<400> SEQUENCE: 6
cttctagaca ggctcaaaat ggata                                     25

<210> SEQ ID NO 7
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-1 fragment

<400> SEQUENCE: 7
gaggatcctt acccgccaat agaaccga                                  28

<210> SEQ ID NO 8
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-1 fragment

<400> SEQUENCE: 8
acgaattcac ccctcctata gatcc                                     25

<210> SEQ ID NO 9
<211> LENGTH: 24
<212> TYPE: DNA
<213> ORGANISM: Escherichia coli
<220> FEATURE:
```

```
<221> NAME/KEY: primer_bind
<222> LOCATION: (1)..(24)
<223> OTHER INFORMATION: Sequence of the Bam-HI primer for the
      amplification of DENe-1 fragment

<400> SEQUENCE: 9
acaccttgga tccagactaa aaat                                                24

<210> SEQ ID NO 10
<211> LENGTH: 26
<212> TYPE: DNA
<213> ORGANISM: Escherichia coli
<220> FEATURE:
<221> NAME/KEY: primer_bind
<222> LOCATION: (1)..(26)
<223> OTHER INFORMATION: Sequence of the Bam-HI primer for the
      amplification of DENe-1 fragment

<400> SEQUENCE: 10
ccggatccgt gaattaccca cctata                                              26

<210> SEQ ID NO 11
<211> LENGTH: 29
<212> TYPE: DNA
<213> ORGANISM: Escherichia coli
<220> FEATURE:
<221> NAME/KEY: primer_bind
<222> LOCATION: (1)..(29)
<223> OTHER INFORMATION: Sequence of the Xba-I primer for the
      amplification of DENe-3 fragment

<400> SEQUENCE: 11 tttctag

```
<400> SEQUENCE: 14
acttaggatc cagactcaag atg                                              23

<210> SEQ ID NO 15
<211> LENGTH: 26
<212> TYPE: DNA
<213> ORGANISM: Escherichia coli
<220> FEATURE:
<221> NAME/KEY: primer_bind
<222> LOCATION: (1)..(26)
<223> OTHER INFORMATION: Sequence of the Bam-HI primer for the
      amplification of DENe-3 fragment

<400> SEQUENCE: 15
gaggatcctt aaccacccac tgaacc                                           26

<210> SEQ ID NO 16
<211> LENGTH: 30
<212> TYPE: DNA
<213> ORGANISM: Escherichia coli
<220> FEATURE:
<221> NAME/KEY: primer_bind
<222> LOCATION: (1)..(30)
<223> OTHER INFORMATION: Sequence of the Xba-I primer for the
      amplification of DENe-4 fragment

<400> SEQUENCE: 16
cttctagaca aagtgcgtat ggagaaattg                                       30

<210> SEQ ID NO 17
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-4 fragment

<400> SEQUENCE: 17
gaggatcctt aaccaccaac agaaccaa                                         28

<210> SEQ ID NO 18
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-4 fragment

<400> SEQUENCE: 18
atgaattcag tccaccaacg ctacc                                            25

<210> SEQ ID NO 19
<211> LENGTH: 27
<212> TYPE: DNA
<213> ORGANISM: Escherichia coli
<220> FEATURE:
<221> NAME/KEY: primer_bind
<222> LOCATION: (1)..(27)
<223> OTHER INFORMATION: Sequence of the Bam-HI primer for the
      amplification of DENe-4 fragment

<400> SEQUENCE: 19
ggccatctag gatccaaagt gcgtatg                                          27
```

```
<210> SEQ ID NO 20
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-4 fragment

<400> SEQUENCE: 20
gaggatcctt agccaccaac cgaaccaa                                            28

<210> SEQ ID NO 21
<211> LENGTH: 26
<212> TYPE: DNA
<213> ORGANISM: Escherichia coli
<220> FEATURE -continued

```
<212> TYPE: DNA
<213> ORGANISM: Escherichia coli
<220> FEATURE:
<221> NAME/KEY: gene
<222> LOCATION: (1)..(603)
<223> OTHER INFORMATION: Nucleotidic sequence coding for the quimeric
      protein in the plasmid pLL1

<400> SEQUENCE: 24
atgggccacc accaccacca ccacgccatg gtagataaaa gaatggcttt agttgaattg      60
aaagtgcccg acattggcgg aacagaaaat gtagatatta tcgcggttga agtaaacgtg     120
ggcgacacta ttgctgtgga cgatacccctg attactttgg atctagacag gctgcgcatg    180
gacaaactac agctcaaagg aatgtcatac tctatgtgta caggaaagtt taaaattgtg     240
aaggaaatag cagaaacaca acatggaaca atagttatca gagtacaata tgaaggggac     300
ggctctccat gtaagatccc ttttgagata atggatttgg aaaaaagaca cgtcttaggt     360
cgcctgatta cagttaaccc gatcgtaaca gaaaaagata gcccagtcaa catagaagca     420
gaacctccat tcggagacag ctacatcatc ataggagtag agccgggaca attgaaactc     480
aactggttta agaaaggaag ttccatcggc caaatgtttg agacaacaat gagaggagcg     540
aagagaatgg ccatttttagg tgacacagcc tgggattttg gaagcctggg agggtaagga    600
tcc                                                                   603

<210> SEQ ID NO 25
<211> LENGTH: 195
<212> TYPE: PRT
<213> ORGANISM: Escherichia coli
<220> FEATURE:
<221> NAME/KEY: CHAIN
<222> LOCATION: (1)..(195)
<223> OTHER INFORMATION: Aminoacidic sequence of the PLL1 protein

<400> SEQUENCE: 25

His His His His His His Met Val Asp Lys Arg Met Ala Leu Val Glu
 1               5                  10                  15

Leu Lys Val Pro Asp Ile Gly Gly His Glu Asn Val Asp Ile Ile Ala
                20                  25                  30

Val Glu Val Asn Val Gly Asp Thr Ile Ala Val Asp Asp Thr Leu Ile
         35                  40                  45

Thr Leu Asp Leu Asp Arg Leu Arg Met Asp Lys Leu Gln Leu Lys Gly
     50                  55                  60

Met Ser Tyr Ser Met Cys Thr Gly Lys Phe Lys Ile Val Lys Glu Ile
 65                  70                  75                  80

Ala Glu Thr Gln His Gly Thr Ile Val Ile Arg Val Gln Tyr Glu Gly
                 85                  90                  95

Asp Gly Ser Pro Cys Lys Ile Pro Phe Glu Ile Met Asp Leu Glu Lys
            100                 105                 110

Arg His Val Leu Gly Arg Leu Ile Thr Val Asn Pro Ile Val Thr Glu
        115                 120                 125

Lys Asp Ser Pro Val Asn Ile Glu Ala Glu Pro Pro Phe Gly Asp Ser
    130                 135                 140

Tyr Ile Ile Ile Gly Val Glu Pro Gly Gln Leu Lys Leu Asn Trp Phe
145                 150                 155                 160

Lys Lys Gly Ser Ser Ile Gly Gln Met Phe Glu Thr Thr Met Arg Gly
                165                 170                 175

Ala Lys Arg Met Ala Ile Leu Gly Asp Thr Ala Trp Asp Phe Gly Ser
            180                 185                 190
```

Leu Gly Gly
    195

<210> SEQ ID NO 26
<211> LENGTH: 1851
<212> TYPE: DNA
<213> ORGANISM: Escherichia coli
<220> FEATURE:
<221> NAME/KEY: gene
<222> LOCATION: (1)..(1851)
<223> OTHER INFORMATION: Nucleotidic sequence of the MDH in the plasmid pM84 His.

<400> SEQUENCE: 26

```
atgggccacc accaccacca ccacgccatg gtagataaaa gaatggcttt agttgaattg      60
aaagtgcccg acattggcgg aacagaaaat gtagatatta tcgcggttga agtaaacgtg     120
ggcgacacta ttgctgtgga cgataccctg attactttgg atctagattt ggatctagaa     180
gaactagtgg atccccgggg ctgcaggaat tcgatgaatt cgatggacgt acctgctgaa     240
gttgcaggcg tagtcaaaga agttaaagtt aaagtcggcg acaaaatctc tgaaggtggt     300
ttgattgtcg tcgttgaagc tgaaggcacg gcagccgctc ctaaagccga agcggctgcc     360
gccccggcgc aagaagcccc taaagctgcc gctcctgctc cgcaagccgc gcaattcggc     420
ggttctgccg atgccgagta cgacgtggtc gtattgggtg gcggtcccgg cggttactcc     480
gctgcatttg ccgctgccga tgaaggcttg aaagtcgcca tcgtcgaacg ttacaaaact     540
ttgggcggtt tttgcctgaa cgtcggctgt atcccttcca aagccttgtt gcacaatgcc     600
gccgttatcg acgaagtgcg ccacttggct gccaacggta tcaaataccc cgagccggaa     660
ctcgacatcg atatgcttcg cgcctacaaa gacggcgtag tttcccgcct cacgggcggt     720
ttggcaggta tggcgaaaag ccgtaaagtg gacgttatcc aaggcgacgg gcaattctta     780
gatccgcacc acttggaagt gtcgctgact gccggcgacg cgtacgaaca ggcagcccct     840
accggcgaga aaaaaatcgt tgccttcaaa aactgtatca ttgcagcagg cagccgcgta     900
accaaactgc ctttcattcc tgaagatccg cgcatcatcg attccagcgg cgcattggct     960
ctgaaagaag taccgggcaa actgctgatt atcggcggcg gcattatcgg cctcgagatg    1020
ggtacggttt acagcacgct gggttcgcgt ttggatgtgg ttgaaatgat ggacggcctg    1080
atgcaaggcg cagaccgcga tttggtaaaa gtatggcaaa aacaaaacga ataccgtttt    1140
gacaacatta tggtcaacac caaaaccgtt gcagttgagc cgaaagaaga cggcgtttac    1200
gttacctttg aaggcgcgaa cgcgcctaaa gagccgcaac gctacgatgc cgtattggtt    1260
gccgccggcc gcgcgcccaa cggcaaactc atcagcgcgg aaaaagcagg cgttgccgta    1320
accgatcgcg gcttcatcga agtggacaaa caaatgcgta ccaatgtgcc gcacatctac    1380
gccatcggcg acatcgtcgg tcagccgatg ttggcgcaca agccgttca cgaaggccac    1440
gttgccgcca aaactgcgcg cggccacaaa gcctacttcg acgcacgcgt gattccgggc    1500
gttgcctaca cttcccccga gtggcgtggg gtgggcgaaa ccgaactgtc cgccaaagcc    1560
tccgccgcca aaatcaccaa agccaacttc ccgtgggcgg cttccggccg tgcgattgcc    1620
aacggttgcg acaagccgtt taccaagctg attttgatg ccgaaaccgg ccgcatcatc    1680
ggcgcggcca ttgtcggtcc gaacggtggc gatatgatcg cgaagtctg ccttgccatc    1740
gaaatgggct gcgacgcggc agacatcggc aaaaccatcc acccgcaccc gggcgaatcc    1800
atcggtatgg cggcggaagt ggcattgggt acttgtaccg acaaaaaaaa a            1851
```

<210> SEQ ID NO 27

```
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence of the quimeric protein
      in the plasmid pLL2.

<400> SEQUENCE: 27
```

| | | | | | |
|---|---|---|---|---|---|
| atgggccacc | accaccacca | ccacgccatg | gtagataaaa | gaatggcttt | agttgaattg | 60 |
| aaagtgcccg | acattggcgg | aacagaaaat | gtagatatta | tcgcggttga | agtaaacgtg | 120 |
| ggcgacacta | ttgctgtgga | cgataccctg | attactttgg | atctagattt | ggatctagac | 180 |
| aggctgcgca | tggacaaact | acagctcaaa | ggaatgtcat | actctatgtg | tacaggaaag | 240 |
| tttaaaattg | tgaaggaaat | agcagaaaca | caacatggaa | caatagttat | cagagtacaa | 300 |
| tatgaagggg | acggctctcc | atgtaagatc | ccttttgaga | taatggattt | ggaaaaaaga | 360 |
| cacgtcttag | gtcgcctgat | tacagttaac | ccgatcgtaa | cagaaaaaga | tagcccagtc | 420 |
| aacatagaag | cagaacctcc | attcggagac | agctacatca | tcataggagt | agagccggga | 480 |
| caattgaaac | tcaactggtt | taagaaagga | agttccatcg | ccaaatgtt | tgagacaaca | 540 |
| atgagaggag | cgaagagaat | ggccatttta | ggtgacacag | cctgggattt | tggatctctg | 600 |
| ggaggcgtga | attcgatgaa | ttcgatggac | gtacctgctg | aagttgcagg | cgtagtcaaa | 660 |
| gaagttaaag | ttaaagtcgg | cgacaaaatc | tctgaaggtg | gtttgattgt | cgtcgttgaa | 720 |
| gctgaaggca | cggcagccgc | tcctaaagcc | gaagcggctg | ccgccccggc | gcaagaagcc | 780 |
| cctaaagctg | ccgctcctgc | tccgcaagcc | gcgcaattcg | gcggttctgc | cgatgccgag | 840 |
| tacgacgtgg | tcgtattggg | tggcggtccc | ggcggttact | ccgctgcatt | tgccgctgcc | 900 |
| gatgaaggct | tgaaagtcgc | catcgtcgaa | cgttacaaaa | ctttgggcgg | cgtttgcctg | 960 |
| aacgtcggct | gtatcccttc | caaagccttg | ttgcacaatg | ccgccgttat | cgacgaagtg | 1020 |
| cgccacttgg | ctgccaacgg | tatcaaatac | cccgagccgg | aactcgacat | cgatatgctt | 1080 |
| cgcgcctaca | agacggcgt | agtttcccgc | ctcacgggcg | gtttggcagg | tatggcgaaa | 1140 |
| agccgtaaag | tggacgttat | ccaaggcgac | gggcaattct | tagatccgca | ccacttggaa | 1200 |
| gtgtcgctga | ctgccggcga | cgcgtacgaa | caggcagccc | ctaccggcga | gaaaaaaatc | 1260 |
| gttgccttca | aaactgtat | cattgcagca | ggcagccgcg | taaccaaact | gccttttcatt | 1320 |
| cctgaagatc | cgcgcatcat | cgattccagc | ggcgcattgg | ctctgaaaga | agtaccgggc | 1380 |
| aaactgctga | ttatcggcgg | cggcattatc | ggcctcgaga | tgggtacggt | ttacagcacg | 1440 |
| ctgggttcgc | gtttggatgt | ggttgaaatg | atggacggcc | tgatgcaagg | cgcagaccgc | 1500 |
| gatttggtaa | aagtatggca | aaaacaaaac | gaataccgtt | ttgacaacat | tatggtcaac | 1560 |
| accaaaaccg | ttgcagttga | gccgaaagaa | gacggcgttt | acgttacctt | tgaaggcgcg | 1620 |
| aacgcgccta | agagccgca | acgctacgat | gccgtattgg | ttgccgccgg | ccgcgcgccc | 1680 |
| aacggcaaac | tcatcagcgc | ggaaaaagca | ggcgttgccg | taaccgatcg | cggcttcatc | 1740 |
| gaagtggaca | acaaatgcg | taccaatgtg | ccgcacatct | acgccatcgg | cgacatcgtc | 1800 |
| ggtcagccga | tgttggcgca | caagccgtt | cacgaaggcc | acgttgccgc | gaaaactgc | 1860 |
| gccgccacaa | agcctacttt | cgacgcacgc | gtgattccgg | cgttgccta | cacttccccc | 1920 |
| gaagtggcgt | gggtgggcga | aaccgaactg | tccgccaaag | cctccggccg | caaaatcacc | 1980 |
| aaagccaact | tcccgtgggc | ggcttccggc | cgtgcgattg | ccaacggttg | cgacaagccg | 2040 |
| tttaccaagc | tgatttttga | tgccgaaacc | ggccgcatca | tcggcggcgg | cattgtcggt | 2100 |

```
ccgaacggtg gcgatatgat cggcgaagtc tgccttgcca tcgaaatggg ctgcgacgcg    2160
gcagacatcg gcaaaaccat ccacccgcac ccgggcgaat ccatcggtat ggcggcggaa    2220
gtggcattgg gtacttgtac cgacaaaaaa aaa                                 2253
```

<210> SEQ ID NO 28
<211> LENGTH: 748
<212> TYPE: PRT
<213> ORGANISM: Escherichia coli
<220> FEATURE:
<221> NAME/KEY: CHAIN
<222> LOCATION: (1)..(748)
<223> OTHER INFORMATION: Aminoacidic sequence of PLL2.

<400> SEQUENCE: 28

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
                 20                  25                  30

Val Glu Val Asn Val Gly Asp Thr Ile Ala Val Asp Asp Thr Leu Ile
             35                  40                  45

Thr Leu Asp Leu Asp Arg Leu Arg Met Asp Lys Gln Leu Lys Gly
         50                  55                  60

Met Ser Tyr Ser Met Cys Thr Gly Lys Phe Lys Ile Val Lys Glu Ile
 65                  70                  75                  80

Ala Glu Thr Gln His Gly Thr Ile Val Ile Arg Val Gln Tyr Glu Gly
                 85                  90                  95

Asp Gly Ser Pro Cys Lys Ile Pro Phe Glu Ile Met Asp Leu Glu Lys
            100                 105                 110

Arg His Val Leu Gly Arg Leu Ile Thr Val Asn Pro Ile Val Thr Glu
        115                 120                 125

Lys Asp Ser Pro Val Asn Ile Glu Ala Glu Pro Pro Phe Gly Asp Ser
    130                 135                 140

Tyr Ile Ile Ile Gly Val Glu Pro Gly Gln Leu Lys Leu Asn Trp Phe
145                 150                 155                 160

Lys Lys Gly Ser Ser Ile Gly Gln Met Phe Glu Thr Thr Met Arg Gly
                165                 170                 175

Ala Lys Arg Met Ala Ile Leu Gly Asp Thr Ala Trp Asp Phe Gly Ser
            180                 185                 190

Leu Gly Gly Val Asn Ser Met Asn Ser Met Asp Val Pro Ala Glu Val
        195                 200                 205

Ala Gly Val Val Lys Glu Val Lys Val Lys Val Gly Asp Lys Ile Ser
    210                 215                 220

Glu Gly Gly Leu Ile Val Val Val Glu Ala Gly Thr Ala Ala Ala
225                 230                 235                 240

Pro Lys Ala Glu Ala Ala Ala Pro Ala Gln Glu Ala Pro Lys Ala
                245                 250                 255

Ala Ala Pro Ala Pro Gln Ala Ala Gln Phe Gly Gly Ser Ala Asp Ala
            260                 265                 270

Glu Tyr Asp Val Val Val Leu Gly Gly Gly Pro Gly Gly Tyr Ser Ala
        275                 280                 285

Ala Phe Ala Ala Ala Asp Glu Gly Leu Lys Val Ala Ile Val Glu Arg
    290                 295                 300

Tyr Lys Thr Leu Gly Gly Val Cys Leu Asn Val Gly Cys Ile Pro Ser
305                 310                 315                 320

Lys Ala Leu Leu His Asn Ala Ala Val Ile Asp Glu Val Arg His Leu
```

```
                    325                 330                 335
Ala Ala Asn Gly Ile Lys Tyr Pro Glu Pro Glu Leu Asp Ile Asp Met
            340                 345                 350

Leu Arg Ala Tyr Lys Asp Gly Val Val Ser Arg Leu Thr Gly Gly Leu
            355                 360                 365

Ala Gly Met Ala Lys Ser Arg Lys Val Asp Val Ile Gln Gly Asp Gly
            370                 375                 380

Gln Phe Leu Asp Pro His His Leu Glu Val Ser Leu Thr Ala Gly Asp
385                 390                 395                 400

Ala Tyr Glu Gln Ala Ala Pro Thr Gly Glu Lys Lys Ile Val Ala Phe
            405                 410                 415

Lys Asn Cys Ile Ile Ala Ala Gly Ser Arg Val Thr Lys Leu Pro Phe
            420                 425                 430

Ile Pro Glu Asp Pro Arg Ile Ile Asp Ser Ser Gly Ala Leu Ala Leu
            435                 440                 445

Lys Glu Val Pro Gly Lys Leu Leu Ile Ile Gly Gly Gly Ile Ile Gly
            450                 455                 460

Leu Glu Met Gly Thr Val Tyr Ser Thr Leu Gly Ser Arg Leu Asp Val
465                 470                 475                 480

Val Glu Met Met Asp Gly Leu Met Gln Gly Ala Asp Arg Asp Leu Val
            485                 490                 495

Lys Val Trp Gln Lys Gln Asn Glu Tyr Arg Phe Asp Asn Ile Met Val
            500                 505                 510

Asn Thr Lys Thr Val Ala Val Glu Pro Lys Glu Asp Gly Val Tyr Val
            515                 520                 525

Thr Phe Glu Gly Ala Asn Ala Pro Lys Glu Pro Gln Arg Tyr Asp Ala
530                 535                 540

Val Leu Val Ala Ala Gly Arg Ala Pro Asn Gly Lys Leu Ile Ser Ala
545                 550                 555                 560

Glu Lys Ala Gly Val Ala Val Thr Asp Arg Gly Phe Ile Glu Val Asp
            565                 570                 575

Lys Gln Met Arg Thr Asn Val Pro His Ile Tyr Ala Ile Gly Asp Ile
            580                 585                 590

Val Gly Gln Pro Met Leu Ala His Lys Ala Val His Glu Gly His Val
            595                 600                 605

Ala Ala Glu Asn Cys Ala Gly His Lys Ala Tyr Phe Asp Ala Arg Val
            610                 615                 620

Ile Pro Gly Val Ala Tyr Thr Ser Pro Glu Val Ala Trp Val Gly Glu
625                 630                 635                 640

Thr Glu Leu Ser Ala Lys Ala Ser Gly Arg Lys Ile Thr Lys Ala Asn
            645                 650                 655

Phe Pro Trp Ala Ala Ser Gly Arg Ala Ile Ala Asn Gly Cys Asp Lys
            660                 665                 670

Pro Phe Thr Lys Leu Ile Phe Asp Ala Glu Thr Gly Arg Ile Ile Gly
            675                 680                 685

Gly Gly Ile Val Gly Pro Asn Gly Gly Asp Met Ile Gly Glu Val Cys
            690                 695                 700

Leu Ala Ile Glu Met Gly Cys Asp Ala Ala Asp Ile Gly Lys Thr Ile
705                 710                 715                 720

His Pro His Pro Gly Glu Ser Ile Gly Met Ala Ala Glu Val Ala Leu
            725                 730                 735

Gly Thr Cys Thr Asp Leu Pro Pro Gln Lys Lys Lys
            740                 745
```

<210> SEQ ID NO 29
<211> LENGTH: 1821
<212> TYPE: DNA
<213> ORGANISM: Escherichia coli
<220> FEATURE:
<221> NAME/KEY: gene
<222> LOCATION: (1)..(1821)
<223> OTHER INFORMATION: Nucleotidic sequence of the MDH in the plasmid pD4

<400> SEQUENCE: 29

```
atgggccacc accaccacca ccacgccatg gtagataaaa gaatggcttt agttgaattg      60
aaagtgcccg acattggcgg acacgaaaat gtagatatta tcgcggttga agtaaacgtg     120
ggcgacacta ttgctgtgga cgataccctg attactttgg atctagaaat ggacgtacct     180
gctgaagttg caggcgtagt caaagaagtt aaagttaaag tcggcgacaa aatctctgaa     240
ggtggtttga ttgtcgtcgt tgaagctgaa ggcacggcag ccgctcctaa agccgaagcg     300
gctgccgccc cggcgcaaga agcccctaaa gctgccgctc ctgctccgca agccgcgcaa     360
ttcggcggtt ctgccgatgc cgagtacgac gtggtcgtat gggtggcgg tcccggcgt      420
tactccgctg catttgccgc tgccgatgaa ggcttgaaag tcgccatcgt cgaacgttac     480
aaaactttgg cggcgtttg cctgaacgtc ggctgtatcc cttccaaagc cttgttgcac     540
aatgccgccg ttatcgacga agtgcgccac ttggctgcca acggtatcaa ataccccgag     600
ccggaactcg acatcgatat gcttcgcgcc tacaaagacg gcgtagtttc ccgcctcacg     660
ggcggtttgg caggtatggc gaaaagccgt aaagtggacg ttatccaagg cgacgggcaa     720
ttcttagatc cgcaccactt ggaagtgtcg ctgactgccg gcgacgcgta cgaacaggca     780
gccccctaccg gcgagaaaaa aatcgttgcc ttcaaaaact gtatcattgc agcaggcagc     840
cgcgtaacca aactgccttt cattcctgaa gatccgcgca tcatcgattc cagcggcgca     900
ttggctctga agaagtaccg gcaaactg ctgattatcg gcggcggcat tatcggcctc       960
gagatgggta cggtttacag cacgctgggt tcgcgtttgg atgtggttga aatgatggac    1020
ggcctgatgc aaggcgcaga ccgcgatttg gtaaaagtat ggcaaaaaca aaacgaatac    1080
cgttttgaca acattatggt caacaccaaa accgttgcag ttgagccgaa agaagacggc    1140
gtttacgtta cctttgaagg cgcgaacgcg cctaaagagc cgcaacgcta cgatgccgta    1200
ttggttgccg ccggccgcgc gcccaacggc aaactcatca gcgcggaaaa agcaggcgtt    1260
gccgtaaccg atcgcggctt catcgaagtg gacaaacaaa tgcgtaccaa tgtgccgcac    1320
atctacgcca tcggcgacat cgtcggtcag ccgatgttgg cgcacaaagc cgttcacgaa    1380
ggccacgttg ccgccgaaaa ctgcgccggc cacaaagcct acttcgacgc acgcgtgatt    1440
ccgggcgttg cctacacttc cccgaagtg gcgtgggtgg gcgaaaccga actgtccgcc     1500
aaagcctccg gccgcaaaat caccaaagcc aacttcccgt gggcggcttc cggccgtgcg    1560
attgccaacg gttgcgacaa gccgtttacc aagctgattt ttgatgccga aaccggccgc    1620
atcatcggcg cggcattgt cggtccgaac ggtggcgata tgatcggcga agtctgcctt    1680
gccatcgaaa tgggctgcga cgcggcagac atcggcaaaa ccatccaccc gcaccccgacc   1740
ttgggcgaat ccatcggtat ggcggcggaa gtggcattgg gtacttgtac cgacctgcct    1800
ccgcaaaaga aaaaggatc c                                              1821
```

<210> SEQ ID NO 30
<211> LENGTH: 2259
<212> TYPE: DNA
<213> ORGANISM: Escherichia coli
<220> FEATURE:
<221> NAME/KEY: gene
<222> LOCATION: (1)..(2259)
<223> OTHER INFORMATION: Nucleotidic sequence coding for the quimeric
      protein in the plasmid pLL3

<400> SEQUENCE: 30

```
atgggccacc accaccacca ccacgccatg gtagataaaa gaatggcttt agttgaattg      60
aaagtgcccg acattggcgg acacgaaaat gtagatatta tcgcggttga agtaaacgtg     120
ggcgacacta ttgctgtgga cgataccctg attactttgg atctagaaat ggacgtacct     180
gctgaagttg caggcgtagt caaagaagtt aaagttaaag tcggcgacaa aatctctgaa     240
ggtggtttga ttgtcgtcgt tgaagctgaa ggcacggcag ccgctcctaa agccgaagcg     300
gctgccgccc cggcgcaaga agcccctaaa gctgccgctc ctgctccgca agccgcgcaa     360
ttcggcggtt ctgccgatgc cgagtacgac gtggtcgtat gggtggcgg tcccggcggt      420
tactccgctg catttgccgc tgccgatgaa ggcttgaaag tcgccatcgt cgaacgttac     480
aaaactttgg gcggcgtttg cctgaacgtc ggctgtatcc cttccaaagc cttgttgcac     540
aatgccgcct tatcgacga agtgcgccac ttggctgcca acggtatcaa ataccccgag      600
ccggaactcg acatcgatat gcttcgcgcc tacaaagacg gcgtagtttc ccgcctcacg     660
ggcggtttgg caggtatggc gaaaagccgt aaagtggacg ttatccaagg cgacgggcaa     720
ttcttagatc cgcaccactt ggaagtgtcg ctgactgccg gcgacgcgta cgaacaggca     780
gcccctaccg gcgagaaaaa aatcgttgcc ttcaaaaact gtatcattgc agcaggcagc     840
cgcgtaacca aactgccttt cattcctgaa gatccgcgca tcatcgattc cagcggcgca     900
ttggctctga agaagtaccc gggcaaactg ctgattatcg gcggcggcat tatcggcctc     960
gagatgggta cggtttacag cacgctgggt tcgcgtttgg atgtggttga aatgatggac    1020
ggcctgatgc aaggcgcaga ccgcgatttg gtaaagtat ggcaaaaaca aaacgaatac     1080
cgttttgaca cattatggt caacaccaaa accgttgcag ttgagccgaa agaagacggc    1140
gtttacgtta cctttgaagg cgcgaacgcg cctaaagagc cgcaacgcta cgatgccgta    1200
ttggttgccg ccgccgcgc gcccaacggc aaactcatca gcgcgaaaaa agcaggcgtt     1260
gccgtaaccg atcgcggctt catcgaagtg gacaaacaaa tgcgtaccaa tgtgccgcac    1320
atctacgcca tcgcgacat cgtcggtcag ccgatgttgg cgcacaaagc cgttcacgaa     1380
ggccacgttg ccgccgaaaa actgcgccgg cacaaagcct acttcgacgc acgcgtgatt    1440
ccgggcgttg cctacacttc ccccgaagtg gcgtgggtgg cgaaaccga actgtccgcc     1500
aaagcctccg gccgcaaaat caccaaagcc aacttcccgt gggcggcttc cggccgtgcg    1560
attgccaacg gttgcgacaa gccgtttacc aagctgattt tgatgccga accggccgc      1620
atcatcggcg gcggcattgt cggtccgaac ggtggcgata tgatcggcga gtctgccttt    1680
gccatcgaaa tggctgcga gcggcagac atcggcaaaa ccatccaccc gcacccgacc     1740
ttgggcgaat ccatcggtat ggcggcggaa gtggcattgg gtacttgtac cgacctgcct    1800
ccgcaaaaga aaaaggatc cgacaggctg agaatggaca aactacagct caaaggaatg    1860
tcatactcta tgtgtacagg aaagtttaaa attgtgaagg aaatagcaga acacaacat     1920
ggaacaatag ttatcagagt acaatatgaa ggggacggct ctccatgtaa gatcccttt     1980
gagataatgg atttggaaaa agacacgtc ttaggtcgcc tgattacagt taacccgatc     2040
gtaacagaaa aagatagccc agtcaacata gaagcagaac ctccattcgg agacagctac    2100
atcatcatag gagtagagcc gggacaattg aaactcaact ggtttaagaa aggaagttcc    2160
```

```
atcggccaaa tgtttgagac aacaatgaga ggagcgaaga gaatggccat tttaggtgac    2220
acagcctggg attttgggtc tctgggtggt taaggatcc                           2259
```

<210> SEQ ID NO 31
<211> LENGTH: 745
<212> TYPE: PRT
<213> ORGANISM: Escherichia coli
<220> FEATURE:
<221> NAME/KEY: CHAIN
<222> LOCATION: (1)..(745)
<223> OTHER INFORMATION: Aminoacidic sequence of PLL3

<400> SEQUENCE: 31

```
His His His His His His Met Val Asp Lys Arg Met Ala Leu Val Glu
 1               5                  10                  15

Leu Lys Val Pro Asp Ile Gly Gly His Glu Asn Val Asp Ile Ile Ala
            20                  25                  30

Val Glu Val Asn Val Gly Asp Thr Ile Ala Val Asp Asp Thr Leu Ile
        35                  40                  45

Thr Leu Asp Met Asn Ser Met Asp Val Pro Ala Glu Val Ala Gly Val
    50                  55                  60

Val Lys Glu Val Lys Val Lys Val Gly Asp Lys Ile Ser Glu Gly Gly
65                  70                  75                  80

Leu Ile Val Val Glu Ala Glu Gly Thr Ala Ala Pro Lys Ala
                85                  90                  95

Glu Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240

Asp Pro His His Leu Glu Val Ser Leu Thr Ala Gly Asp Ala Tyr Glu
                245                 250                 255

Gln Ala Ala Pro Thr Gly Glu Lys Lys Ile Val Ala Phe Lys Asn Cys
            260                 265                 270

Ile Ile Ala Ala Gly Ser Arg Val Thr Lys Leu Pro Phe Ile Pro Glu
        275                 280                 285

Asp Pro Arg Ile Ile Asp Ser Ser Gly Ala Leu Ala Leu Lys Glu Val
    290                 295                 300

Pro Gly Lys Leu Leu Ile Ile Gly Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
```

```
                       340              345                350
Gln Lys Gln Asn Glu Tyr Arg Phe Asp Asn Ile Met Val Asn Thr Lys
            355                 360                 365
Thr Val Ala Val Glu Pro Lys Glu Asp Gly Val Tyr Val Thr Phe Glu
        370                 375                 380
Gly Ala Asn Ala Pro Lys Glu Pro Gln Arg Tyr Asp Ala Val Leu Val
385                 390                 395                 400
Ala Ala Gly Arg Ala Pro Asn Gly Lys Leu Ile Ser Ala Glu Lys Ala
                405                 410                 415
Gly Val Ala Val Thr Asp Arg Gly Phe Ile Glu Val Asp Lys Gln Met
            420                 425                 430
Arg Thr Asn Val Pro His Ile Tyr Ala Ile Gly Asp Ile Val Gly Gln
        435                 440                 445
Pro Met Leu Ala His Lys Ala Val His Glu Gly His Val Ala Ala Glu
        450                 455                 460
Asn Cys Ala Gly His Lys Ala Tyr Phe Asp Ala Arg Val Ile Pro Gly
465                 470                 475                 480
Val Ala Tyr Thr Ser Pro Glu Val Ala Trp Val Gly Glu Thr Glu Leu
                485                 490                 495
Ser Ala Lys Ala Ser Gly Arg Lys Ile Thr Lys Ala Asn Phe Pro Trp
            500                 505                 510
Ala Ala Ser Gly Arg Ala Ile Ala Asn Gly Cys Asp Lys Pro Phe Thr
        515                 520                 525
Lys Leu Ile Phe Asp Ala Glu Thr Gly Arg Ile Ile Gly Gly Gly Ile
        530                 535                 540
Val Gly Pro Asn Gly Gly Asp Met Ile Gly Glu Val Cys Leu Ala Ile
545                 550                 555                 560
Glu Met Gly Cys Asp Ala Ala Asp Ile Gly Lys Thr Ile His Pro His
                565                 570                 575
Pro Gly Glu Ser Ile Gly Met Ala Ala Glu Val Ala Leu Gly Thr Cys
            580                 585                 590
Thr Asp Leu Pro Pro Gln Lys Lys Gly Ser Arg Leu Arg Met Asp
        595                 600                 605
Lys Leu Gln Leu Lys Gly Met Ser Tyr Ser Met Cys Thr Gly Lys Phe
        610                 615                 620
Lys Ile Val Lys Glu Ile Ala Glu Thr Gln His Gly Thr Ile Val Ile
625                 630                 635                 640
Arg Val Gln Tyr Glu Gly Asp Gly Ser Pro Cys Lys Ile Pro Phe Glu
                645                 650                 655
Ile Met Asp Leu Glu Lys Arg His Val Leu Gly Arg Leu Ile Thr Val
            660                 665                 670
Asn Pro Ile Val Thr Glu Lys Asp Ser Pro Val Asn Ile Glu Ala Glu
        675                 680                 685
Pro Pro Phe Gly Asp Ser Tyr Ile Ile Gly Val Glu Pro Gly Gln
        690                 695                 700
Leu Lys Leu Asn Trp Phe Lys Lys Gly Ser Ser Ile Gly Gln Met Phe
705                 710                 715                 720
Glu Thr Thr Met Arg Gly Ala Lys Arg Met Ala Ile Leu Gly Asp Thr
                725                 730                 735
Ala Trp Asp Phe Gly Ser Leu Gly Gly
            740                 745

<210> SEQ ID NO 32
<211> LENGTH: 429
```

```
<212> TYPE: DNA
<213> ORGANISM: Escherichia coli
<220> FEATURE:
<221> NAME/KEY: gene
<222> LOCATION: (1)..(429)
<223> OTHER INFORMATION: Nucleotidic sequence coding for the aminoacids
      286 to 426 of the DEN-1 envelope protein

<400> SEQUENCE: 32
agactaaaaa tggataaact gactttaaaa ggggtatcat atgtaatgtg cacagggtca    60
ttcaagttag agaaggaagt ggctgagacc cagcatggaa ctgttctagt gcaggttaaa   120
tacgaaggaa cagatgcacc atgcaagatc cccttctcgt cccaagatga aaaggagta    180 acccagaatg ggagattgat aacagccaac cccatagtca ttgacaaaga aaaccagtc    240 aacattgaag cggagccacc ttttggtgag agctatattg tggtaggagc aggtgaaaaa   300
gctttgaaac taagctggtt caagaaggga agcagtatag ggaaaatgtt tgaagcaact   360
gcccgtggag cacgaaggat ggccatcctg ggagacaccg catgggactt cggttctata   420
ggagggtaa                                                           429

<210> SEQ ID NO 33
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric
      protein in the plasmid pLH1

<400> SEQUENCE: 33
atgggccacc accaccacca ccacgccatg gtagataaaa gaatggcttt agttgaattg    60
aaagtgcccg acattggcgg aacagaaaat gtagatatta tcgcggttga agtaaacgtg   120
ggcgacacta ttgctgtgga cgatacccty attactttgg atctagattt ggatctagac   180
aggctcaaaa tggataaact gactttaaaa ggggtatcat atgtaatgtg cacagggtca   240
ttcaagttag agaaggaagt ggctgagacc cagcatggaa ctgttctagt gcaggttaaa   300
tacgaaggaa cagatgcacc atgcaagatc cccttctcgt cccaagatga aaaggagta   360 acccagaatg ggagattgat aacagccaac cccatagtca ttgacaaaga aaaccagtc   420 aacattgaag cggagccacc ttttggtgag agctatattg tggtaggagc aggtgaaaaa   480
gctttgaaac taagctggtt caagaaggga agcagtatag ggaaaatgtt tgaagcaact   540
gcccgtggag cacgaaggat ggccatcctg ggagacaccg catgggactt cggttctatt   600
ggcgggtaag gatcc                                                    615

<210> SEQ ID NO 34
<211> LENGTH: 174
<212> TYPE: PRT
<213> ORGANISM: Escherichia coli
<220> FEATURE:
<221> NAME/KEY: CHAIN
<222> LOCATION: (1)..(174)
<223> OTHER INFORMATION: Aminoacidic sequence of the PLH1

<400> SEQUENCE: 34

His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
```

```
                 35                  40                  45
Thr Leu Asp Leu Asp Phe Lys Leu Glu Lys Glu Val Ala Glu Thr Gln
         50                  55                  60

His Gly Thr Val Leu Val Gln Val Lys Tyr Gln Gly Thr Asp Ala Pro
 65                  70                  75                  80

Cys Lys Ile Pro Phe Ser Thr Gln Asp Glu Lys Gly Val Thr Gln Asn
                 85                  90                  95

Arg Leu Ile Thr Ala Asn Pro Ile Val Thr Asp Lys Glu Lys Pro Val
             100                 105                 110

Asn Ile Glu Thr Glu Pro Pro Phe Gly Glu Ser Tyr Ile Val Val Gly
        115                 120                 125

Ala Gly Glu Lys Ala Leu Lys Gln Cys Trp Phe Lys Lys Gly Ser Ser
    130                 135                 140

Ile Gly Lys Met Phe Glu Ala Thr Ala Arg Gly Ala Arg Arg Met Ala
145                 150                 155                 160

Ile Leu Gly Asp Thr Ala Trp Asp Phe Gly Ser Ile Gly Gly
                165                 170

<210> SEQ ID NO 35
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence coding for the quimeric
      protein in the plasmid pLH2

<400> SEQUENCE: 35
atgggccacc accaccacca ccacgccatg gtagataaaa gaatggcttt agttgaattg      60
aaagtgcccg acattggcgg aacagaaaat gtagatatta tcgcggttga agtaaacgtg     120
ggcgacacta ttgctgtgga cgatacccctg attactttgg atctagattt ggatctagac     180
aggctcaaaa tggataaact gactttaaaa ggggtatcat atgtaatgtg cacagggtca     240
ttcaagttag agaaggaagt ggctgagacc cagcatggaa ctgttctagt gcaggttaaa     300
tacgaaggaa cagatgcacc atgcaagatc cccttctcgt cccaagatga aaaggagta      360 acccagaatg ggagattgat aacagccaac cccatagtca ttgacaaaga aaaaccagtc     420
aacattgaag cggagccacc ttttggtgag agctatattg tggtaggagc aggtgaaaaa     480
gctttgaaac taagctggtt caagaaggga agcagtatag ggaaaatgtt tgaagcaact     540
gcccgtggag cacgaaggat ggccatcctg ggagacaccg catgggactt cggatctata     600
ggaggggtga attcgatgaa ttcgatggac gtacctgctg aagttgcagg cgtagtcaaa     660
gaagttaaag ttaaagtcgg cgacaaaatc tctgaaggtg gtttgattgt cgtcgttgaa     720
gctgaaggca cggcagccgc tcctaaagcc gaagcggctg ccgccccggc gcaagaagcc     780
cctaaagctg ccgctcctgc tccgcaagcc gcgcaattcg gcggttctgc cgatgccgag     840
tacgacgtgg tcgtattggg tggcggtccc ggcggttact ccgctgcatt tgccgctgcc     900
gatgaaggct tgaaagtcgc catcgtcgaa cgttacaaaa ctttgggcgg cgtttgcctg     960
aacgtcggct gtatcccttc caaagccttg ttgcacaatg ccgccgttat cgacgaagtg    1020
cgccacttgg ctgccaacgg tatcaaatac cccgagccgg aactcgacat cgatatgctt    1080
cgcgcctaca agacggcgt agtttcccgc ctcacgggcg gtttggcagg tatggcgaaa    1140
agccgtaaag tggacgttat ccaaggcgac gggcaattct tagatccgca ccacttggaa    1200
gtgtcgctga ctgccggcga cgcgtacgaa caggcagccc ctaccggcga gaaaaaaatc    1260
```

```
gttgccttca aaaactgtat cattgcagca ggcagccgcg taaccaaact gcctttcatt    1320
cctgaagatc cgcgcatcat cgattccagc ggcgcattgg ctctgaaaga agtaccgggc    1380
aaactgctga ttatcggcgg cggcattatc ggcctcgaga tgggtacggt ttacagcacg    1440
ctgggttcgc gtttggatgt ggttgaaatg atggacggcc tgatgcaagg cgcagaccgc    1500
gatttggtaa agtatggca aaacaaaac gaataccgtt ttgacaacat tatggtcaac    1560
accaaaaccg ttgcagttga gccgaaagaa gacggcgttt acgttacctt tgaaggcgcg    1620
aacgcgccta agagccgca acgctacgat gccgtattgg ttgccgccgg ccgcgcgccc    1680
aacggcaaac tcatcagcgc ggaaaaagca ggcgttgccg taaccgatcg cggcttcatc    1740
gaagtggaca acaaatgcg taccaatgtg ccgcacatct acgccatcgg cgacatcgtc    1800
ggtcagccga tgttggcgca caagccgtt cacgaaggcc acgttgccgc cgaaaactgc    1860
gccggccaca agcctactt cgacgcacgc gtgattccgg gcgttgccta cacttccccc    1920
gaagtggcgt gggtgggcga aaccgaactg tccgccaaag cctccggccg caaaatcacc    1980
aaagccaact cccgtgggc ggcttccggc cgtgcgattg ccaacggttg cgacaagccg    2040
tttaccaagc tgattttga tgccgaaacc ggccgcatca tcggcggcgg cattgtcggt    2100
ccgaacggtg gcgatatgat cggcgaagtc tgccttgcca tcgaaatggg ctgcgacgcg    2160
gcagacatcg gcaaaaccat ccacccgcac ccgggcgaat ccatcggtat ggcggcggaa    2220
gtggcattgg gtacttgtac cgacaaaaaa aaa                                 2253
```

<210> SEQ ID NO 36
<211> LENGTH: 727
<212> TYPE: PRT
<213> ORGANISM: Escherichia coli
<220> FEATURE:
<221> NAME/KEY: CHAIN
<222> LOCATION: (1)..(727)
<223> OTHER INFORMATION: Aminoacidic sequence of the PLH2

<400> SEQUENCE: 36

```
His His His His His His Met Val Asp Lys Arg Met Ala Leu Val Glu
 1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Thr Leu Ile
         35                  40                  45

Thr Leu Asp Leu Asp Phe Lys Leu Glu Lys Glu Val Ala Glu Thr Gln
     50                  55                  60

His Gly Thr Val Leu Val Gln Val Lys Tyr Gln Gly Thr Asp Ala Pro
 65                  70                  75                  80

Cys Lys Ile Pro Phe Ser Thr Gln Asp Glu Lys Gly Val Thr Gln Asn
                 85                  90                  95

Arg Leu Ile Thr Ala Asn Pro Ile Val Thr Asp Lys Glu Lys Pro Val
            100                 105                 110

Asn Ile Glu Thr Glu Pro Pro Phe Gly Glu Ser Tyr Ile Val Val Gly
        115                 120                 125

Ala Gly Glu Lys Ala Leu Lys Gln Cys Trp Phe Lys Lys Gly Ser Ser
    130                 135                 140

Ile Gly Lys Met Phe Glu Ala Thr Ala Arg Gly Ala Arg Arg Met Ala
145                 150                 155                 160

Ile Leu Gly Asp Thr Ala Trp Asp Phe Gly Ser Ile Gly Gly Val Asn
                165                 170                 175
```

-continued

Ser Met Asn Ser Met Asp Val Pro Ala Glu Val Ala Gly Val Val Lys
            180                 185                 190

Glu Val Lys Val Lys Val Gly Asp Lys Ile Ser Glu Gly Gly Leu Ile
    195                 200                 205

Val Val Val Glu Ala Glu Gly Thr Ala Ala Pro Lys Ala Glu Ala
210                 215                 220

Ala Ala Ala Pro Ala Gln Glu Ala Pro Lys Ala Ala Pro Ala Pro
225                 230                 235                 240

Gln Ala Ala Gln Phe Gly Ser Ala Asp Ala Glu Tyr Asp Val Val
                245                 250                 255

Val Leu Gly Gly Pro Gly Gly Tyr Ser Ala Ala Phe Ala Ala Ala
            260                 265                 270

Asp Glu Gly Leu Lys Val Ala Ile Val Glu Arg Tyr Lys Thr Leu Gly
            275                 280                 285

Gly Val Cys Leu Asn Val Gly Cys Ile Pro Ser Lys Ala Leu Leu His
            290                 295                 300

Asn Ala Ala Val Ile Asp Glu Val Arg His Leu Ala Ala Asn Gly Ile
305                 310                 315                 320

Lys Tyr Pro Glu Pro Glu Leu Asp Ile Asp Met Leu Arg Ala Tyr Lys
                325                 330                 335

Asp Gly Val Val Ser Arg Leu Thr Gly Gly Leu Ala Gly Met Ala Lys
                340                 345                 350

Ser Arg Lys Val Asp Val Ile Gln Gly Asp Gly Gln Phe Leu Asp Pro
            355                 360                 365

His His Leu Glu Val Ser Leu Thr Ala Gly Asp Ala Tyr Glu Gln Ala
            370                 375                 380

Ala Pro Thr Gly Glu Lys Lys Ile Val Ala Phe Lys Asn Cys Ile Ile
385                 390                 395                 400

Ala Ala Gly Ser Arg Val Thr Lys Leu Pro Phe Ile Pro Glu Asp Pro
                405                 410                 415

Arg Ile Ile Asp Ser Ser Gly Ala Leu Ala Leu Lys Glu Val Pro Gly
            420                 425                 430

Lys Leu Leu Ile Ile Gly Gly Gly Ile Ile Gly Leu Glu Met Gly Thr
            435                 440                 445

Val Tyr Ser Thr Leu Gly Ser Arg Leu Asp Val Val Glu Met Met Asp
450                 455                 460

Gly Leu Met Gln Gly Ala Asp Arg Asp Leu Val Lys Val Trp Gln Lys
465                 470                 475                 480

Gln Asn Glu Tyr Arg Phe Asp Asn Ile Met Val Asn Thr Lys Thr Val
                485                 490                 495

Ala Val Glu Pro Lys Glu Asp Gly Val Tyr Val Thr Phe Glu Gly Ala
            500                 505                 510

Asn Ala Pro Lys Glu Pro Gln Arg Tyr Asp Ala Val Leu Val Ala Ala
            515                 520                 525

Gly Arg Ala Pro Asn Gly Lys Leu Ile Ser Ala Glu Lys Ala Gly Val
            530                 535                 540

Ala Val Thr Asp Arg Gly Phe Ile Glu Val Asp Lys Gln Met Arg Thr
545                 550                 555                 560

Asn Val Pro His Ile Tyr Ala Ile Gly Asp Ile Val Gly Gln Pro Met
                565                 570                 575

Leu Ala His Lys Ala Val His Glu Gly His Val Ala Ala Glu Asn Cys
            580                 585                 590

Ala Gly His Lys Ala Tyr Phe Asp Ala Arg Val Ile Pro Gly Val Ala
            595                 600                 605

```
Tyr Thr Ser Pro Glu Val Ala Trp Val Gly Glu Thr Glu Leu Ser Ala
    610                 615                 620

Lys Ala Ser Gly Arg Lys Ile Thr Lys Ala Asn Phe Pro Trp Ala Ala
625                 630                 635                 640

Ser Gly Arg Ala Ile Ala Asn Gly Cys Asp Lys Pro Phe Thr Lys Leu
                645                 650                 655

Ile Phe Asp Ala Glu Thr Gly Arg Ile Ile Gly Gly Ile Val Gly
                660                 665                 670

Pro Asn Gly Gly Asp Met Ile Gly Glu Val Cys Leu Ala Ile Glu Met
                675                 680                 685

Gly Cys Asp Ala Ala Asp Ile Gly Lys Thr Ile His Pro His Pro Gly
    690                 695                 700

Glu Ser Ile Gly Met Ala Ala Glu Val Ala Leu Gly Thr Cys Thr Asp
705                 710                 715                 720

Leu Pro Pro Gln Lys Lys Lys
                725
```

<210> SEQ ID NO 37
<211> LENGTH: 2250
<212> TYPE: DNA
<213> ORGANISM: Escherichia coli
<220> FEATURE:
<221> NAME/KEY: gene
<222> LOCATION: (1)..(2250)
<223> OTHER INFORMATION: Nucleotidic sequence coding for the quimeric
      protein in the plasmid pLH3

<400> SEQUENCE: 37

```
atgggccacc accaccacca ccacgccatg gtagataaaa gaatggcttt agttgaattg      60
aaagtgcccg acattggcgg acacgaaaat gtagatatta tcgcggttga agtaaacgtg     120
ggcgacacta ttgctgtgga cgatacccctg attactttgg atctagaaat ggacgtacct     180
gctgaagttg caggcgtagt caaagaagtt aaagttaaag tcggcgacaa aatctctgaa     240
ggtggtttga ttgtcgtcgt tgaagctgaa ggcacggcag ccgctcctaa agccgaagcg     300
gctgccgccc cggcgcaaga agcccctaaa gctgccgctc ctgctccgca agccgcgcaa     360
ttcggcggtt ctgccgatgc cgagtacgac gtggtcgtat gggtggcgg tcccggcggt     420 tactccgctg catttgccgc tgccgatgaa ggcttgaaag tcgccatcgt cgaacgttac     480
aaaactttgg gcggcgtttg cctgaacgtc ggctgtatcc cttccaaagc cttgttgcac     540
aatgccgccg ttatcgacga agtgcgccac ttggctgcca acggtatcaa ataccccgag     600
ccggaactcg acatcgatat gcttcgcgcc tacaaagacg gcgtagtttc ccgcctcacg     660
ggcggttggg caggtatggc gaaaagccgt aaagtggacg ttatccaagg cgacgggcaa     720
ttcttagatc gcaccacttt ggaagtgtcg ctgactgccg gcgacgcgta cgaacaggca     780 gccccctaccg gcgagaaaaa aatcgttgcc ttcaaaaact gtatcattgc agcaggcagc     840
cgcgtaacca aactgcctttt cattcctgaa gatccgcgca tcatcgattc cagcggcgca     900
ttggctctga agaagtacc gggcaaactg ctgattatcg gcggcggcat tatcggcctc     960
gagatgggta cggtttacag cacgctgggt tcgcgtttgg atgtggttga atgatggac    1020 ggcctgatgc aaggcgcaga ccgcgatttg gtaaagtat ggcaaaaaca aaacgaatac    1080
cgttttgaca acattatggt caacaccaaa accgttgcag ttgagccgaa agaagacggc    1140
gtttacgtta cctttgaagg cgcgaacgcg cctaaagagc gcaacgcta cgatgccgta    1200 ttggttgccg ccggccgcgc gcccaacggc aaactcatca gcgcggaaaa agcaggcgtt    1260
```

```
gccgtaaccg atcgcggctt catcgaagtg acaaacaaa tgcgtaccaa tgtgccgcac    1320
atctacgcca tcggcgacat cgtcggtcag ccgatgttgg cgcacaaagc cgttcacgaa    1380
ggccacgttg ccgccgaaaa ctgcgccggc cacaaagcct acttcgacgc acgcgtgatt    1440
ccgggcgttg cctacacttc ccccgaagtg gcgtgggtgg cgaaaccga actgtccgcc     1500 aaagcctccg ccgcaaaat caccaaagcc aacttcccgt gggcggcttc cggccgtgcg     1560
attgccaacg gttgcgacaa gccgtttacc aagctgattt ttgatgccga accggccgc     1620 atcatcggcg gcggcattgt cggtccgaac ggtggcgata tgatcggcga gtctgccttt    1680
gccatcgaaa tgggctgcga cgcggcagac atcggcaaaa ccatccaccc gcacccgacc    1740
ttgggcgaat ccatcggtat ggcggcggaa gtggcattgg gtacttgtac cgacctgcct    1800
ccgcaaaaga aaaaggatc cagactaaaa atggataaac tgactttaaa agggggtatca    1860 tatgtaatgt gcacagggtc attcaagtta gagaaggaag tggctgagac ccagcatgga    1920
actgttctag tgcaggttaa atacgaagga acagatgcac catgcaagat ccccttctcg    1980
tcccaagatg agaaaggagt aacccagaat gggagattga taacagccaa ccccatagtc    2040
attgacaaag aaaaaccagt caacattgaa gcggagccac ctttggtga gagctatatt     2100 gtggtaggag caggtgaaaa agctttgaaa ctaagctggt tcaagaaggg aagcagtata    2160
gggaaaatgt ttgaagcaac tgcccgtgga gcacgaagga tggccatcct gggagacacc    2220
gcatgggact tcggttctat aggtgggtaa                                     2250
```

<210> SEQ ID NO 38
<211> LENGTH: 724
<212> TYPE: PRT
<213> ORGANISM: Escherichia coli
<220> FEATURE:
<221> NAME/KEY: CHAIN
<222> LOCATION: (1)..(724)
<223> OTHER INFORMATION: Aminoacidic sequence of the PLH3

<400> SEQUENCE: 38

```
His His His His His His Met Val Asp Lys Arg Met Ala Leu Val Glu
 1               5                  10                  15

Leu Lys Val Pro Asp Ile Gly Gly His Glu Asn Val Asp Ile Ile Ala
                20                  25                  30

Val Glu Val Asn Val Gly Asp Thr Ile Ala Val Asp Asp Thr Leu Ile
         35                  40                  45

Thr Leu Asp Met Asn Ser Met Asp Val Pro Ala Glu Val Ala Gly Val
     50                  55                  60

Val Lys Glu Val Lys Val Lys Val Gly Asp Lys Ile Ser Glu Gly Gly
 65                  70                  75                  80

Leu Ile Val Val Val Glu Ala Glu Gly Thr Ala Ala Pro Lys Ala
                 85                  90                  95

Glu Ala Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
```

```
                180             185              190
Gly Ile Lys Tyr Pro Glu Pro Glu Leu Asp Ile Asp Met Leu Arg Ala
            195                 200             205
Tyr Lys Asp Gly Val Val Ser Arg Leu Thr Gly Gly Leu Ala Gly Met
            210                 215             220
Ala Lys Ser Arg Lys Val Asp Val Ile Gln Gly Asp Gly Gln Phe Leu
225                 230                 235                 240
Asp Pro His His Leu Glu Val Ser Leu Thr Ala Gly Asp Ala Tyr Glu
                245                 250                 255
Gln Ala Ala Pro Thr Gly Glu Lys Lys Ile Val Ala Phe Lys Asn Cys
            260                 265                 270
Ile Ile Ala Ala Gly Ser Arg Val Thr Lys Leu Pro Phe Ile Pro Glu
            275                 280                 285
Asp Pro Arg Ile Ile Asp Ser Ser Gly Ala Leu Ala Leu Lys Glu Val
            290                 295             300
Pro Gly Lys Leu Leu Ile Ile Gly Gly Gly Ile Ile Gly Leu Glu Met
305                 310                 315                 320
Gly Thr Val Tyr Ser Thr Leu Gly Ser Arg Leu Asp Val Val Glu Met
                325                 330                 335
Met Asp Gly Leu Met Gln Gly Ala Asp Arg Asp Leu Val Lys Val Trp
            340                 345                 350
Gln Lys Gln Asn Glu Tyr Arg Phe Asp Asn Ile Met Val Asn Thr Lys
            355                 360                 365
Thr Val Ala Val Glu Pro Lys Glu Asp Gly Val Tyr Val Thr Phe Glu
            370                 375             380
Gly Ala Asn Ala Pro Lys Glu Pro Gln Arg Tyr Asp Ala Val Leu Val
385                 390                 395                 400
Ala Ala Gly Arg Ala Pro Asn Gly Lys Leu Ile Ser Ala Glu Lys Ala
                405                 410                 415
Gly Val Ala Val Thr Asp Arg Gly Phe Ile Glu Val Asp Lys Gln Met
            420                 425             430
Arg Thr Asn Val Pro His Ile Tyr Ala Ile Gly Asp Ile Val Gly Gln
            435                 440             445
Pro Met Leu Ala His Lys Ala Val His Glu Gly His Val Ala Ala Glu
            450                 455             460
Asn Cys Ala Gly His Lys Ala Tyr Phe Asp Ala Arg Val Ile Pro Gly
465                 470                 475                 480
Val Ala Tyr Thr Ser Pro Glu Val Ala Trp Val Gly Glu Thr Glu Leu
                485                 490                 495
Ser Ala Lys Ala Ser Gly Arg Lys Ile Thr Lys Ala Asn Phe Pro Trp
            500                 505             510
Ala Ala Ser Gly Arg Ala Ile Ala Asn Gly Cys Asp Lys Pro Phe Thr
            515                 520             525
Lys Leu Ile Phe Asp Ala Glu Thr Gly Arg Ile Ile Gly Gly Gly Ile
            530                 535             540
Val Gly Pro Asn Gly Gly Asp Met Ile Gly Glu Val Cys Leu Ala Ile
545                 550                 555                 560
Glu Met Gly Cys Asp Ala Ala Asp Ile Gly Lys Thr Ile His Pro His
                565                 570                 575
Pro Gly Glu Ser Ile Gly Met Ala Ala Glu Val Ala Leu Gly Thr Cys
            580                 585             590
Thr Asp Leu Pro Pro Gln Lys Lys Lys Gly Ser Phe Lys Leu Glu Lys
            595                 600             605
```

| | | | | | | | | | | | | |
|---|---|---|---|---|---|---|---|---|---|---|---|---|
|Glu|Val|Ala|Glu|Thr|Gln|His|Gly|Thr|Val|Leu|Val|Gln|Val|Lys|Tyr|
| |610| | | |615| | | |620| | | | | | |

Gln Gly Thr Asp Ala Pro Cys Lys Ile Pro Phe Ser Thr Gln Asp Glu
625                 630                 635                 640

Lys Gly Val Thr Gln Asn Arg Leu Ile Thr Ala Asn Pro Ile Val Thr
            645                 650                 655

Asp Lys Glu Lys Pro Val Asn Ile Glu Thr Glu Pro Pro Phe Gly Glu
            660                 665                 670

Ser Tyr Ile Val Val Gly Ala Gly Glu Lys Ala Leu Lys Gln Cys Trp
        675                 680                 685

Phe Lys Lys Gly Ser Ser Ile Gly Lys Met Phe Glu Ala Thr Ala Arg
        690                 695                 700

Gly Ala Arg Arg Met Ala Ile Leu Gly Asp Thr Ala Trp Asp Phe Gly
705                 710                 715                 720

Ser Ile Gly Gly

<210> SEQ ID NO 39
<211> LENGTH: 426
<212> TYPE: DNA
<213> ORGANISM: Escherichia coli
<220> FEATURE:
<221> NAME/KEY: gene
<222> LOCATION: (1)..(426)
<223> OTHER INFORMATION: Nucleotidic sequence coding for the aminoacids
      286 to 426 of the DEN-3 envelope protein

<400> SEQUENCE: 39
agactcaaga tggacaaatt gaaactcaag gggatgagct atgcaatgtg cttgaatacc      60
tttgtgttga agaaagaagt ctccgaaacg cagcatggga caatactcat taaggttgag     120
tacaaagggg aagatgcacc ctgcaagatt cctttctcca cggaggatgg acaagggaaa     180
gctcacaatg gcagactgat cacagccaat ccagtggtga ccaagaagga ggagcctgtc     240
aacattgagg ctgaacctcc ttttggggaa agtaatatag taattggaat tggagacaaa     300
gccctgaaaa tcaactggta caggaaggga agctcgattg ggaagatgtt cgaggccact     360
gccagaggtc aaggcgcat ggccatcttg ggagacacag cctgggactt tggatcagtg     420
ggtggt                                                               426

<210> SEQ ID NO 40
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric
      protein in the plasmid pAZ1

<400> SEQUENCE: 40
atgggccacc accaccacca ccacgccatg gtagataaaa gaatggcttt agttgaattg      60
aaagtgcccg acattggcgg aacagaaaat gtagatatta tcgcggttga agtaaacgtg     120
ggcgacacta ttgctgtgga cgatacctg attactttgg atctagattt ggatctagat     180
agactcaaga tggacaaatt gaaactcaag gggatgagct atgcaatgtg cttgaatacc     240
tttgtgttga agaaagaagt ctccgaaacg cagcatggga caatactcat taaggttgag     300
tacaaagggg aagatgcacc ctgcaagatt cctttctcca cggaggatgg acaagggaaa     360
gctcacaatg gcagactgat cacagccaat ccagtggtga ccaagaagga ggagcctgtc     420
aacattgagg ctgaacctcc ttttggggaa agtaatatag taattggaat tggagacaaa     480

```
gccctgaaaa tcaactggta caggaaggga agctcgattg ggaagatgtt cgaggccact    540
gccagaggtg caaggcgcat ggccatcttg ggagacacag cctgggactt tggttcagtg    600
ggtggttaag gatcc                                                     615
```

<210> SEQ ID NO 41
<211> LENGTH: 194
<212> TYPE: PRT
<213> ORGANISM: Escherichia coli
<220> FEATURE:
<221> NAME/KEY: CHAIN
<222> LOCATION: (1)..(194)
<223> OTHER INFORMATION: Aminoacidic sequence of the PAZ1

<400> SEQUENCE: 41

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Arg Leu Lys Met Asp Lys Leu Lys Leu Lys Gly
     50                  55                  60

Met Ser Tyr Ala Met Cys Leu Asn Thr Phe Val Leu Lys Lys Glu Val
 65                  70                  75                  80

Ser Glu Thr His Gly Thr Ile Leu Ile Lys Val Glu Tyr Lys Gly Glu
                 85                  90                  95

Asp Ala Pro Cys Lys Ile Pro Phe Ser Thr Glu Asp Gly Gln Gly Lys
            100                 105                 110

Ala His Asn Gly Arg Leu Ile Thr Ala Asn Pro Val Val Thr Lys Lys
        115                 120                 125

Glu Glu Pro Val Asn Ile Glu Ala Glu Pro Pro Phe Gly Glu Ser Asn
    130                 135                 140

Ile Val Ile Gly Ile Gly Asp Lys Ala Leu Lys Ile Asn Trp Tyr Arg
145                 150                 155                 160

Lys Gly Ser Ser Ile Gly Lys Met Phe Glu Ala Thr Ala Arg Gly Ala
                165                 170                 175

Arg Arg Met Ala Ile Leu Gly Asp Thr Ala Trp Asp Phe Gly Ser Val
            180                 185                 190

Gly Gly
```

<210> SEQ ID NO 42
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence coding for the quimeric
      protein in the plasmid pAZ2

<400> SEQUENCE: 42

```
atgggccacc accaccacca ccacgccatg gtagataaaa gaatggcttt agttgaattg     60
aaagtgcccg acattggcgg aacagaaaat gtagatatta tcgcggttga agtaaacgtg    120
ggcgacacta ttgctgtgga cgatacccctg attactttgg atctagattt ggatctagat    180
agactcaaga tggacaaatt gaaactcaag gggatgagct atgcaatgtg cttgaatacc    240
tttgtgttga agaaagaagt ctccgaaacg cagcatggga caatactcat taaggttgag    300
```

-continued

```
tacaaagggg aagatgcacc ctgcaagatt cctttctcca cggaggatgg acaagggaaa      360
gctcacaatg cagactgat cacagccaat ccagtggtga ccaagaagga ggagcctgtc      420
aacattgagg ctgaacctcc ttttggggaa agtaatatag taattggaat tggagacaaa      480
gccctgaaaa tcaactggta caggaaggga agctcgattg gaagatgtt cgaggccact      540
gccagaggtg caaggcgcat ggccatcttg ggagacacag cctgggactt tggatctgtg      600
ggtggtgtga attcgatgaa ttcgatggac gtacctgctg aagttgcagg cgtagtcaaa      660
gaagttaaag ttaaagtcgg cgacaaaatc tctgaaggtg gtttgattgt cgtcgttgaa      720
gctgaaggca cggcagccgc tcctaaagcc gaagcggctg ccgccccggc gaagaagcc      780
cctaaagctg ccgctcctgc tccgcaagcc gcgcaattcg gcggttctgc cgatgccgag      840
tacgacgtgg tcgtattggg tggcggtccc ggcggttact ccgctgcatt tgccgctgcc      900
gatgaaggct tgaaagtcgc catcgtcgaa cgttacaaaa ctttgggcgg cgtttgcctg      960
aacgtcggct gtatcccttc caaagccttg ttgcacaatg ccgccgttat cgacgaagtg     1020
cgccacttgg ctgccaacgg tatcaaatac cccgagccgg aactcgacat cgatatgctt     1080
cgcgcctaca aagacggcgt agtttcccgc ctcacgggcg gtttggcagg tatggcgaaa     1140
agccgtaaag tggacgttat ccaaggcgac gggcaattct tagatccgca ccacttggaa     1200
gtgtcgctga ctgccggcga cgcgtacgaa caggcagccc ctaccggcga gaaaaaaatc     1260
gttgccttca aaaactgtat cattgcagca ggcagccgcg taaccaaact gcctttcatt     1320
cctgaagatc cgcgcatcat cgattccagc ggcgcattgg ctctgaaaga agtaccgggc     1380
aaactgctga ttatcggcgg cggcattatc ggcctcgaga tgggtacggt ttacagcacg     1440
ctgggttcgc gtttggatgt ggttgaaatg atggacggcc tgatgcaagg cgcagaccgc     1500
gatttggtaa agtatggca aaaacaaaac gaataccgtt ttgacaacat tatggtcaac     1560
accaaaaccg ttgcagttga ccgaaagaa gacggcgttt acgttacctt gaaggcgcg     1620
aacgcgccta agagccgca acgctacgat gccgtattgg ttgccgccgg ccgcgcgccc     1680
aacggcaaac tcatcagcgc ggaaaaagca ggcgttgccg taaccgatcg cggcttcatc     1740
gaagtggaca acaaatgcg taccaatgtg ccgcacatct acgccatcgg cgacatcgtc     1800
ggtcagccga tgttggcgca caagccgtt cacgaaggcc acgttgccgc cgaaaactgc     1860
gccggccaca aagcctactt cgacgcacgc gtgattccgg cgttgccta cacttccccc     1920
gaagtggcgt gggtgggcga aaccgaactg tccgccaaag cctccggccg caaaatcacc     1980
aaagccaact tcccgtgggc ggcttccggc cgtgcgattg ccaacggttg cgacaagccg     2040
tttaccaagc tgattttga tgccgaaacc ggccgcatca tcggcggcgg cattgtcggt     2100
ccgaacggtg gcgatatgat cggcgaagtc tgccttgcca tcgaaatggg ctgcgacgcg     2160
gcagacatcg gcaaaaccat ccacccgcac ccgggcgaat ccatcggtat ggcggcggaa     2220
gtggcattgg gtacttgtac cgacaaaaaa aaa                                  2253
```

<210> SEQ ID NO 43
<211> LENGTH: 747
<212> TYPE: PRT
<213> ORGANISM: Escherichia coli
<220> FEATURE:
<221> NAME/KEY: CHAIN
<222> LOCATION: (1)..(747)
<223> OTHER INFORMATION: Aminoacidic sequence of the PAZ2

<400> SEQUENCE: 43

```
His His His His His His Met Val Asp Lys Arg Met Ala Leu Val Glu
 1               5                  10                  15
```

```
Leu Lys Val Pro Asp Ile Gly Gly His Glu Asn Val Asp Ile Ile Ala
            20                  25                  30
Val Glu Val Asn Val Gly Asp Thr Ile Ala Val Asp Asp Thr Leu Ile
            35                  40                  45
Thr Leu Asp Leu Asp Arg Leu Lys Met Asp Lys Leu Lys Leu Lys Gly
 50                  55                  60
Met Ser Tyr Ala Met Cys Leu Asn Thr Phe Val Leu Lys Lys Glu Val
 65                  70                  75                  80
Ser Glu Thr His Gly Thr Ile Leu Ile Lys Val Glu Tyr Lys Gly Glu
                 85                  90                  95
Asp Ala Pro Cys Lys Ile Pro Phe Ser Thr Glu Asp Gly Gln Gly Lys
            100                 105                 110
Ala His Asn Gly Arg Leu Ile Thr Ala Asn Pro Val Val Thr Lys Lys
            115                 120                 125
Glu Glu Pro Val Asn Ile Glu Ala Glu Pro Pro Phe Gly Glu Ser Asn
130                 135                 140
Ile Val Ile Gly Ile Gly Asp Lys Ala Leu Lys Ile Asn Trp Tyr Arg
145                 150                 155                 160
Lys Gly Ser Ser Ile Gly Lys Met Phe Glu Ala Thr Ala Arg Gly Ala
                165                 170                 175
Arg Arg Met Ala Ile Leu Gly Asp Thr Ala Trp Asp Phe Gly Ser Val
            180                 185                 190
Gly Gly Val Asn Ser Met Asn Ser Met Asp Val Pro Ala Glu Val Ala
            195                 200                 205
Gly Val Val Lys Glu Val Lys Val Lys Val Gly Asp Lys Ile Ser Glu
            210                 215                 220
Gly Gly Leu Ile Val Val Glu Ala Glu Gly Thr Ala Ala Ala Pro
225                 230                 235                 240
Lys Ala Glu Ala Ala Ala Pro Ala Gln Glu Ala Pro Lys Ala Ala
                245                 250                 255
Ala Pro Ala Pro Gln Ala Ala Gln Phe Gly Gly Ser Ala Asp Ala Glu
            260                 265                 270
Tyr Asp Val Val Leu Gly Gly Pro Gly Gly Tyr Ser Ala Ala
            275                 280                 285
Phe Ala Ala Ala Asp Glu Gly Leu Lys Val Ala Ile Val Glu Arg Tyr
290                 295                 300
Lys Thr Leu Gly Gly Val Cys Leu Asn Val Gly Cys Ile Pro Ser Lys
305                 310                 315                 320
Ala Leu Leu His Asn Ala Ala Val Ile Asp Glu Val Arg His Leu Ala
                325                 330                 335
Ala Asn Gly Ile Lys Tyr Pro Glu Pro Glu Leu Asp Ile Asp Met Leu
            340                 345                 350
Arg Ala Tyr Lys Asp Gly Val Val Ser Arg Leu Thr Gly Gly Leu Ala
            355                 360                 365
Gly Met Ala Lys Ser Arg Lys Val Asp Val Ile Gln Gly Asp Gly Gln
            370                 375                 380
Phe Leu Asp Pro His His Leu Glu Val Ser Leu Thr Ala Gly Asp Ala
385                 390                 395                 400
Tyr Glu Gln Ala Ala Pro Thr Gly Glu Lys Lys Ile Val Ala Phe Lys
            405                 410                 415
Asn Cys Ile Ile Ala Ala Gly Ser Arg Val Thr Lys Leu Pro Phe Ile
            420                 425                 430
Pro Glu Asp Pro Arg Ile Ile Asp Ser Ser Gly Ala Leu Ala Leu Lys
```

```
                 435                 440                 445
Glu Val Pro Gly Lys Leu Leu Ile Ile Gly Gly Ile Ile Gly Leu
            450                 455                 460

Glu Met Gly Thr Val Tyr Ser Thr Leu Gly Ser Arg Leu Asp Val Val
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
            500                 505                 510

Thr Lys Thr Val Ala Val Glu Pro Lys Glu Asp Gly Val Tyr Val Thr
515                 520                 525

Phe Glu Gly Ala Asn Ala Pro Lys Glu Pro Gln Arg Tyr Asp Ala Val
            530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575

Gln Met Arg Thr Asn Val Pro His Ile Tyr Ala Ile Gly Asp Ile Val
            580                 585                 590

Gly Gln Pro Met Leu Ala His Lys Ala Val His Glu Gly His Val Ala
            595                 600                 605

Ala Glu Asn Cys Ala Gly His Lys Ala Tyr Phe Asp Ala Arg Val Ile
610                 615                 620

Pro Gly Val Ala Tyr Thr Ser Pro Glu Val Ala Trp Val Gly Glu Thr
625                 630                 635                 640

Glu Leu Ser Ala Lys Ala Ser Gly Arg Lys Ile Thr Lys Ala Asn Phe
                645                 650                 655

Pro Trp Ala Ala Ser Gly Arg Ala Ile Ala Asn Gly Cys Asp Lys Pro
            660                 665                 670

Phe Thr Lys Leu Ile Phe Asp Ala Glu Thr Gly Arg Ile Ile Gly Gly
            675                 680                 685

Gly Ile Val Gly Pro Asn Gly Gly Asp Met Ile Gly Glu Val Cys Leu
690                 695                 700

Ala Ile Glu Met Gly Cys Asp Ala Ala Asp Ile Gly Lys Thr Ile His
705                 710                 715                 720

Pro His Pro Gly Glu Ser Ile Gly Met Ala Ala Glu Val Ala Leu Gly
                725                 730                 735

Thr Cys Thr Asp Leu Pro Pro Gln Lys Lys Lys
            740                 745

<210> SEQ ID NO 44
<211> LENGTH: 2256
<212> TYPE: DNA
<213> ORGANISM: Escherichia coli
<220> FEATURE:
<221> NAME/KEY: gene
<222> LOCATION: (1)..(2256)
<223> OTHER INFORMATION: Nucleotidic sequence coding for the quimeric
      protein in the plasmid pAZ3

<400> SEQUENCE: 44
atgggccacc accaccacca ccacgccatg gtagataaaa gaatggcttt agttgaattg        60
aaagtgcccg acattggcgg acacgaaaat gtagatatta tcgcggttga agtaaacgtg       120
ggcgacacta ttgctgtgga cgatacccct attactttgg atctagaaat ggacgtacct       180
gctgaagttg caggcgtagt caaagaagtt aaagttaaag tcggcgacaa aatctctgaa       240
```

| | |
|---|---|
| ggtggtttga ttgtcgtcgt tgaagctgaa ggcacggcag ccgctcctaa agccgaagcg | 300 |
| gctgccgccc cggcgcaaga agcccctaaa gctgccgctc ctgctccgca agccgcgcaa | 360 |
| ttcggcggtt ctgccgatgc cgagtacgac gtggtcgtat tgggtggcgg tcccggcggt | 420 |
| tactccgctg catttgccgc tgccgatgaa ggcttgaaag tcgccatcgt cgaacgttac | 480 |
| aaaactttgg gcggcgtttg cctgaacgtc ggctgtatcc cttccaaagc cttgttgcac | 540 |
| aatgccgccg ttatcgacga agtgcgccac ttggctgcca acggtatcaa ataccccgag | 600 |
| ccggaactcg acatcgatat gcttcgcgcc tacaaagacg gcgtagtttc cgcctcacg | 660 |
| ggcggtttgg caggtatggc gaaaagccgt aaagtggacg ttatccaagg cgacgggcaa | 720 |
| ttcttagatc cgcaccactt ggaagtgtcg ctgactgccg gcgacgcgta cgaacaggca | 780 |
| gcccctaccg gcgagaaaaa aatcgttgcc ttcaaaaact gtatcattgc agcaggcagc | 840 |
| cgcgtaacca aactgccttt cattcctgaa gatccgcgca tcatcgattc cagcggcgca | 900 |
| ttggctctga agaagtaccc gggcaaactg ctgattatcg gcggcggcat tatcggcctc | 960 |
| gagatgggta cggtttacag cacgctgggt tcgcgtttgg atgtggttga atgatggac | 1020 |
| ggcctgatgc aaggcgcaga ccgcgatttg gtaaaagtat ggcaaaaaca aaacgaatac | 1080 |
| cgttttgaca acattatggt caacaccaaa accgttgcag ttgagccgaa agaagacggc | 1140 |
| gtttacgtta cctttgaagg cgcgaacgcg cctaaagagc cgcaacgcta cgatgccgta | 1200 |
| ttggttgccg ccggccgcgc gcccaacggc aaactcatca gcgcggaaaa agcaggcgtt | 1260 |
| gccgtaaccg atcgcggctt catcgaagtg acaaacaaa tgcgtaccaa tgtgccgcac | 1320 |
| atctacgcca tcggcgacat cgtcggtcag ccgatgttgg cgcacaaagc cgttcacgaa | 1380 |
| ggccacgttg ccgccgaaaa ctgcgccggc cacaaagcct acttcgacgc acgcgtgatt | 1440 |
| ccgggcgttg cctacacttc ccccgaagtg gcgtgggtgg gcgaaaccga actgtccgcc | 1500 |
| aaagcctccg gccgcaaaat caccaaagcc aacttcccgt gggcggcttc cggccgtgcg | 1560 |
| attgccaacg gttgcgacaa gccgtttacc aagctgattt ttgatgccga aaccggccgc | 1620 |
| atcatcggcg gcggcattgt cggtccgaac ggtggcgata tgatcggcga agtctgcctt | 1680 |
| gccatcgaaa tgggctgcga cgcggcagac atcggcaaaa ccatccaccc gcaccgacc | 1740 |
| ttgggcgaat ccatcggtat ggcggcggaa gtggcattgg gtacttgtac cgacctgcct | 1800 |
| ccgcaaaaga aaaaggatc cagactcaag atggacaaat tgaaactcaa ggggatgagc | 1860 |
| tatgcaatgt gcttgaatac ctttgtgttg aagaaagaag tctccgaaac gcagcatggg | 1920 |
| acaatactca ttaaggttga gtacaaaggg gaagatgcac cctgcaagat tcctttctcc | 1980 |
| acggaggatg gacaagggaa agctcacaat ggcagactga tcacagccaa tccagtggtg | 2040 |
| accaagaagg aggagcctgt caacattgag gctgaacctc cttttgggga agtaatata | 2100 |
| gtaattggaa ttggagacaa agccctgaaa atcaactggt acaggaaggg aagctcgatt | 2160 |
| gggaagatgt tcgaggccac tgccagaggt gcaaggcgca tggccatctt gggagacaca | 2220 |
| gcctgggact ttggttcagt gggtggttaa ggatcc | 2256 |

<210> SEQ ID NO 45
<211> LENGTH: 744
<212> TYPE: PRT
<213> ORGANISM: Escherichia coli
<220> FEATURE:
<221> NAME/KEY: CHAIN
<222> LOCATION: (1)..(744)
<223> OTHER INFORMATION: Aminoacidic sequence of the PAZ3

<400> SEQUENCE: 45

-continued

```
His His His His His His Met Val Asp Lys Arg Met Ala Leu Val Glu
 1               5                   10                  15
Leu Lys Val Pro Asp Ile Gly Gly His Glu Asn Val Asp Ile Ile Ala
             20                  25                  30
Val Glu Val Asn Val Gly Asp Thr Ile Ala Val Asp Asp Thr Leu Ile
             35                  40                  45
Thr Leu Asp Met Asn Ser Met Asp Val Pro Ala Glu Val Ala Gly Val
         50                  55                  60
Val Lys Glu Val Lys Val Lys Val Gly Asp Lys Ile Ser Glu Gly Gly
 65                  70                  75                  80
Leu Ile Val Val Val Glu Ala Glu Gly Thr Ala Ala Pro Lys Ala
                 85                  90                  95
Glu Ala Ala Ala Ala Pro Ala Gln Glu Ala Pro Lys Ala Ala Ala Pro
             100                 105                 110
Ala Pro Gln Ala Ala Gln Phe Gly Gly Ser Ala Asp Ala Glu Tyr Asp
             115                 120                 125
Val Val Val Leu Gly Gly Gly Pro Gly Gly Tyr Ser Ala Ala Phe Ala
             130                 135                 140
Ala Ala Asp Glu Gly Leu Lys Val Ala Ile Val Glu Arg Tyr Lys Thr
145                 150                 155                 160
Leu Gly Gly Val Cys Leu Asn Val Gly Cys Ile Pro Ser Lys Ala Leu
                 165                 170                 175
Leu His Asn Ala Ala Val Ile Asp Glu Val Arg His Leu Ala Ala Asn
             180                 185                 190
Gly Ile Lys Tyr Pro Glu Pro Glu Leu Asp Ile Asp Met Leu Arg Ala
             195                 200                 205
Tyr Lys Asp Gly Val Val Ser Arg Leu Thr Gly Gly Leu Ala Gly Met
             210                 215                 220
Ala Lys Ser Arg Lys Val Asp Val Ile Gln Gly Asp Gly Gln Phe Leu
225                 230                 235                 240
Asp Pro His His Leu Glu Val Ser Leu Thr Ala Gly Asp Ala Tyr Glu
             245                 250                 255
Gln Ala Ala Pro Thr Gly Glu Lys Lys Ile Val Ala Phe Lys Asn Cys
             260                 265                 270
Ile Ile Ala Ala Gly Ser Arg Val Thr Lys Leu Pro Phe Ile Pro Glu
             275                 280                 285
Asp Pro Arg Ile Ile Asp Ser Ser Gly Ala Leu Ala Leu Lys Glu Val
             290                 295                 300
Pro Gly Lys Leu Leu Ile Gly Gly Ile Ile Gly Leu Glu Met
305                 310                 315                 320
Gly Thr Val Tyr Ser Thr Leu Gly Ser Arg Leu Asp Val Val Glu Met
                 325                 330                 335
Met Asp Gly Leu Met Gln Gly Ala Asp Arg Asp Leu Val Lys Val Trp
             340                 345                 350
Gln Lys Gln Asn Glu Tyr Arg Phe Asp Asn Ile Met Val Asn Thr Lys
             355                 360                 365
Thr Val Ala Val Glu Pro Lys Glu Asp Gly Val Tyr Thr Phe Glu
             370                 375                 380
Gly Ala Asn Ala Pro Lys Glu Pro Gln Arg Tyr Asp Ala Val Leu Val
385                 390                 395                 400
Ala Ala Gly Arg Ala Pro Asn Gly Lys Leu Ile Ser Ala Glu Lys Ala
                 405                 410                 415
Gly Val Ala Val Thr Asp Arg Gly Phe Ile Glu Val Asp Lys Gln Met
             420                 425                 430
```

```
Arg Thr Asn Val Pro His Ile Tyr Ala Ile Gly Asp Ile Val Gly Gln
        435                 440                 445

Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Lys Gly Ser Arg Leu Lys Met Asp
        595                 600                 605

Lys Leu Lys Leu Lys Gly Met Ser Tyr Ala Met Cys Leu Asn Thr Phe
    610                 615                 620

Val Leu Lys Lys Glu Val Ser Glu Thr His Gly Thr Ile Leu Ile Lys
625                 630                 635                 640

Val Glu Tyr Lys Gly Glu Asp Ala Pro Cys Lys Ile Pro Phe Ser Thr
                645                 650                 655

Glu Asp Gly Gln Gly Lys Ala His Asn Gly Arg Leu Ile Thr Ala Asn
            660                 665                 670

Pro Val Val Thr Lys Lys Glu Glu Pro Val Asn Ile Glu Ala Glu Pro
        675                 680                 685

Pro Phe Gly Glu Ser Asn Ile Val Ile Gly Ile Gly Asp Lys Ala Leu
    690                 695                 700

Lys Ile Asn Trp Tyr Arg Lys Gly Ser Ser Ile Gly Lys Met Phe Glu
705                 710                 715                 720

Ala Thr Ala Arg Gly Ala Arg Arg Met Ala Ile Leu Gly Asp Thr Ala
                725                 730                 735

Trp Asp Phe Gly Ser Val Gly Gly
            740
```

<210> SEQ ID NO 46
<211> LENGTH: 426
<212> TYPE: DNA
<213> ORGANISM: Escherichia coli
<220> FEATURE:
<221> NAME/KEY: gene
<222> LOCATION: (1)..(426)
<223> OTHER INFORMATION: Nucleotidic sequence coding for the aminoacids
      286 to 426 of the DEN-4 envelope protein

<400> SEQUENCE: 46

```
aaagtccgta tggagaaatt gagaatcaag ggaatgtcat acacgatgtg ttcaggaaag      60
ttttcaattg acaaagagat ggcagaaaca cagcatggga caacagtggt gaaagtcaag     120
tatgaaggtg ctggagctcc gtgtaaagtc cccatagaga taagagatgt aaacaaggaa     180
```

-continued

```
aaagtggttg ggcgtatcat ctcatccacc cctttggctg agaataccaa cagtgtaacc    240
aacatagaat tagaaccccc ctttggggac agctacatag tgataggtgt tggaaacagc    300
gcattaacac tccattggtt caggaaaggg agttccattg caagatgtt tgagtccaca     360 tacagaggtg caaaacgaat ggccattcta ggtgaaacag cttgggattt tggttccgtt    420
ggtgga                                                              426
```

<210> SEQ ID NO 47
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric
      protein in the plasmid pID1

<400> SEQUENCE: 47

```
atgggccacc accaccacca ccacgccatg gtagataaaa gaatggcttt agttgaattg     60
aaagtgcccg acattggcgg aacagaaaat gtagatatta tcgcggttga agtaaacgtg    120
ggcgacacta ttgctgtgga cgataccctg attactttgg atctagattt ggatctagac    180
aaagtgcgta tggagaaatt gagaatcaag ggaatgtcat acacgatgtg ttcaggaaag    240
ttttcaattg acaagagat ggcagaaaca cagcatggga caacagtggt gaaagtcaag    300
tatgaaggtg ctggagctcc gtgtaaagtc cccatagaga taagagatgt aaacaaggaa    360
aaagtggttg ggcgtatcat ctcatccacc cctttggctg agaataccaa cagtgtaacc    420
aacatagaat tagaaccccc ctttggggac agctacatag tgataggtgt tggaaacagc    480
gcattaacac tccattggtt caggaaaggg agttccattg caagatgtt tgagtccaca    540 tacagaggtg caaaacgaat ggccattcta ggtgaaacag cttgggattt tggttccgtt    600
ggtggataag gatcc                                                    615
```

<210> SEQ ID NO 48
<211> LENGTH: 192
<212> TYPE: PRT
<213> ORGANISM: Escherichia coli
<220> FEATURE:
<221> NAME/KEY: CHAIN
<222> LOCATION: (1)..(192)
<223> OTHER INFORMATION: Aminoacidic sequence of the PID1

<400> SEQUENCE: 48

```
His His His His His His Met Val Asp Lys Arg Met Ala Leu Val Glu
 1               5                  10                  15

Leu Lys Val Pro Asp Ile Gly Gly His Glu Asn Val Asp Ile Ile Ala
            20                  25                  30

Val Glu Val Asn Val Gly Asp Thr Ile Ala Val Asp Asp Thr Leu Ile
        35                  40                  45

Thr Leu Asp Lys Val Arg Met Glu Lys Leu Arg Ile Lys Gly Met Ser
    50                  55                  60

Tyr Thr Met Cys Ser Gly Lys Phe Ser Ile Asp Lys Glu Met Ala Glu
65                  70                  75                  80

Thr Gln His Gly Thr Thr Val Val Lys Val Lys Tyr Glu Gly Ala Gly
                85                  90                  95

Ala Pro Cys Lys Val Pro Ile Glu Ile Arg Asp Val Asn Lys Glu Lys
            100                 105                 110

Val Val Gly Arg Ile Ile Ser Ser Thr Pro Leu Ala Glu Asn Thr Asn
        115                 120                 125
```

Ser Val Thr Asn Ile Glu Leu Glu Arg Pro Leu Asp Ser Tyr Ile Val
    130                 135                 140

Ile Gly Val Gly Asn Ser Ala Leu Thr Leu His Trp Phe Arg Lys Gly
145                 150                 155                 160

Ser Ser Ile Gly Lys Met Phe Glu Ser Thr Tyr Arg Gly Ala Lys Arg
                165                 170                 175

Met Ala Ile Leu Gly Glu Thr Ala Trp Asp Phe Gly Ser Val Gly Gly
            180                 185                 190

<210> SEQ ID NO 49
<211> LENGTH: 2241
<212> TYPE: DNA
<213> ORGANISM: Escherichia coli
<220> FEATURE:
<221> NAME/KEY: gene
<222> LOCATION: (1)..(2241)
<223> OTHER INFORMATION: Nucleotidic sequence coding for the quimeric
      protein in the plasmid pID2

<400> SEQUENCE: 49
atgggccacc accaccacca ccacgccatg gtagataaaa gaatggcttt agttgaattg      60
aaagtgcccg acattggcgg aacagaaaat gtagatatta tcgcggttga agtaaacgtg     120
ggcgacacta ttgctgtgga cgatacccctg attactttgg atctagacaa agtccgtatg     180
gagaaattga gaatcaaggg aatgtcatac acgatgtgtt caggaaagtt ttcaattgac     240
aaagagatgg cagaaacaca gcatgggaca cagtggtga agtcaagta tgaaggtgct     300 ggagctccgt gtaaagtccc catagagata agagatgtaa acaaggaaaa agtggttggg     360
cgtatcatct catccacccc tttggctgag aataccaaca gtgtaaccaa catagaatta     420 gaaccccccct ttggggacag ctacatagtg ataggtgttg gaaacagcgc attaacactc     480
cattggttca ggaaagggag ttccattggc aagatgtttg agtccacata cagaggtgca     540
aaacgaatgg ccattctagg tgaaacagct tgggattttg gtagcgttgg tggactgaat     600
tcgatgaatt cgatggacgt acctgctgaa gttgcaggcg tagtcaaaga agttaaagtt     660
aaagtcggcg acaaaatctc tgaaggtggt ttgattgtcg tcgttgaagc tgaaggcacg     720
gcagccgctc ctaaagccga agcggctgcc gccccggcgc aagaagcccc taaagctgcc     780
gctcctgctc cgcaagccgc gcaattcggc ggttctgccg atgccgagta cgacgtggtc     840
gtattgggtg gcggtcccgg cggttactcc gctgcatttg ccgctgccga tgaaggcttg     900
aaagtcgcca tcgtcgaacg ttacaaaact ttgggcggcg tttgcctgaa cgtcggctgt     960
atcccttcca aagccttgtt gcacaatgcc gccgttatcg acgaagtgcg ccacttggct    1020
gccaacggta tcaaataccc cgagccggaa ctcgacatcg atatgcttcg cgcctacaaa    1080
gacggcgtag tttcccgcct cacgggcggt ttggcaggta tggcgaaaag ccgtaaagtg    1140
gacgttatcc aaggcgacgg gcaattctta gatccgcacc acttggaagt gtcgctgact    1200
gccggcgacg cgtacgaaca ggcagcccct accggcgaga aaaaaatcgt tgccttcaaa    1260
aactgtatca ttgcagcagg cagccgcgta accaaactgc ctttcattcc tgaagatccg    1320
cgcatcatcg attccagcgg cgcattggct ctgaaagaag taccgggcaa actgctgatt    1380 atcgcggcg gcattatcgg cctcgagatg ggtacggttt acagcacgct gggttcgcgt    1440
ttggatgtgg ttgaaatgat ggacggcctg atgcaaggcg cagaccgcga tttggtaaaa    1500
gtatggcaaa acaaaacga ataccgtttt gacaacatta tggtcaacac caaaaccgtt    1560
gcagttgagc cgaaagaaga cggcgtttac gttaccttg aaggcgcgaa cgcgcctaaa    1620

-continued

```
gagccgcaac gctacgatgc cgtattggtt gccgccggcc gcgcgcccaa cggcaaactc    1680
atcagcgcgg aaaaagcagg cgttgccgta accgatcgcg gcttcatcga agtggacaaa    1740
caaatgcgta ccaatgtgcc gcacatctac gccatcggcg acatcgtcgg tcagccgatg    1800
ttggcgcaca aagccgttca cgaaggccac gttgccgccg aaaactgcgc cggccacaaa    1860
gcctacttcg acgcacgcgt gattccgggc gttgcctaca cttcccccga agtggcgtgg    1920
gtgggcgaaa ccgaactgtc cgccaaagcc tccggccgca aaatcaccaa agccaacttc    1980
ccgtgggcgg cttccggccg tgcgattgcc aacggttgcg acaagccgtt taccaagctg    2040 attttttgatg ccgaaaccgg ccgcatcatc ggcggcggca ttgtcggtcc gaacggtggc    2100
gatatgatcg gcgaagtctg ccttgccatc gaaatgggct gcgacgcggc agacatcggc    2160
aaaaccatcc acccgcaccc gggcgaatcc atcggtatgg cggcggaagt ggcattgggt    2220
acttgtaccg acaaaaaaaa a                                              2241
```

<210> SEQ ID NO 50
<211> LENGTH: 747
<212> TYPE: PRT
<213> ORGANISM: Escherichia coli
<220> FEATURE:
<221> NAME/KEY: CHAIN
<222> LOCATION: (1)..(747)
<223> OTHER INFORMATION: Aminoacidic sequence of the PID2

<400> SEQUENCE: 50

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Thr Leu Ile
         35                  40                  45

Thr Leu Asp Leu Asp Lys Val Arg Met Glu Lys Leu Arg Ile Lys Gly
     50                  55                  60

Met Ser Tyr Thr Met Cys Ser Gly Lys Phe Ser Ile Asp Lys Glu Met
 65                  70                  75                  80

Ala Glu Thr Gln His Gly Thr Thr Val Val Lys Val Lys Tyr Glu Gly
                 85                  90                  95

Ala Gly Ala Pro Cys Lys Val Pro Ile Glu Ile Arg Asp Val Asn Lys
            100                 105                 110

Glu Lys Val Val Gly Arg Ile Ile Ser Ser Thr Pro Leu Ala Glu Asn
        115                 120                 125

Thr Asn Ser Val Thr Asn Ile Glu Leu Glu Arg Pro Leu Asp Ser Tyr
    130                 135                 140

Ile Val Ile Gly Val Gly Asn Ser Ala Leu Thr Leu His Trp Phe Arg
145                 150                 155                 160

Lys Gly Ser Ser Ile Gly Lys Met Phe Glu Ser Thr Tyr Arg Gly Ala
                165                 170                 175

Lys Arg Met Ala Ile Leu Gly Glu Thr Ala Trp Asp Phe Gly Ser Val
            180                 185                 190

Gly Gly Leu Asn Ser Met Asn Ser Met Asp Val Pro Ala Glu Val Ala
        195                 200                 205

Gly Val Val Lys Glu Val Lys Val Gly Asp Lys Ile Ser Glu
    210                 215                 220

Gly Gly Leu Ile Val Val Glu Ala Glu Gly Thr Ala Ala Ala Pro
225                 230                 235                 240

Lys Ala Glu Ala Ala Ala Ala Pro Ala Gln Glu Ala Pro Lys Ala Ala
```

```
                        245                 250                 255
Ala Pro Ala Pro Gln Ala Gln Phe Gly Gly Ser Ala Asp Ala Glu
            260                 265                 270

Tyr Asp Val Val Leu Gly Gly Pro Gly Gly Tyr Ser Ala Ala
            275                 280                 285

Phe Ala Ala Asp Glu Gly Leu Lys Val Ala Ile Val Glu Arg Tyr
290                 295                 300

Lys Thr Leu Gly Gly Val Cys Leu Asn Val Gly Cys Ile Pro Ser Lys
305                 310                 315                 320

Ala Leu Leu His Asn Ala Ala Val Ile Asp Glu Val Arg His Leu Ala
                325                 330                 335

Ala Asn Gly Ile Lys Tyr Pro Glu Pro Glu Leu Asp Ile Asp Met Leu
            340                 345                 350

Arg Ala Tyr Lys Asp Gly Val Val Ser Arg Leu Thr Gly Gly Leu Ala
            355                 360                 365

Gly Met Ala Lys Ser Arg Lys Val Asp Val Ile Gln Gly Asp Gly Gln
    370                 375                 380

Phe Leu Asp Pro His His Leu Glu Val Ser Leu Thr Ala Gly Asp Ala
385                 390                 395                 400

Tyr Glu Gln Ala Ala Pro Thr Gly Glu Lys Lys Ile Val Ala Phe Lys
                405                 410                 415

Asn Cys Ile Ile Ala Ala Gly Ser Arg Val Thr Lys Leu Pro Phe Ile
            420                 425                 430

Pro Glu Asp Pro Arg Ile Ile Asp Ser Ser Gly Ala Leu Ala Leu Lys
            435                 440                 445

Glu Val Pro Gly Lys Leu Leu Ile Ile Gly Gly Gly Ile Ile Gly Leu
    450                 455                 460

Glu Met Gly Thr Val Tyr Ser Thr Leu Gly Ser Arg Leu Asp Val Val
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
            500                 505                 510

Thr Lys Thr Val Ala Val Glu Pro Lys Glu Asp Gly Val Tyr Val Thr
            515                 520                 525

Phe Glu Gly Ala Asn Ala Pro Lys Glu Pro Gln Arg Tyr Asp Ala Val
            530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575

Gln Met Arg Thr Asn Val Pro His Ile Tyr Ala Ile Gly Asp Ile Val
            580                 585                 590

Gly Gln Pro Met Leu Ala His Lys Ala Val His Glu Gly His Val Ala
            595                 600                 605

Ala Glu Asn Cys Ala Gly His Lys Ala Tyr Phe Asp Ala Arg Val Ile
            610                 615                 620

Pro Gly Val Ala Tyr Thr Ser Pro Glu Val Ala Trp Val Gly Glu Thr
625                 630                 635                 640

Glu Leu Ser Ala Lys Ala Ser Gly Arg Lys Ile Thr Lys Ala Asn Phe
                645                 650                 655

Pro Trp Ala Ala Ser Gly Arg Ala Ile Ala Asn Gly Cys Asp Lys Pro
            660                 665                 670
```

```
Phe Thr Lys Leu Ile Phe Asp Ala Glu Thr Gly Arg Ile Ile Gly Gly
        675                 680                 685
Gly Ile Val Gly Pro Asn Gly Gly Asp Met Ile Gly Glu Val Cys Leu
        690                 695                 700
Ala Ile Glu Met Gly Cys Asp Ala Ala Asp Ile Gly Lys Thr Ile His
705                 710                 715                 720
Pro His Pro Gly Glu Ser Ile Gly Met Ala Ala Glu Val Ala Leu Gly
                725                 730                 735
Thr Cys Thr Asp Leu Pro Pro Gln Lys Lys Lys
                740                 745

<210> SEQ ID NO 51
<211> LENGTH: 2256
<212> TYPE: DNA
<213> ORGANISM: Escherichia coli
<220> FEATURE:
<221> NAME/KEY: gene
<222> LOCATION: (1)..(2256)
<223> OTHER INFORMATION: Nucleotidic sequence coding for the quimeric
      protein in the plasmid pID3

<400> SEQUENCE: 51
atgggccacc accaccacca ccacgccatg gtagataaaa gaatggcttt agttgaattg      60
aaagtgcccg acattggcgg acacgaaaat gtagatatta tcgcggttga agtaaacgtg     120
ggcgacacta ttgctgtgga cgatacccctg attactttgg atctagaaat ggacgtacct    180
gctgaagttg caggcgtagt caaagaagtt aaagttaaag tcggcgacaa aatctctgaa    240
ggtggtttga ttgtcgtcgt tgaagctgaa ggcacggcag ccgctcctaa agccgaagcg    300
gctgccgccc cggcgcaaga agcccctaaa gctgccgctc ctgctccgca agccgcgcaa    360
ttcggcggtt ctgccgatgc cgagtacgac gtggtcgtat gggtggcgg tcccggcggt      420 tactccgctg catttgccgc tgccgatgaa ggcttgaaag tcgccatcgt cgaacgttac    480
aaaactttgg gcggcgtttg cctgaacgtc ggctgtatcc cttccaaagc cttgttgcac    540
aatgccgccg ttatcgacga agtgcgccac ttggctgcca acggtatcaa ataccccgag    600
ccggaactcg acatcgatat gcttcgcgcc tacaaagacg cgtagtttc ccgcctcacg      660 ggcggtttgg caggtatggc gaaaagccgt aaagtggacg ttatccaagg cgacgggcaa    720
ttcttagatc cgcaccactt ggaagtgtcg ctgactgccg cgacgcgta cgaacaggca      780 gccccctaccg gcgagaaaaa aatcgttgcc ttcaaaaact gtatcattgc agcaggcagc    840
cgcgtaacca aactgccttt cattcctgaa gatccgcgca tcatcgattc cagcggcgca    900
ttggctctga agaagtacc gggcaaactg ctgattatcg gcggcggcat tatcggcctc    960
gagatgggta cggtttacag cacgctgggt tcgcgtttgg atgtggttga atgatggac      1020 ggcctgatgc aaggcgcaga ccgcgatttg gtaaaagtat ggcaaaaaca aaacgaatac    1080
cgttttgaca acattatggt caacaccaaa accgttgcag ttgagccgaa agaagacggc    1140
gtttacgtta cctttgaagg cgcgaacgcg cctaaagagc cgcaacgcta cgatgccgta    1200
ttggttgccg ccgccgcgc gcccaacggc aaactcatca gcgcgaaaa agcaggcgtt      1260 gccgtaaccg atcgcggctt catcgaagtg gacaaacaaa tgcgtaccaa tgtgccgcac    1320
atctacgcca tcgcgacat cgtcggtcag ccgatgttgg cgcacaaagc cgttcacgaa      1380
ggccacgttg ccgccgaaaa ctgcgccggc cacaaagcct acttcgacgc acgcgtgatt    1440
ccgggcgttg cctacactcc ccccgaagtg cgtgggtgg cgaaaccga actgtccgcc      1500 aaagcctccg ccgcaaaat caccaaagcc aacttcccgt gggcggcttc cggccgtgcg     1560
```

```
attgccaacg gttgcgacaa gccgtttacc aagctgattt ttgatgccga aaccggccgc   1620
atcatcggcg gcggcattgt cggtccgaac ggtggcgata tgatcggcga agtctgcctt   1680
gccatcgaaa tgggctgcga cgcggcagac atcggcaaaa ccatccaccc gcacccgacc   1740
ttgggcgaat ccatcggtat ggcggcgaat gtggcattgg gtacttgtac cgacctgcct   1800
ccgcaaaaga aaaaggatc caaagtgcgt atggagaaat tgagaatcaa gggaatgtca    1860
tacacgatgt gttcaggaaa gttttcaatt gacaaagaga tggcagaaac acagcatggg   1920
acaacagtgg tgaaagtcaa gtatgaaggt gctggagctc cgtgtaaagt ccccatagag   1980
ataagagatg taaacaagga aaagtggtt gggcgtatca tctcatccac ccctttggct    2040
gagaatacca acagtgtaac caacatagaa ttagaacccc cctttgggga cagctacata   2100
gtgataggtg ttggaaacag cgcattaaca ctccattggt tcaggaaagg gagttccatt   2160
ggcaagatgt ttgagtccac atacagaggt gcaaaacgaa tggccattct aggtgaaaca   2220
gcttgggatt ttggttcggt tggtggctaa ggatcc                              2256
```

<210> SEQ ID NO 52
<211> LENGTH: 744
<212> TYPE: PRT
<213> ORGANISM: Escherichia coli
<220> FEATURE:
<221> NAME/KEY: CHAIN
<222> LOCATION: (1)..(744)
<223> OTHER INFORMATION: Aminoacidic sequence of the PID3

<400> SEQUENCE: 52

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Met Asn Ser Met Asp Val Pro Ala Glu Val Ala Gly Val
     50                  55                  60

Val Lys Glu Val Lys Val Lys Val Gly Asp Lys Ile Ser Glu Gly Gly
 65                  70                  75                  80

Leu Ile Val Val Glu Ala Glu Gly Thr Ala Ala Ala Pro Lys Ala
                 85                  90                  95

Glu Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240
```

```
Asp Pro His His Leu Glu Val Ser Leu Thr Ala Gly Asp Ala Tyr Glu
            245                 250                 255

Gln Ala Ala Pro Thr Gly Glu Lys Lys Ile Val Ala Phe Lys Asn Cys
                260                 265                 270

Ile Ile Ala Ala Gly Ser Arg Val Thr Lys Leu Pro Phe Ile Pro Glu
            275                 280                 285

Asp Pro Arg Ile Ile Asp Ser Ser Gly Ala Leu Ala Leu Lys Glu Val
        290                 295                 300

Pro Gly Lys Leu Leu Ile Ile Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
            340                 345                 350

Gln Lys Gln Asn Glu Tyr Arg Phe Asp Asn Ile Met Val Asn Thr Lys
        355                 360                 365

Thr Val Ala Val Glu Pro Lys Glu Asp Gly Val Tyr Val Thr Phe Glu
    370                 375                 380

Gly Ala Asn Ala Pro Lys Glu Pro Gln Arg Tyr Asp Ala Val Leu Val
385                 390                 395                 400

Ala Ala Gly Arg Ala Pro Asn Gly Lys Leu Ile Ser Ala Glu Lys Ala
                405                 410                 415

Gly Val Ala Val Thr Asp Arg Gly Phe Ile Glu Val Asp Lys Gln Met
            420                 425                 430

Arg Thr Asn Val Pro His Ile Tyr Ala Ile Gly Asp Ile Val Gly Gln
        435                 440                 445

Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Gly Ser Lys Val Arg Met Glu
        595                 600                 605

Lys Leu Arg Ile Lys Gly Met Ser Tyr Thr Met Cys Ser Gly Lys Phe
    610                 615                 620

Ser Ile Asp Lys Glu Met Ala Glu Thr Gln His Gly Thr Thr Val Val
625                 630                 635                 640

Lys Val Lys Tyr Glu Gly Ala Gly Ala Pro Cys Lys Val Pro Ile Glu
                645                 650                 655

Ile Arg Asp Val Asn Lys Glu Lys Val Val Gly Arg Ile Ile Ser Ser
```

```
                      660                 665                 670
Thr Pro Leu Ala Glu Asn Thr Asn Ser Val Thr Asn Ile Glu Leu Glu
                675                 680                 685

Arg Pro Leu Asp Ser Tyr Ile Val Ile Gly Val Gly Asn Ser Ala Leu
            690                 695                 700

Thr Leu His Trp Phe Arg Lys Gly Ser Ser Ile Gly Lys Met Phe Glu
705                 710                 715                 720

Ser Thr Tyr Arg Gly Ala Lys Arg Met Ala Ile Leu Gly Glu Thr Ala
                725                 730                 735

Trp Asp Phe Gly Ser Val Gly Gly
            740

<210> SEQ ID NO 53
<211> LENGTH: 2694
<212> TYPE: DNA
<213> ORGANISM: Escherichia coli
<220> FEATURE:
<221> NAME/KEY: gene
<222> LOCATION: (1)..(2694)
<223> OTHER INFORMATION: Nucleotidic sequence coding for the quimeric
      protein in the plasmid pD4D2

<400> SEQUENCE: 53
atgggccacc accaccacca ccacgccatg gtagataaaa gaatggcttt agttgaattg      60
aaagtgcccg acattggcgg acacgaaaat gtagatatta tcgcggttga agtaaacgtg     120
ggcgacacta ttgctgtgga cgatacccct attactttgg atctagacaa agtccgtatg     180
gagaaattga gaatcaaggg aatgtcatac acgatgtgtt caggaaagtt ttcaattgac     240
aaagagatgg cagaaacaca gcatgggaca cagtggtgaa agtcaagta  tgaaggtgct     300 ggagctccgt gtaaagtccc catagagata agagatgtaa acaaggaaaa agtggttggg     360
cgtatcatct catccacccc tttggctgag aataccaaca gtgtaaccaa catagaatta     420 gaaccccccct tggggacag ctacatagtg ataggtgttg aaacagcgc  attaacactc     480 cattggttca ggaaagggag ttccattggc aagatgtttg agtccacata cagaggtgca     540
aaacgaatgg ccattctagg tgaaacagct tgggattttg gttccgttgg tggtcttcta     600
gaaatggacg tacctgctga agttgcaggc gtagtcaaag aagttaaagt taaagtcggc     660
gacaaaatct ctgaaggtgg tttgattgtc gtcgttgaag ctgaaggcac ggcagccgct     720
cctaaagccg aagcggctgc cgccccggcg caagaagccc taaagctgc  cgctcctgct     780 ccgcaagccg cgcaattcgg cggttctgcc gatgccgagt acgacgtggt cgtattgggt     840
ggcggtcccg gcggttactc cgctgcattt gccgctgccg atgaaggctt gaaagtcgcc     900
atcgtcgaac gttacaaaac tttggcggc  gtttgcctga cgtcggctg  tatcccttcc     960 aaagccttgt tgcacaatgc cgccgttatc gacgaagtgc gccacttggc tgccaacggt    1020
atcaaatacc ccgagccgga actcgacatc gatatgcttc gcgcctacaa agacggcgta    1080 gtttccgcc  tcacgggcgg tttggcaggt atggcgaaaa gccgtaaagt ggacgttatc    1140
caaggcgacg gcaattcttagatccgcac cacttggaag tgtcgctgac tgccggcgac    1200
gcgtacgaac aggcagcccc taccggcgag aaaaaaatcg ttgccttcaa aaactgtatc    1260
attgcagcag gcagccgcgt aaccaaactg ccttttcattc ctgaagatcc gcgcatcatc    1320
gattccagcg gcgcattggc tctgaaagaa gtaccgggca aactgctgat tatcggcggc    1380
ggcattatcg gcctcgagat gggtacggtt tacagcacgc tgggttcgcg tttggatgtg    1440
gttgaaatga tggacggcct gatgcaaggc gcagaccgcg atttggtaaa agtatggcaa    1500
```

```
aaacaaaacg aataccgttt tgacaacatt atggtcaaca ccaaaaccgt tgcagttgag   1560
ccgaaagaag acggcgttta cgttacccttt gaaggcgcga acgcgcctaa agagccgcaa   1620
cgctacgatg ccgtattggt tgccgccggc cgcgcgccca acggcaaact catcagcgcg   1680
gaaaaagcag gcgttgccgt aaccgatcgc ggcttcatcg aagtggacaa acaaatgcgt   1740
accaatgtgc cgcacatcta cgccatcggc gacatcgtcg gtcagccgat gttggcgcac   1800
aaagccgttc acgaaggcca cgttgccgcc gaaaactgcg ccggccacaa agcctacttc   1860
gacgcacgcg tgattccggg cgttgcctac acttcccccg aagtggcgtg gtgggcgaa    1920 accgaactgt ccgccaaagc ctccggccgc aaaatcacca agccaacttc ccgtgggcg    1980 gcttccggcc gtgcgattgc caacggttgc gacaagccgt ttaccaagct gattttttgat   2040 gccgaaaccg gccgcatcat cggcggcggc attgtcggtc cgaacggtgg cgatatgatc   2100
ggcgaagtct gccttgccat cgaaatgggc tgcgacgcgg cagacatcgg caaaaccatc   2160
cacccgcacc cgaccttggg cgaatccatc ggtatggcgg cggaagtggc attgggtact   2220
tgtaccgacc tgcctccgca aagaaaaaa ggatccgaca ggctgagaat ggacaaacta    2280
cagctcaaag gaatgtcata ctctatgtgt acaggaaagt ttaaaattgt gaaggaaata   2340
gcagaaacac aacatggaac aatagttatc agagtacaat atgaagggga cggctctcca   2400
tgtaagatcc ctttttgagat aatggatttg gaaaaaagac acgtcttagg tcgcctgatt   2460
acagttaacc cgatcgtaac agaaaaagat agcccagtca acatagaagc agaacctcca   2520
ttcggagaca gctacatcat cataggagta gagccgggac aattgaaact caactggttt   2580
aagaaaggaa gttccatcgg ccaaatgttt gagacaacaa tgagaggagc aagagaatg    2640 gccattttag gtgacacagc ctgggatttt gggtctctgg gtggttaagg atcc          2694
```

<210> SEQ ID NO 54
<211> LENGTH: 891
<212> TYPE: PRT
<213> ORGANISM: Escherichia coli
<220> FEATURE:
<221> NAME/KEY: CHAIN
<222> LOCATION: (1)..(891)
<223> OTHER INFORMATION: Aminoacidic sequence of the PD4D2

<400> SEQUENCE: 54

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Lys Val Arg Met Glu Lys Leu Arg Ile Lys Gly
     50                  55                  60

Met Ser Tyr Thr Met Cys Ser Gly Lys Phe Ser Ile Asp Lys Glu Met
 65                  70                  75                  80

Ala Glu Thr Gln His Gly Thr Thr Val Val Lys Val Lys Tyr Glu Gly
                 85                  90                  95

Ala Gly Ala Pro Cys Lys Val Pro Ile Glu Ile Arg Asp Val Asn Lys
            100                 105                 110

Glu Lys Val Val Gly Arg Ile Ile Ser Ser Thr Pro Leu Ala Glu Asn
        115                 120                 125

Thr Asn Ser Val Thr Asn Ile Glu Leu Glu Arg Pro Leu Asp Ser Tyr
    130                 135                 140

Ile Val Ile Gly Val Gly Asn Ser Ala Leu Thr Leu His Trp Phe Arg
```

```
                145                 150                 155                 160
Lys Gly Ser Ser Ile Gly Lys Met Phe Glu Ser Thr Tyr Arg Gly Ala
                165                 170                 175

Lys Arg Met Ala Ile Leu Gly Glu Thr Ala Trp Asp Phe Gly Ser Val
            180                 185                 190

Gly Gly Leu Leu Glu Met Asn Ser Met Asp Val Pro Ala Glu Val Ala
            195                 200                 205

Gly Val Val Lys Glu Val Lys Val Lys Val Gly Asp Lys Ile Ser Glu
            210                 215                 220

Gly Gly Leu Ile Val Val Glu Ala Glu Gly Thr Ala Ala Ala Pro
225                 230                 235                 240

Lys Ala Glu Ala Ala Ala Pro Ala Gln Glu Ala Pro Lys Ala Ala
                245                 250                 255

Ala Pro Ala Pro Gln Ala Ala Gln Phe Gly Gly Ser Ala Asp Ala Glu
                260                 265                 270

Tyr Asp Val Val Leu Gly Gly Pro Gly Gly Tyr Ser Ala Ala
                275                 280                 285

Phe Ala Ala Ala Asp Glu Gly Leu Lys Val Ala Ile Val Glu Arg Tyr
290                 295                 300

Lys Thr Leu Gly Gly Val Cys Leu Asn Val Gly Cys Ile Pro Ser Lys
305                 310                 315                 320

Ala Leu Leu His Asn Ala Ala Val Ile Asp Glu Val Arg His Leu Ala
                325                 330                 335

Ala Asn Gly Ile Lys Tyr Pro Glu Pro Glu Leu Asp Ile Asp Met Leu
                340                 345                 350

Arg Ala Tyr Lys Asp Gly Val Val Ser Arg Leu Thr Gly Gly Leu Ala
                355                 360                 365

Gly Met Ala Lys Ser Arg Lys Val Asp Val Ile Gln Gly Asp Gly Gln
            370                 375                 380

Phe Leu Asp Pro His His Leu Glu Val Ser Leu Thr Ala Gly Asp Ala
385                 390                 395                 400

Tyr Glu Gln Ala Ala Pro Thr Gly Glu Lys Lys Ile Val Ala Phe Lys
                405                 410                 415

Asn Cys Ile Ile Ala Ala Gly Ser Arg Val Thr Lys Leu Pro Phe Ile
                420                 425                 430

Pro Glu Asp Pro Arg Ile Ile Asp Ser Ser Gly Ala Leu Ala Leu Lys
                435                 440                 445

Glu Val Pro Gly Lys Leu Leu Ile Ile Gly Gly Ile Ile Gly Leu
            450                 455                 460

Glu Met Gly Thr Val Tyr Ser Thr Leu Gly Ser Arg Leu Asp Val Val
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
                500                 505                 510

Thr Lys Thr Val Ala Val Glu Pro Lys Glu Asp Gly Val Tyr Val Thr
            515                 520                 525

Phe Glu Gly Ala Asn Ala Pro Lys Glu Pro Gln Arg Tyr Asp Ala Val
            530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575
```

```
Gln Met Arg Thr Asn Val Pro His Ile Tyr Ala Ile Gly Asp Ile Val
                580             585             590

Gly Gln Pro Met Leu Ala His Lys Ala Val His Glu Gly His Val Ala
        595             600             605

Ala Glu Asn Cys Ala Gly His Lys Ala Tyr Phe Asp Ala Arg Val Ile
    610             615             620

Pro Gly Val Ala Tyr Thr Ser Pro Glu Val Ala Trp Val Gly Glu Thr
625             630             635             640

Glu Leu Ser Ala Lys Ala Ser Gly Arg Lys Ile Thr Lys Ala Asn Phe
            645             650             655

Pro Trp Ala Ala Ser Gly Arg Ala Ile Ala Asn Gly Cys Asp Lys Pro
            660             665             670

Phe Thr Lys Leu Ile Phe Asp Ala Glu Thr Gly Arg Ile Ile Gly Gly
        675             680             685

Gly Ile Val Gly Pro Asn Gly Gly Asp Met Ile Gly Glu Val Cys Leu
        690             695             700

Ala Ile Glu Met Gly Cys Asp Ala Ala Asp Ile Gly Lys Thr Ile His
705             710             715             720

Pro His Pro Gly Glu Ser Ile Gly Met Ala Ala Glu Val Ala Leu Gly
            725             730             735

Thr Cys Thr Asp Leu Pro Pro Gln Lys Lys Lys Gly Ser Arg Leu Arg
            740             745             750

Met Asp Lys Leu Gln Leu Lys Gly Met Ser Tyr Ser Met Cys Thr Gly
        755             760             765

Lys Phe Lys Ile Val Lys Glu Ile Ala Glu Thr Gln His Gly Thr Ile
        770             775             780

Val Ile Arg Val Gln Tyr Glu Gly Asp Gly Ser Pro Cys Lys Ile Pro
785             790             795             800

Phe Glu Ile Met Asp Leu Glu Lys Arg His Val Leu Gly Arg Leu Ile
            805             810             815

Thr Val Asn Pro Ile Val Thr Glu Lys Asp Ser Pro Val Asn Ile Glu
            820             825             830

Ala Glu Pro Pro Phe Gly Asp Ser Tyr Ile Ile Ile Gly Val Glu Pro
        835             840             845

Gly Gln Leu Lys Leu Asn Trp Phe Lys Lys Gly Ser Ser Ile Gly Gln
    850             855             860

Met Phe Glu Thr Thr Met Arg Gly Ala Lys Arg Met Ala Ile Leu Gly
865             870             875             880

Asp Thr Ala Trp Asp Phe Gly Ser Leu Gly Gly
            885             890
```

CHIMERIC PROTEINS THAT INDUCE EFFECTS DIRECTED AGAINST VIRUSES

CROSS-REFERENCE TO RELATED APPLICATIONS

This application is a divisional of U.S. application Ser. No. 11/705,696 filed on Feb. 13, 2007, which is a divisional of U.S. application Ser. No. 10/484,114 filed on Jun. 7, 2004, which is a U.S. National Phase Application of International Application No. PCT/CU02/00006 filed on Jul. 12, 2002, which asserts priority to Cuban Application No. CU2001/0172 filed on Jul. 16, 2001. The foregoing applications are hereby incorporated by reference in their entirety herein.

FIELD OF THE INVENTION

The present invention is related with the field of the biotechnology and the pharmaceutical industry, in particular with the obtaining of chimeric nucleotide chains which, when introduced into an expression vector, give rise to proteins able to elicit a serotype-specific humoral immune response and protection against the Dengue virus infection; quoted from now on as DEN, avoiding the effects of the serotype-specific viral immunoamplification, causing hemorrhages and clinical complications described in this type of pathology.

BACKGROUND OF THE INVENTION

The Dengue virus (DEN), is a coated virus whose lipid membrane contains two of its three structural proteins: the envelope protein (E) and the membrane protein (M). The E protein covers an icosaedric nucleocapsid composed by the third of its structural proteins, the core protein. This virus belongs to the Flaviviridae family and four different serotypes exist. Its transmission to the man is carried out through the mosquito Aedes aegypti that belongs to the Stegomia family. The disease produced in the human for this virus was considered as benign and was described as Dengue Fever or Classical Dengue (DF) until the appearance of a more serious modality and sometimes lethal, characterized by hemorrhagic fever and shock, denominated: Hemorrhagic Dengue Fever and Dengue Shock Syndrome (HDF/DSS) (Hammon WMc. New hemorrhagic fever in children in the Philippines and Thailand. Trans Assoc Physicians 1960; 73: 140-155). Several epidemiological studies have been carried out evidencing as a risk factor the sequential infection of two different viral serotypes (Kouri G P, Guzmán M G, Brave J R. Why dengue hemorrhagic fever in Cuba) 2. An integral analysis. Trans Roy Soc Trop Med Hyg 1987; 72: 821-823). This phenomenon is explained by the immuno-enhancement, which is based on an increase of the viral infection by increasing the entrance of the virus-antibody complex to the cell through the Fc receptors of the target cell (monocytes) (halstead S B. Pathogenesis of dengue: challenges to molecular biology. Science 1988; 239: 476-481).

Different technologies have been developed to produce live attenuated vaccines, but at present there exist multiple unsolved issues on the possible benefits of these vaccines, since they could revert to the virulence, viral interference and inter-genomic recombination. Alternately, recombinant antigens can be obtained as possible components of a subunit vaccine (Feighny, R., Borrous, J. and Putnak R. Dengue type-2 virus envelope protein made using recombinant baculovirus protects mice against virus challenge. Am. J. Trop. Med. Hyg. 1994. 50(3). 322-328; Deubel, V., Staropoli, I., Megret, F., et al. Affinity-purified dengue-2 virus envelope glycoprotein induces neutralizing antibodies and protective immunity in mice. Vaccine. 1997. 15, 1946-1954).

The main antigen of the virus is the envelope protein DENe. This protein is the major component of the viral surface and is thought to mediate the binding of the virus to the cellular receptor (A Heinz F X, Berge R, Tuma W et al. A topological and functional model of epitopes on the structural glycoprotein of tick-borne encephalitis virus defined by monoclonal antibodies. Virology. 1983; 126: 525). This protein has structural homology with that of the tick borne encephalitis virus (TBE) (Rey, F. A., Heinz, F. X., Mandl, C., et al. The envelope glycoprotein from tick borne encephalitis virus at 2 A° resolution. Nature 1995; 375: 291-298) and it is also structurally conserved among serotypes.

The insect cells constitute one of the systems most used for the expression of diverse heterologous genes that employ the baculovirus system as vectors. These vectors have been used for the expression of several combinations of structural and nonstructural proteins of the Encephalitis Japanese virus (JEV), DEN-1, DEN-2 and DEN-4, (Matsuura Y, Miyamoto M, Soto T et al. Characterization of japanese encephalitis virus envelope protein expressed by recombinant baculoviruses. Virology 1989; 173: 677-682; Deubel V, Bordier M, Megret F et al. Processing, secretion and immunoreactivity of carboxy terminally truncated dengue-2 envelope proteins expressed in insect cell by recombinant baculoviruses. Virology 1991; 180: 440-447; Putnak R, Feighny R, Burrous J et al. Dengue 1 virus envelope glycoprotein gene expressed in recombinant baculovirus elicit virus neutralization antibodies in mice and protects them from virus challenge. Am J Trop Med Hyg 1991; 45: 159-167; Feighny R, Burrous J, Putnak R. Dengue type 2 virus envelope protein made using recombinant baculovirus protects mice against virus challenge. Am J Trop Med Hyg 1994; 50: 322-328). Another system used has been the cells of Drosophila melanogaster expressing different variants of the E protein (PCT/US96/07627). In spite of obtaining an appropriate functional response, upon using the proteins expressed in these systems, they imply a high cost for the development of scale-up production processes; therefore, the expression in yeast has been an alternative to produce recombinant structural proteins of flavivirus. However, in the case of the DENe protein, expressed in Pichia pastoris (PCT/US96/07627; Sugrue R. J., Fu H., Howe J., Chan Y. Expression of the Dengue virus structural proteins in Pichia pastoris leads to the generation of virus-like particles. J Virol. 1997. 78, 1861-1866), the levels of expression are low, either secreted or intracellularly, hindering the purification process.

In parallel, several variants of the DENe protein have been obtained in bacteria. One of them was the C-terminal portion of the E protein of the JEV fused to a protein of the Tryptophan metabolism (TrpE) of E. coli. This protein was produced as inclusion bodies and was recognized by neutralizing monoclonal antibodies (Mabs) using immunodetection techniques. However, pure preparations of this protein were unable to develop neutralizing antibodies and to protect against viral challenge (Mason P. W., Zogel M. V., Semproni A. R., et al. The antigenic structure of dengue type 1 virus envelope and NS1 protein expressed in E. coli. J Gen Virol. 1990. 71: 2107-2114). In addition, another construction was made (Srivastava A. K., Morita K., Matsuo S., et al. Japanese encephalitis virus fusion protein with protein A expressed in E. coli confers protection in mice. Microbiol Immunol. 1991. 35: 863-870), that contains the protein A of Staphylococcus aurius fused to the C-terminal fragment of the E protein, followed by the N-terminal segment of the nonstructural protein of the JEV, the NS1. In this case the fused protein was soluble, facilitating its purification by affinity chromatography. Upon immunizing mice with this pure protein high neutralizing antibodies titers were obtained, which also inhibited haemagglutination and protected against the viral challenge with the JEV. Similar results were obtained using the DENe region of the DEN-2 fused to the protein A of *S. aureus* (Srivastava A. K., Putnak R. J., Warren R. L., Hoke C. H. Mice immunized with a dengue type 2 virus E and NS1 fusion protein made in *Escherichia coli* are protected against lethal dengue virus infection. Vaccine. 1995. 13: 1251-1258); however, it is not possible to use these preparations in humans due to the presence of the protein A, which has shown a high affinity for the human immunoglobulin G (IgG). Finally, it has been reported a fusion protein that contains the B domain of the DENe protein of DEN-2 and the maltose binding protein (MBP) of *E. coli* (Simmons M., Nelson W. M., Wu S. J., Hayes C. G. Evaluation of the protective efficacy of a recombinant dengue envelope B domain fusion protein against dengue 2 virus infection in mice. Am J Trop Med Hyg. 1998. 58: 655-662) denominated MBP-DomB. This protein variant was immunogenic in mice and elicited neutralizing antibodies.

SUMMARY OF THE INVENTION

In our case, the subject of this invention relies on the obtaining of chimeric sequences, as for instance, in the first case, the sequence coding for a region of the DENe protein linked to the N-terminal fragment of a mutated protein with dehydrogenase activity (MDH) from *Neisseria meningitidis*; in the second case, the sequence coding for a region of the DENe protein linked to the entire gene of the MDH protein in two different positions, and in the third case, the chimeric sequences are formed by two fragments of the DENe protein from two different viral serotypes fused to the same gene coding for the MDH protein. These chimeric chains when inserted into a suitable vector, give rise to insoluble chimeric proteins within the bacterium's cytoplasm. These proteins are then capable to elicit high levels of neutralizing antibodies against DEN, inhibitors of the viral hemagglutination and to protect immunized mice against viral challenge.

With regards to the insolubility of the aforementioned proteins, an easy scale-up folding process was achieved in vitro, as well as the expression and purification processes which were superior to those used by Simmons et al, 1998. On the other hand, the serotype specificity of the antibodies is demonstrated, generated by immunization of mice with these proteins, at the level of neutralization, inhibition of hemaglutination and ELISA, using doses lower than those employed by Simmons et al, 1998. This fact constitutes the first report on the expression of insoluble DENe proteins in *E. coli* capable of stimulating a functional immune response.

In addition, considering the results obtained with the dimeric variant, it is possible to generate serotype-specific antibodies with the same molecule for two different viral serotypes, capable of neutralizing viral infection and protect mice against viral challenge. Concerning the MDH protein, a search for homology with other sequences was done in the EMBL data base, revealing that the first 110 amino acids are highly similar to the lipoic binding domain region and the flexible hinge of the dihydrolipoamide acetyltransferase (E2 enzyme of the pyruvate dehydrogenase complex and α-cetoglutarate dehydrogenase), and the rest of the protein is highly similar to the lipoamide dehydrogenase (LPDH), enzyme E3 of said complexes (Stephens, P. E; H. M. Darlinson, and J. R. Guest., 1983. The Pyruvate dehydrogenase complex of *E. coli*. Eur. J. Biochem. 133: 155-162.

On the other hand, it was also found that patients with Primary Biliary Cirrhosis (PBC) produced anti-mitochondrial autoantibodies, specific for the lipoic acid binding site, common among these proteins (Gershwin M E, Mackay I R, Sturgess A, Coppel R L. Identification and specificity of a cDNA encoding the 70 KDa mitochondrial antigen recognized in primary biliary cirrhosis. J Immunol 1987; 138: 3525-31). Therefore, we decided to mutate this region within the protein to avoid any autoimmune response when immunized in humans as chimeric proteins. The mutated MDH protein of our invention was used in a Phase I clinical trial and showed to be safe and immunogenic in humans, and also was not recognized by sera of patients with PBC (Pérez, A., F. Dickinson, Z. Cinza, A. Ruíz, T. Serrano, J. Sosa, S. González, Y. Gutiérrez, C. Nazábal, O. Gutiérrez, D. Guzmán, M. Díaz, M. Delgado, E. Caballero, G. Sardiñas, A. Alvarez, A. Martín, G. Guillén, R. Silva. Safety and preliminary immunogenicity of the recombinant outer membrane protein of *Neisseria meningitidis* in human volunteers. Biotech. Appl. Biochem. 34: 121-125). However, the possible use of the MBP in humans has not been demonstrated yet (Simmons M., Nelson W. M., Wu S. J., Hayes C. G. Evaluation of the protective efficacy of a recombinant dengue envelope B domain fusion protein against dengue 2 virus infection in mice. Am J Trop Med Hyg. 1998. 58: 655-662).

DETAILED DESCRIPTION OF THE INVENTION

In this invention is described the obtaining of chimeric nucleotide chains that when introduced into an expression vector, give rise to chimeric proteins capable of inducing a serotype-specific humoral immune response and protecting against the infection by Dengue virus, as for instance, the sequence coding for a region of the DENe protein from each one of the viral serotypes of the Dengue virus, linked to the N-terminal fragment of a mutated protein with dehydrogenase activity (MDH) from *Neisseria meningitidis*; in the second case, the sequence coding for a region of the DENe protein linked to the entire gene of the MDH protein in two different positions: within one site of the sequence coding for the structural domain of the MDH protein (lipoic acid binding domain and the 3' end of the gen), and in the third case, the chimeric sequences are formed by two fragments of the DENe protein from two different viral serotypes, DEN-2 and DEN-4, in two different positions of the MDH gen: one within a particular site of the sequence coding for the lipoic acid binding domain (serotype 4) and the other in the 3' end of the MDH gen (serotype 2). This was called a dimeric construct.

This chimeric proteins were obtained insoluble within the bacterium's cytoplasm. A purification process by immobilized metal affinity chromatography (IMAC) was done, which led to obtain pure proteins for immunogenicity studies.

When antigenicity results were analyzed a strong recognition of all the recombinant chimeric proteins for the hyperimmune ascitic liquids (HMAF) anti-DEN was demonstrated, being higher for the case of the fusion to the entire MDH gene, which evidences a positive effect on the folding of the region from the DENe protein given by the MDH. In the cases where the serotype 2 was used, all recombinant proteins obtained were recognized by a serotype-specific neutralizing antibody (3H5), being also higher for the case of the fusion to the entire MDH gene, as well as in the dimeric protein. It was also observed that the recognition for the HMAF from the homologous serotype in each case was significantly higher than the recognition for the HMAF from the heterologous serotypes, evidencing the exposure of serotype-specific epitopes and permitting thus its use as a diagnostic mean for Dengue and serotyping.

When all the recombinant chimeric proteins were immunized in mice a neutralizing and protective response was obtained. Highest neutralizing titers were obtained with the sequences fused to the entire gene of the MDH and with the dimeric protein, independently of the position of the fragment from the DENe protein. This showed an immunopotentiator effect of the immune response mediated by the MDH that can be explained by the influence in the folding of the DENe protein reflected in the antigenicity results obtained. It was also demonstrated for the first time, and contrary to the previous state of the art, that the insolubility of these proteins do not affect the capacity of generating a suitable immune response.

The immune response produced in all the cases was serotype-specific (antibodies against the immunized homologous serotype) in the viral neutralization, the hemoagglutination inhibition and ELISA. The generation of serotype-specific antibodies means that they are not capable to recognize antigenic determinants from virus of heterologous serotypes that favour the immunoenhacement phenomenum. This characteristic is of great importance for the development of a vaccine candidate against the Dengue virus since the recognition of antibodies to heterologous serotypes could be one of the causes for the Hemorrhagic Dengue Fever (HDF).

Besides it was showed the induction of antibodies against two viral serotypes after immunization with just one of the chimeric proteins, which permits the formulation of a vaccine candidate against the four serotypes, using only two of our available recombinant chimeric proteins.

The obtaining of the mutant MDH protein consisted of the elimination of the lipoic acid binding site in the sequence ETDKAT, based on the covalent binding of this fatty acid with the epsilon-amine groups of lysine (K) (Tuaillon N, Andre C, Briand J P et al. A lipoyl synthetic octadecapeptide of dihydrolipoamide acetyltransferase specifically recognized by anti-M2 autoantibodies in Primary Biliary Cirrhosis. J Immunol 1992; 148:445-50).

The mutagenesis was done by using PCR with a pair of primers to amplify the N-terminal region (from the start codon of the lpdA gene until the lipoic acid binding site, 135 bp) and the C-terminal of the protein (from the lipoic acid binding site until the 3' end of the gene); thus, being eliminated the possibility to generate autoimmune reactions, as demonstrated in the human clinical trials.

Deposit of the Biological Material

Plasmids PLL1, PLL2, PLL3, PLH1, PLH2, PLH3, PAZ1, PAZ2, PAZ3, PID1, PID2 and PID3 were deposited according to the Budapest Treaty in the Belgian Coordinated collection of Microorganism—BCCM™, LMBP-COLLECTION, on Jun. 20, 2003 and under the access numbers LMBP 4564, LMBP 4565, LMBP 4566, LMBP 4561, LMBP 4562, LMBP 4563, LMBP 4555, LMBP 4556, LMBP 4557, LMBP 4558, LMBP 4559, LMBP 4560, respectively.

DESCRIPTION OF FIGURES

FIG. 1. Cloning strategy of the E2 fragment to obtain PLL1.

DENe2: Fragment of the envelope protein of DEN-2.

N-term: Nucleotide sequence that codifies for the first 45 amino acids of the MDH protein.

FIG. 2. Cloning strategy of the E2 fragment to obtain PLL2.

DENe2: Fragment of the envelope protein of DEN-2.

MDH: dehydrogenase mutant.

FIG. 3. Cloning strategy of the E2 fragment to obtain PLL3.

DENe2: Fragment of the envelope protein of DEN-2.

MDH: dehydrogenase mutant.

FIG. 4. Cloning strategy of the E1 fragment to obtain PLH1.

DENe1: Fragment of the envelope protein of DEN-1.

N-term: Nucleotide sequence that codifies for the first 45 amino acids of the MDH protein.

FIG. 5. Cloning strategy of the E1 fragment to obtain PLH2.

DENe1: Fragment of the envelope protein of DEN-1.

N-term: Nucleotide sequence that codifies for the first 45 amino acids of the MDH protein.

FIG. 6. Cloning strategy of the E1 fragment to obtain PLH3.

DENe1: Fragment of the envelope protein of DEN-1.

MDH: dehydrogenase mutant.

FIG. 7. Cloning strategy of the E3 fragment to obtain PAZ1.

DENe3: Fragment of the envelope protein of DEN-3.

N-term: Nucleotide sequence that codifies for the first 45 amino acids of the MDH protein.

FIG. 8. Cloning strategy of the E3 fragment to obtain PAZ2.

DENe3: Fragment of the envelope protein of DEN-3.

MDH: dehydrogenase mutant.

FIG. 9. Cloning strategy of the E3 fragment to obtain PAZ3.

DENe3: Fragment of the envelope protein of DEN-3.

MDH: dehydrogenase mutant.

FIG. 10. Cloning strategy of the E4 fragment to obtain PID1.

DENe4: Fragment of the envelope protein of DEN-4.

N-term: Nucleotide sequence that codifies for the first 45 amino acids of the MDH protein.

FIG. 11. Cloning strategy of the E4 fragment to obtain PID2.

DENe4: Fragment of the envelope protein of DEN-4.

MDH: dehydrogenase mutant.

FIG. 12. Cloning strategy of the E4 fragment to obtain PID3.

DENe4: Fragment of the envelope protein of DEN-4.

MDH: dehydrogenase mutant.

FIG. 13. Cloning strategy to obtain PD4D2.

DENe4: Fragment of the envelope protein of DEN-4.

DENe2: Fragment of the envelope protein of DEN-2.

MDH: dehydrogenase mutant.

EXAMPLES

Example 1

Obtaining of PLL1

The nucleotide sequence that codifies for the amino acids from 286 to 426 of the envelope protein from the DEN-2 virus (Sec. Id. No. 22) was amplified with the oligonucleotides identified in the list of sequences as Sequence No. 1 and Sequence No. 2 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988. 165:234-244).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 (Hill C. W., Harnish B. W. 1982. Transposition of a chromosomal segment bounded by redundant rRNA genes in *Escherichia coli*. J Bacteriology. 149:449-457) were transformed with the selected clone, called pLL1 (FIG. 1 and Sequence No. 24). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-2 virus. The protein was recognized in Immunoblotting by polyclonal antibodies (PA) anti-DEN-2 contained in the HMAF. This protein was denominated PLL1 (Sequence No. 25).

Example 2

Purification of the PLL1 Protein

The biomass obtained from the *E. coli* strain transformed with pLL1 and grown at 37° C. was disrupted by French press. The recombinant protein was obtained preponderantly as insoluble form associated to the pellet of the cellular disruption. From the pellet the protein was extracted with urea 6 M and the supernatant, containing the PLL1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazole 50 mM and the obtained volume was loaded onto a G-25 column to finally obtain the protein in the formulation buffer NaCl 100 mM, $KCl_2$ 2 mM, $Na_2HPO_4$ 10 mM, pH 7.2, $KH_2PO_4$ 1 mM (PBS). This preparation was used for immunological studies.

Example 3

Antigenic Characterization of PLL1

The purified fraction of PLL1 was characterized either by its recognition by different polyclonal sera and/or murine monoclonal antibodies, as well as by positive human sera to Dengue (table 1).

TABLE 1

Reactivity of PLL1 protein to monoclonal and polyclonal antibodies.

| Abs** | Specificity*** | PLL1* |
|---|---|---|
| HMAF | DEN-1 | + |
| HMAF | DEN-2 | ++ |
| HMAF | DEN-3 | − |
| HMAF | DEN-4 | − |
| HMAF | EEE | − |
| HMAF | YFV | − |
| HMAF | SLV | − |
| Mab 3H5 | NT | + |

*A total of 10 µg of purified PLL1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

The highest recognitions in Dot blotting were obtained with the HMAF anti-DEN-2. This result coincides with the fact that the cloned region belongs to serotype 2. The recognition by HMAF against the other serotypes was less than in the case of serotype 2, in decreasing order: DEN-1, DEN-3 and DEN-4. The antibodies generated by other flavivirus like the Yellow Fever virus and the Saint Louis Encephalitis virus had not any recognition at all. On the other hand, the Mab 3H5 had reactivity indeed. This recognition by Western blotting relied on disulphide bond since when the sample was reduced the signal was lost. Finally, the reactivity against three human sera of high titers and three of low titers against DEN-2 was measured, achieving a substantial signal in both cases by Western blotting and Dot blotting.

Example 4

Characterization of the Antibody Response Generated by PLL1

A total of 25 Balb/c mice were i.p immunized with 35 ug of purified PLL1 in Freund adjuvant; 10 animals were bled after four doses and the antibodies anti-DEN were evaluated by ELISA. High antibody titers against DEN-2 were obtained while, no reactivity was obtained against the rest of the serotypes (table 2 and table 5). In addition, the hemagglutination inhibition assay (HIA) was done and only positive titers were found against DEN-2 (table 3 and table 5). Finally, the in vitro neutralization assay was done and neutralization titers of 1:320 against DEN-2 were obtained. However, no neutralization of the viral infection was found against the rest of the serotypes (table 4 and table 5). These results indicate the high serotype-specificity of the antibodies elicited by PLL1.

TABLE 2

Antibody titers against DEN-2 from the sera obtained upon immunization of mice with PLL1.

| Mouse | Titers anti-DEN-2 PLL1 | Titers anti-DEN-2 PBSControl (—) |
|---|---|---|
| 1 | 1/128 000 | <1:100 |
| 2 | 1/64 000 | <1:100 |
| 3 | 1/64 000 | <1:100 |
| 4 | 1/128 000 | <1:100 |
| 5 | 1/32 000 | <1:100 |
| 6 | 1/32 000 | <1:100 |
| 7 | 1/64 000 | <1:100 |
| 8 | 1/32 000 | <1:100 |
| 9 | 1/128 000 | <1:100 |
| 10 | 1/512 000 | <1:100 |

TABLE 3

Titers by HI of the sera from the animals immunized with PLL1.

| Mouse | Titers by HI* anti-DEN-2 PLL1 | Titers by HI anti-DEN-2 PBS C (—) |
|---|---|---|
| 1 | <1:5 | <1:5 |
| 2 | >1:640 | <1:5 |
| 3 | 1:320 | <1:5 |
| 4 | 1:320 | <1:5 |
| 5 | >1:640 | <1:5 |
| 6 | >1:640 | <1:5 |
| 7 | >1:640 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 4

Viral neutralization assay with the sera of animals immunized with PLL1.

| Mouse | Neutralizing titers* anti-DEN-2 PLL1 | Neutralizing titers anti-DEN-2 PBS C (—) |
|---|---|---|
| 1 | 1:320 | <1:5 |
| 2 | 1:320 | <1:5 |
| 3 | 1:320 | <1:5 |
| 4 | 1:320 | <1:5 |
| 5 | 1:80 | <1:5 |
| 6 | 1:160 | <1:5 |
| 7 | 1:320 | <1:5 |
| 8 | 1:40 | <1:5 |
| 9 | 1:160 | <1:5 |
| 10 | 1:320 | <1:5 |

*The neutralizing titers were defined as the highest dilution of serum having 50% reduction of the number of viral plaques.

TABLE 5

Cross-reactivity assay against all the viral serotypes by ELISA, HI and viral neutralization with the sera of animals immunized with PLL1.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PLL1) | <1/100 | >1:128 000 | <1/100 | <1/100 |
| 2 (PLL1) | <1/100 | 1:128 000 | <1/100 | <1/100 |

| Mixture of sera* | HI**anti-DEN-1 | HI anti-DEN-2 | HI anti-DEN-3 | HI anti-DEN-4 |
|---|---|---|---|---|
| PLL1 | <1/5 | >1/320 | <1/5 | <1/5 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PLL1) | <1:5 | 1:320 | <1:5 | <1:5 |
| 2 (PLL1) | <1:5 | 1:160 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 5

Obtaining of PLL2

The nucleotide sequence that codifies for the amino acids from 286 to 426 of the envelope protein from the DEN-2 virus (Sec. Id. No. 22) was amplified with the oligonucleotides identified in the list of sequences as Sequence No. 1 and Sequence No. 3 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988. 165:234-244).

Figure 2:
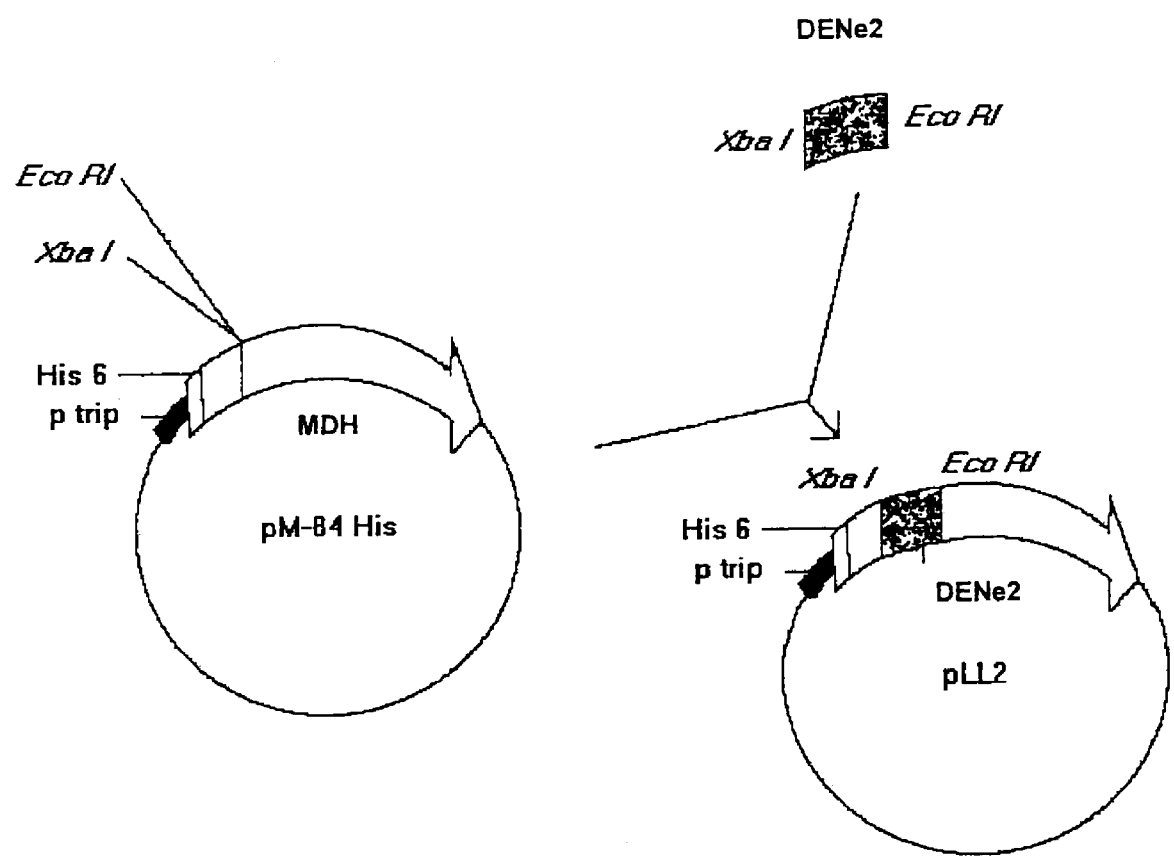

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 (Hanahan D. 1983. Studies on transformation of Escherichia coli with plasmids. J. Mol. Biol. 166:557-580) were transformed with the selected clone, called pLL2 (FIG. 2 and Sequence No. 27). Upon growing the colony in LB medium, a SDS-PAGE of the cellular lysate was done. As a result a 80 kDA band was obtained, which accounted for 10% of the total cellular proteins. The size of the protein obtained corresponded to the sum of the size of the MDH protein and the DENe protein fragment from the DEN-2 virus. The protein was recognized in Immunoblotting by a HMAF anti-DEN-2 and was denominated PLL2 (Sequence No. 28).

Example 6

Purification of the PLL2 Protein

The biomass obtained from the E. coli strain transformed with pLL2 and grown at 37° C. was disrupted by French press. The recombinant protein was obtained in both forms: soluble and insoluble. From the soluble fraction a metal ions-affinity chromatography was done using the Chelating-sepharose FF column previously coupled with $Cu^{++}$ ions. The column was washed using Imidazolee 15 mM and the protein was eluted with Imidazolee 100 mM. On the other hand, the protein associated to the insoluble fraction was extracted using Urea 8 M, and the supernatant, containing the PLL2 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 100 mM. Finally, the pure fraction of each form of the protein were loaded onto a G-25 column to obtain the protein in the formulation buffer NaCl 100 mM, $KCl_2$ 2 mM, $Na_2HPO_4$ 10 mM, pH 7.2, $KH_2PO_4$ 1 mM (PBS). This preparations were used for immunological studies.

Example 7

Antigenic Characterization of PLL2

The purified fraction of PLL2 was characterized either by its recognition by different polyclonal sera and/or murine monoclonal antibodies, as well as by positive human sera to Dengue (table 6).

The highest recognitions in Dot blotting were obtained with the HMAF anti-DEN-2. The recognition by HMAF against the other serotypes was less than in the case of serotype 2, in decreasing order: DEN-1, DEN-3 and DEN-4. The antibodies generated by other flavivirus like the Yellow Fever virus and the Saint Louis Encephalitis virus had not any recognition at all. Nevertheless, related to the Mab 3H5, a great reactivity was observed (even higher than those obtained with the PLL1) either by Dot blot and Western blot. Contrariously to the PLL1 results, the recognition with the Mab 3H5 was the same when the reducing agents are present in the sample, indicating a possible conformational difference between both proteins. Finally, the reactivity against three human sera of high titers and three of low titers against DEN-2 was measured, achieving a substantial signal in both cases by Western blotting and Dot blotting.

TABLE 6

Reactivity of PLL2 protein to monoclonal and polyclonal antibodies.

| Abs** | Specificity*** | PLL2 sol, ins* |
|---|---|---|
| HMAF | DEN-1 | ++ |
| HMAF | DEN-2 | +++ |
| HMAF | DEN-3 | − |
| HMAF | DEN-4 | − |
| HMAF | EEE | − |
| HMAF | YFV | − |
| HMAF | SLV | − |
| Mab 3H5 | NT | +++ |

*A total of 10 μg of purified PLL2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 8

Characterization of the Antibody Response Generated by PLL2

A total of 25 Balb/c mice were i.p immunized with 35 ug of purified PLL2 in Freund adjuvant; 10 animals were bled after four doses and the antibodies anti-DEN were evaluated by ELISA. High antibody titers against DEN-2 were obtained while, no reactivity was obtained against the rest of the serotypes (table 7 and table 10). In addition, the hemagglutination inhibition assay (HI) was done and only positive titers were found against DEN-2 (table 8 and table 10). Finally, the in vitro neutralization assay was done and neutralization titers of 1:1280 against DEN-2 were obtained. Similarly to the results obtained with PLL1, no neutralization of the viral infection was found against the rest of the serotypes (table 9 and table 10). On the other hand, the results obtained with both variants of PLL2 were similar, indicating that the solubility status of the protein do not influence in the capacity of generating functional antibodies.

TABLE 7

Antibody titers against DEN-2 from the sera obtained upon immunization of mice with PLL2 soluble and insoluble.

| | Titers anti-DEN-2 (PLL2) | | Titers anti-DEN-2 |
|---|---|---|---|
| Mouse | PLL2 s | PLL2 ins | PBS C (—) |
| 1 | >1:128 000 | 1:64000 | <1:100 |
| 2 | 1:128 000 | >1:128 000 | <1:100 |
| 3 | >1:128 000 | 1:128 000 | <1:100 |
| 4 | >1:128 000 | >1:128 000 | <1:100 |
| 5 | 1:64 000 | >1:128 000 | <1:100 |
| 6 | >1:128 000 | 1:128 000 | <1:100 |
| 7 | 1:64000 | >1:128 000 | <1:100 |
| 8 | >1:128 000 | 1:64000 | <1:100 |
| 9 | >1:128 000 | 1:64000 | <1:100 |
| 10 | 1:128 000 | >1:128 000 | <1:100 |

TABLE 8

Titers by HI of the sera from the animals immunized with PLL2 soluble and insoluble.

| | Titers by HI* anti-DEN-2 (PLL2) | | Titers by HI anti-DEN-2 |
|---|---|---|---|
| Mouse | PLL2 s | PLL2 ins | PBS C(—) |
| 1 | >1:640 | >1:640 | <1:5 |
| 2 | >1:640 | >1:640 | <1:5 |
| 3 | 1:320 | >1:640 | <1:5 |
| 4 | >1:640 | 1:320 | <1:5 |
| 5 | 1:320 | <1:5 | <1:5 |
| 6 | >1:640 | >1:640 | <1:5 |
| 7 | >1:640 | 1:320 | <1:5 |
| 8 | <1:5 | 1:320 | <1:5 |
| 9 | 1:320 | >1:640 | <1:5 |
| 10 | >1:640 | >1:640 | <1:5 |

*The HI titers were defined as the highest dilution capable of inhibiting the hemagglutination of goose's erythrocytes against 8 hemagglutination viral units.

TABLE 9

Viral neutralization assay with the sera of animals immunized with PLL2 soluble and insoluble.

| | Neutralizing titers* anti-DEN-2 (PLL2) | | Neutralizing titers anti-DEN-2 |
|---|---|---|---|
| Mouse | PLL2 s | PLL2 ins | PBS C(—) |
| 1 | >1:1280 | >1:1280 | >1:1280 |
| 2 | >1:1280 | >1:1280 | <1:5 |
| 3 | >1:1280 | 1:640 | <1:5 |
| 4 | 1:640 | >1:1280 | <1:5 |
| 5 | 1:640 | 1:640 | <1:5 |
| 6 | >1:1280 | >1:1280 | <1:5 |
| 7 | >1:1280 | >1:1280 | <1:5 |
| 8 | >1:1280 | >1:1280 | <1:5 |
| 9 | >1:1280 | >1:1280 | <1:5 |
| 10 | >1:1280 | >1:1280 | <1:5 |

*The neutralizing titers were defined as the highest dilution of serum having 50% reduction of the number of viral plaques.

TABLE 10

Cross-reactivity assay against all the viral serotypes by ELISA, HI and viral neutralization with the sera of animals immunized with PLL2 soluble and insoluble.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLL2 sol.) | <1/100 | >1:128 000 | <1/100 | <1/100 |
| 2 (PLL2 sol.) | <1/100 | 1:64000 | <1/100 | <1/100 |
| 1 (PLL2 ins.) | <1/100 | 1:64000 | <1/100 | <1/100 |
| 2 (PLL2 ins.) | <1/100 | >1:128 000 | <1/100 | <1/100 |
| Mixture of sera* | HI**anti-DEN-1 | HI anti-DEN-2 | HI anti-DEN-3 | HI anti-DEN-4 |
| PLL2 sol. | <1/5 | >1/320 | <1/5 | <1/5 |
| PLL2 ins. | <1/5 | >1/320 | <1/5 | <1/5 |

TABLE 10-continued Cross-reactivity assay against all the viral serotypes by ELISA, HI and viral neutralization with the sera of animals immunized with PLL2 soluble and insoluble.

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PLL2) | <1:5 | 1:320 | <1:5 | <1:5 |
| 2 (PLL2) | <1:5 | 1:160 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 9

Obtaining of pLL3

The nucleotide sequence that codifies for the amino acids from 286 to 426 of the envelope protein from the DEN-2 virus (Sec. Id. No. 22) was amplified with the oligonucleotides identified in the list of sequences as Sequence No. 4 and Sequence No. 5 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988. 165:234-244).

Figure 3:
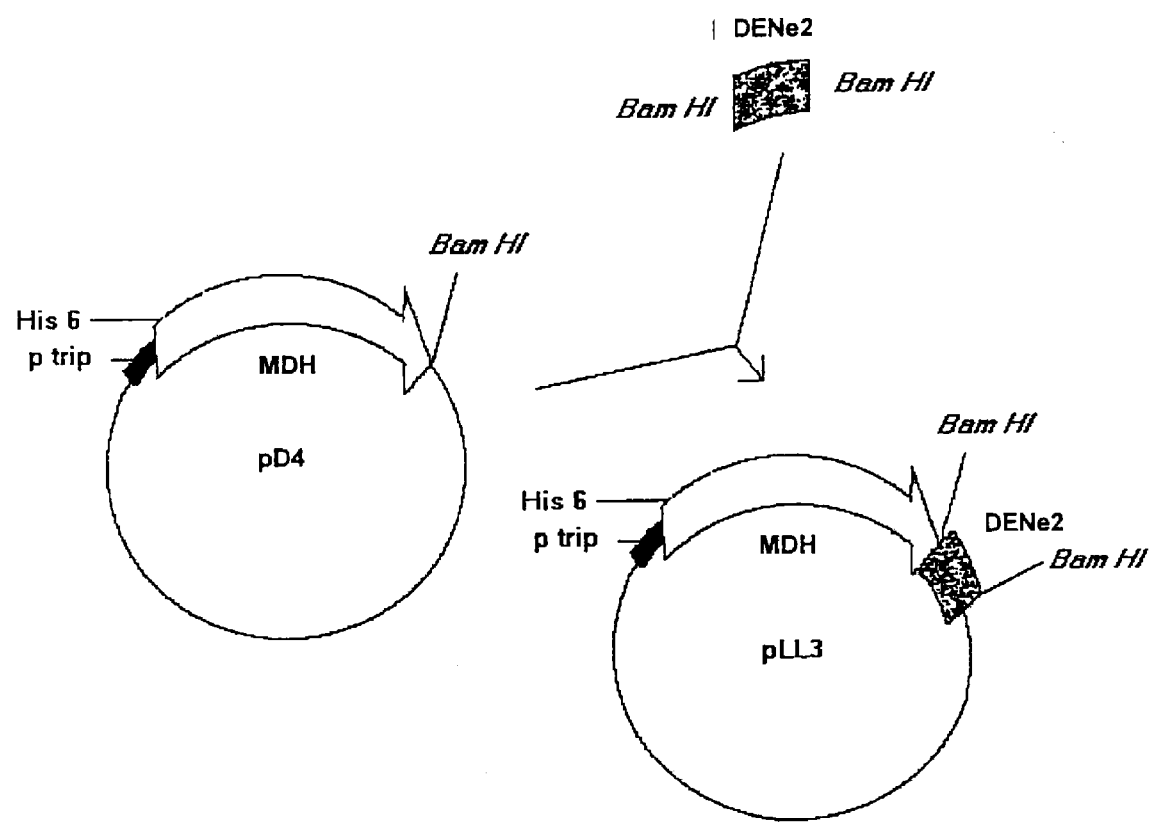
Figure 4:
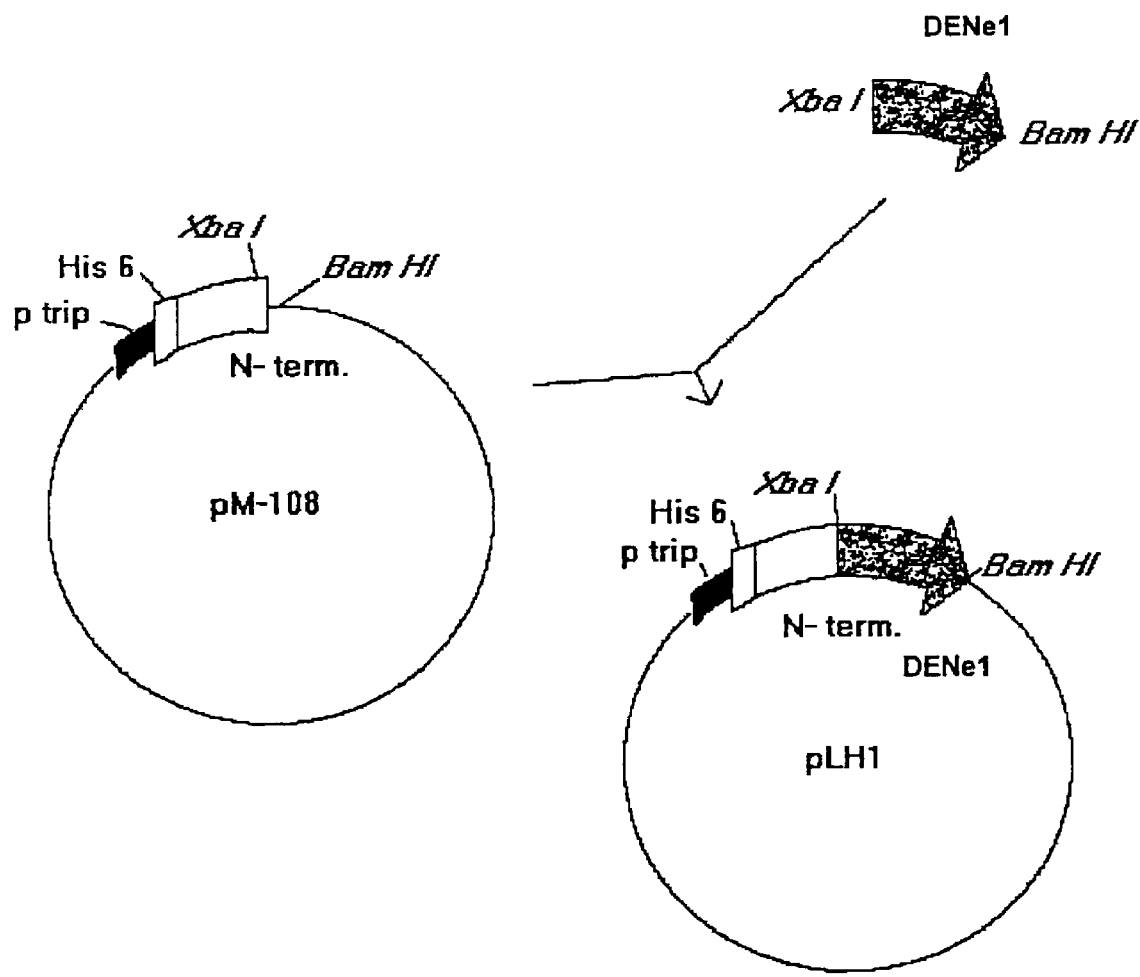
Figure 5:
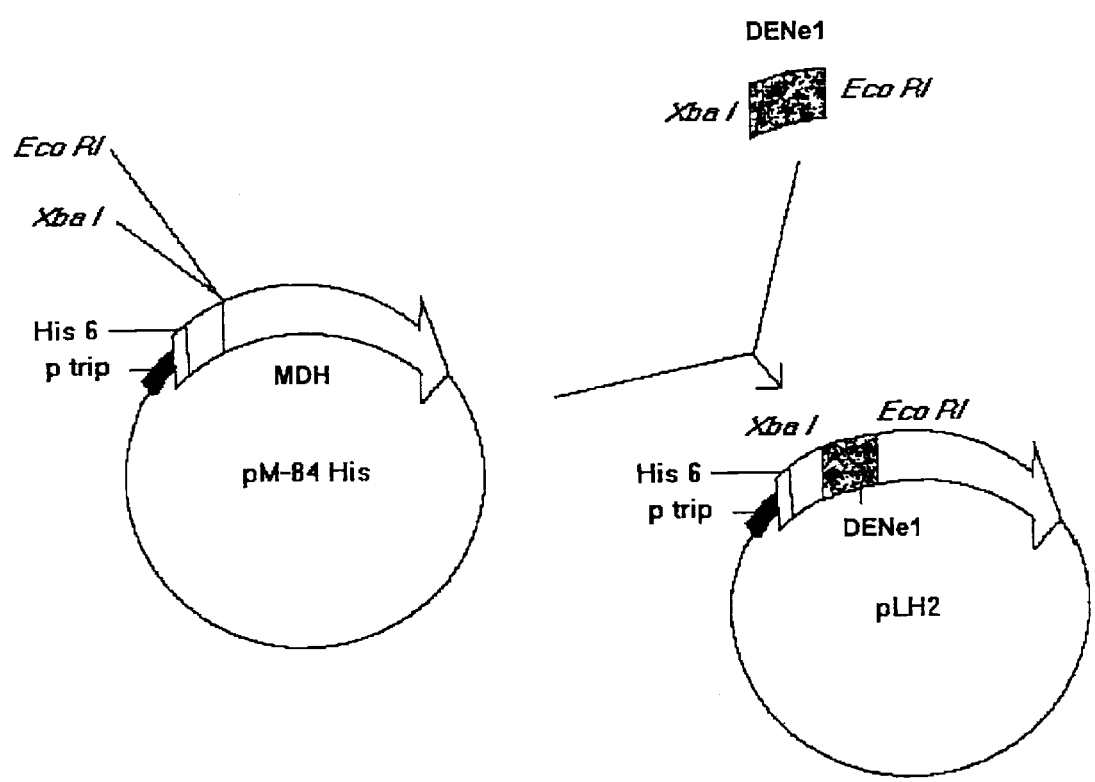
Figure 6:
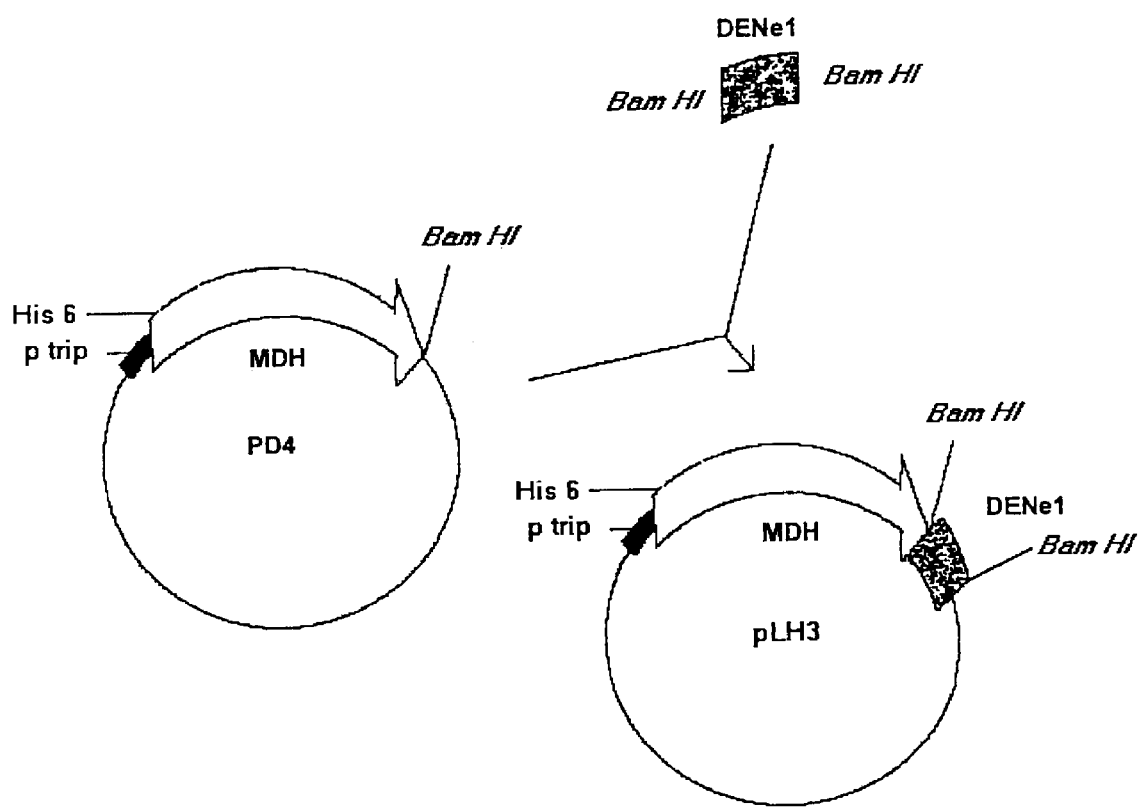
Figure 7:
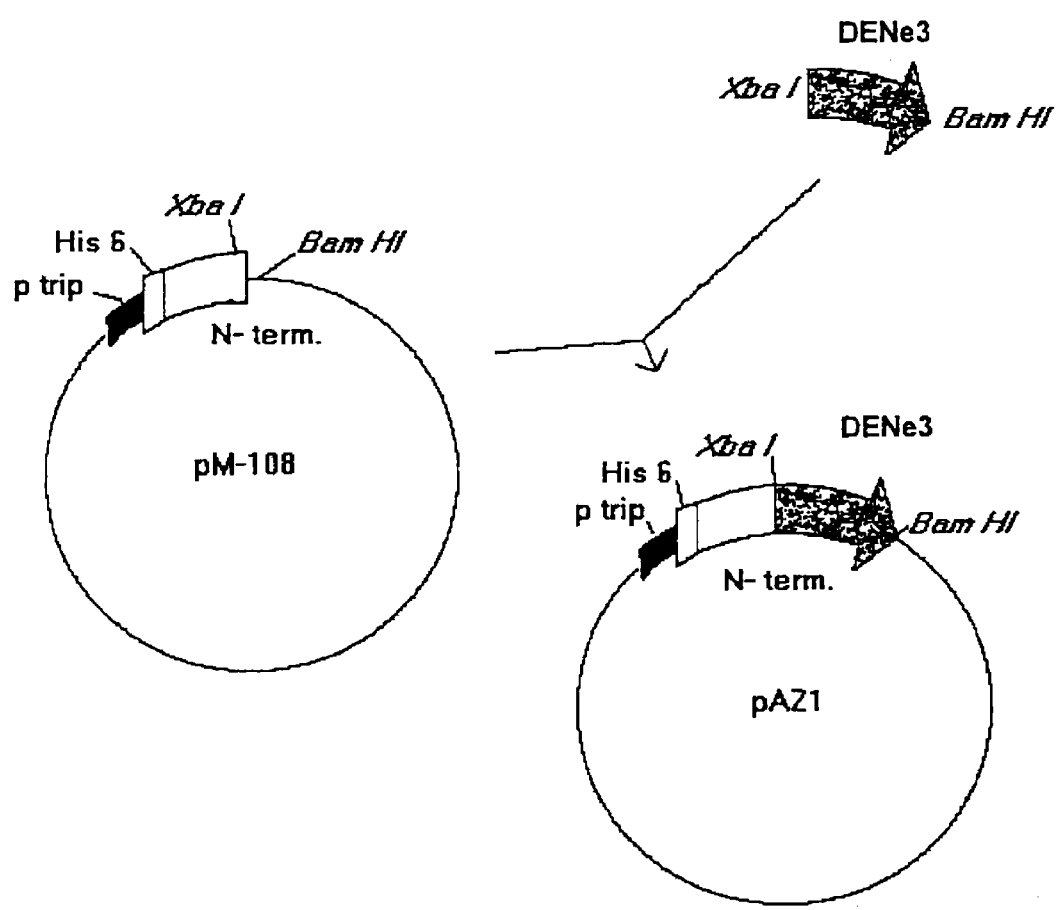
Figure 8:
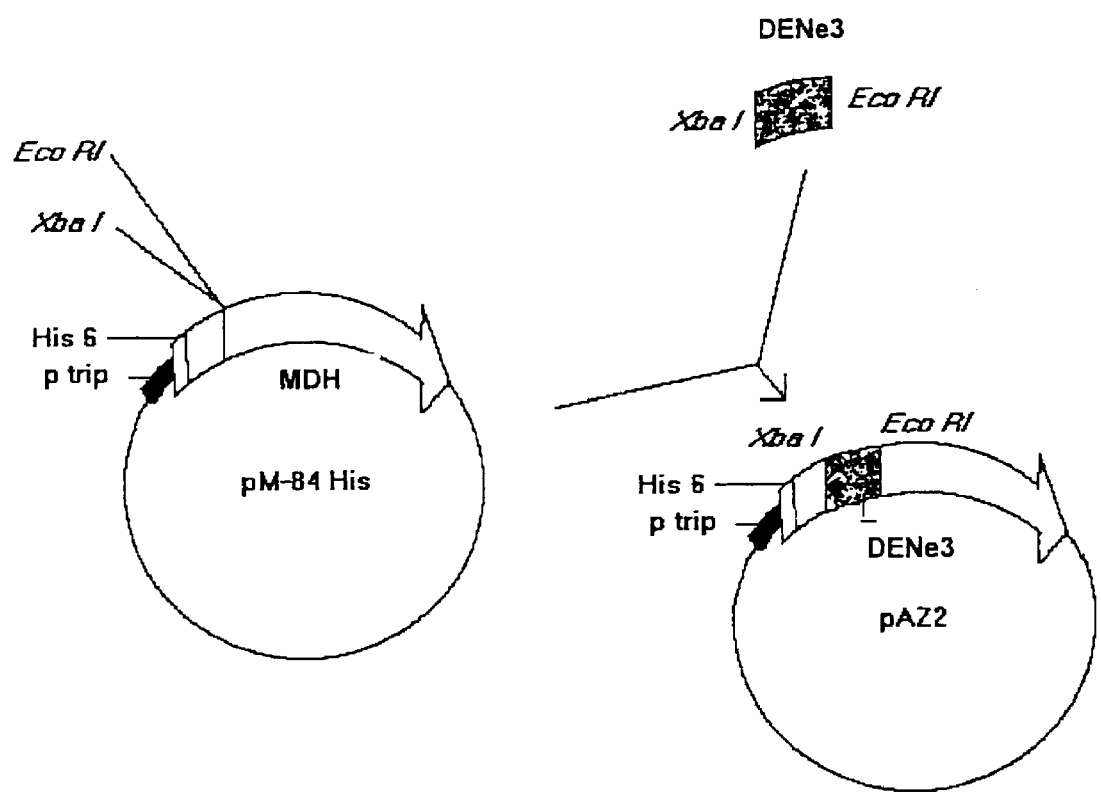

The vector was created by digestion of the pD4 plasmid with Bam HI/Bam HI which contains the nucleotide sequence that codifies for the MDH protein and for a sequence of 6 histidines without stop codon (Sequence No. 29). This digestion permits to the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pLL3 (FIG. 3 and Sequence No. 30). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-2 virus. The protein was recognized in Immunoblotting by a HMAFI anti-DEN-2 and was denominated PLL3 (Sequence No. 31).

Example 10

Purification of the PLL3 Protein

The biomass obtained from the E. coli strain transformed with pLL2 and grown at 37° C. was disrupted by French press. The recombinant protein was obtained in both forms: soluble and insoluble. From the insoluble fraction, the protein was extracted using Urea 6 M, and the supernatant, containing the PLL3 protein, was loaded onto a G-25 column to eliminate the chaotropic agent. The fraction obtained was then loaded onto the Chelating-Sepharose FF column (Pharmacia, UK), in the presence of $Cu^{++}$ ions. The column was washed with Imidazolee 30 mM and the protein was eluted with Imidazole 100 mM. Finally, the pure fraction of the protein was loaded onto a G-25 column to obtain the protein in the formulation buffer (PBS). This preparation was used for immunological studies.

Example 11

Antigenic Characterization of PLL3

The purified fraction of PLL3 was characterized either by its recognition by different polyclonal sera and/or murine monoclonal antibodies, as well as by positive human sera to Dengue (table 11).

The highest recognitions in Dot blotting were obtained with the HMAF anti-DEN-2. The recognition by HMAF against the other serotypes was lower than in the case of serotype 2, in decreasing order: DEN-1, DEN-3 and DEN-4. The antibodies generated by other flavivirus like the Yellow Fever virus and the Saint Louis Encephalitis virus had not any recognition at all. Nevertheless, related to the Mab 3H5, a great reactivity was observed (similar to those obtained with the PLL2) either by Dot blot and Western blot. Contrariously to the PLL1 results, the recognition with the Mab 3H5 was the same when the reducing agents are present in the sample, indicating a possible conformational difference between both proteins. Finally, the reactivity against three human sera of high titers and three of low titers against DEN-2 was measured, achieving a substantial signal in both cases by Western blotting and Dot blotting. These results were similar to those obtained with PLL2.

TABLE 11

Reactivity of PLL3 protein to monoclonal and polyclonal antibodies.

| Abs** | Specificity*** | PLL3* |
|---|---|---|
| HMAF | DEN-1 | ++ |
| HMAF | DEN-2 | +++ |
| HMAF | DEN-3 | – |
| HMAF | DEN-4 | – |
| HMAF | EEE | – |
| HMAF | YFV | – |
| HMAF | SLV | – |
| Mab 3H5 | NT | +++ |

*A total of 10 μg of purified PLL3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 12

Characterization of the Antibody Response Generated by PLL3

A total of 25 Balb/c mice were i.p immunized with 35 ug of purified PLL3 in Freund adjuvant; 10 animals were bled after four doses and the antibodies anti-DEN were evaluated by ELISA. High antibody titers against DEN-2 were obtained while, no reactivity was obtained against the rest of the serotypes (table 12 and table 15). In addition, the hemagglutination inhibition (HI) assay was done and only positive titers were found against DEN-2 (table 13 and table 15). Finally, the in vitro neutralization assay was done and neutralization titers of 1:1280 against DEN-2 were obtained (table 14). No neutralization of the viral infection was found against the rest of the serotypes (table 15). Using the three tests, high levels of serotype-specific antibodies were detected, similar of those obtained after the immunization with the PLL2 protein.

TABLE 12

Antibody titers against DEN-2 from the sera obtained upon immunization of mice with PLL3.

| Mouse | Titers anti-DEN-2 (PLL3) | Titers anti-DEN-2 PBS C(—) |
|---|---|---|
| 1 | 1:128 000 | <1:100 |
| 2 | >1:128 000 | <1:100 |
| 3 | >1:128 000 | <1:100 |
| 4 | 1:64 000 | <1:100 |
| 5 | >1:128 000 | <1:100 |
| 6 | 1:64 000 | <1:100 |
| 7 | >1:128 000 | <1:100 |
| 8 | >1:128 000 | <1:100 |
| 9 | 1:128 000 | <1:100 |
| 10 | >1:128 000 | <1:100 |

TABLE 13

Titers by HI of the sera from the animals immunized with PLL3.

| Mouse | Titers by HI* anti-DEN-2 (PLL3) | Titers by HI anti-DEN-2 PBS C(—) |
|---|---|---|
| 1 | >1:640 | <1:5 |
| 2 | 1:320 | <1:5 |
| 3 | 1:320 | <1:5 |
| 4 | >1:640 | <1:5 |
| 5 | 1:320 | <1:5 |
| 6 | >1:640 | <1:5 |
| 7 | >1:640 | <1:5 |
| 8 | >1:640 | <1:5 |
| 9 | 1:320 | <1:5 |
| 10 | >1:640 | <1:5 |

*The HI titers were defined as the highest dilution capable of inhibiting the hemagglutination of goose's erythrocytes against 8 hemagglutination viral units.

TABLE 14

Viral neutralization assay with the sera of animals immunized with PLL3.

| Mouse | Neutralizing titers anti-DEN-2 PLL3 | Neutralizing titers anti-DEN-2 PBS C(—) |
|---|---|---|
| 1 | >1:1280 | <1:5 |
| 2 | >1:1280 | <1:5 |
| 3 | >1:1280 | <1:5 |
| 4 | 1:640 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

*The neutralizing titers were defined as the highest dilution of serum having 50% reduction of the number of viral plaques.

TABLE 15

Cross-reactivity assay against all the viral serotypes by ELISA, HI and viral neutralization with the sera of animals immunized with PLL3.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PLL3) | <1/100 | >1:128 000 | <1/100 | <1/100 |
| 2 (PLL3) | <1/100 | >1:128 000 | <1/100 | <1/100 |

| Mixture of sera* | HI**anti-DEN-1 | HI anti-DEN-2 | HI anti-DEN-3 | HI anti-DEN-4 |
|---|---|---|---|---|
| PLL3 | <1/5 | >1/320 | <1/5 | <1/5 |

| Mixture of sera* | Neutralizing titers*** anti-DEN-1 | Neutralizing titers*** anti-DEN-2 | Neutralizing titers*** anti-DEN-3 | Neutralizing titers*** anti-DEN-4 |
|---|---|---|---|---|
| 1 (PLL3) | <1:5 | >1:1280 | <1:5 | <1:5 |
| 2 (PLL3) | <1:5 | >1:1280 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 13

Obtaining of pLH1

The nucleotide sequence that codifies for the amino acids from 286 to 426 of the envelope protein from the DEN-1 virus (Sec. Id. No. 32) was amplified with the oligonucleotides identified in the list of sequences as Sequence No. 6 and Sequence No. 7 from the DEN-1 virus strain genotype (Chu M. C., O'Rourke E. J., Trent D. W. Genetic relatedness among structural protein genes of dengue 1 virus strains. J. Gen. Virol. 1989. 70:1701-1712).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pLH1 (FIG. 4 and Sequence No. 33). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-1 virus. The protein was recognized in Immunoblotting by polyclonal antibodies (PA) anti-DEN-1 contained in the HMAF. This protein was denominated PLH1 (Sequence No. 34).

Example 14

Purification of the Protein PLH1

The biomass obtained from the *E. coli* strain transformed with pLH1 and grown at 37° C. was disrupted by French press. The recombinant protein was obtained preponderantly as insoluble form associated to the pellet of the cellular disruption. From the pellet, the protein was extracted with urea 7 M and the supernatant, containing the PLH1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 15

Antigenic Characterization of PLH1

The purified fraction of PLH1 was characterized either by its recognition by different polyclonal sera and/or murine monoclonal antibodies, as well as by positive human sera to Dengue (table 16).

The highest recognitions in Dot blotting were obtained with the HMAF anti-DEN-1. The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against three human sera of high titers and three of low titers against DEN-1 was measured, achieving a substantial signal in both cases by Western blotting and Dot blotting.

TABLE 16

Reactivity of PLH1 protein to monoclonal and polyclonal antibodies

| Abs** | Specificity*** | PLH1 |
|---|---|---|
| HMAF | DEN-1 | ++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

*A total of 10 μg of purified PLH1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 16

Characterization of the Antibody Response Generated by PLH1

A total of 25 Balb/c mice were i.p immunized with 35 ug of purified PLH1 in Freund adjuvant; 10 animals were bled after four doses and the antibodies anti-DEN were evaluated by ELISA. High antibody titers against DEN-1 were obtained while, no reactivity was obtained against the rest of the serotypes (table 17 and table 20). In addition, the HI assay was done and only positive titers were found against DEN-1 (table 18 and table 20). Finally, the in vitro neutralization assay was done and neutralization titers of 1:320 against DEN-1 were obtained. However, no neutralization of the viral infection was found against the rest of the serotypes (table 19 and table 20). These results indicate the high serotype-specificity of the antibodies elicited by PLH1.

TABLE 17

Antibody titers against DEN-1 from the sera obtained upon immunization of mice with PLH1.

| Mouse | Titers anti-DEN-1 (PLH1) | Titers anti-DEN-1 PBS C(—) |
|---|---|---|
| 1 | 1/64 000 | <1:100 |
| 2 | 1/128 000 | <1:100 |
| 3 | 1/64 000 | <1:100 |
| 4 | 1/32 000 | <1:100 |
| 5 | 1/32 000 | <1:100 |
| 6 | 1/64 000 | <1:100 |
| 7 | 1/128 000 | <1:100 |
| 8 | 1/64 000 | <1:100 |
| 9 | 1/128 000 | <1:100 |
| 10 | 1/128 000 | <1:100 |

TABLE 18

Titers by HI of the sera from the animals immunized with PLH1.

| Mouse | Titers by HI* anti-DEN-1 (PLH1) | Titers by HI* anti-DEN-1 PBS C(—) |
|---|---|---|
| 1 | >1:640 | <1:5 |
| 2 | 1:320 | <1:5 |
| 3 | >1:640 | <1:5 |
| 4 | >1:640 | <1:5 |
| 5 | >1:640 | <1:5 |
| 6 | 1:320 | <1:5 |
| 7 | 1:40 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 19

Viral neutralization assay with the sera of animals immunized with PLH1.

| Mouse | Neutralizing titers* anti-DEN-1 (PLH1) | Neutralizing titers* anti-DEN-1 PBS C(—) |
|---|---|---|
| 1 | 1:80 | <1:5 |
| 2 | 1:320 | <1:5 |
| 3 | 1:40 | <1:5 |
| 4 | 1:320 | <1:5 |
| 5 | 1:80 | <1:5 |
| 6 | 1:160 | <1:5 |
| 7 | 1:320 | <1:5 |
| 8 | 1:320 | <1:5 |
| 9 | 1:320 | <1:5 |
| 10 | 1:320 | <1:5 |

*The neutralizing titers were defined as the highest dilution of serum having 50% reduction of the number of viral plaques.

TABLE 20

Cross-reactivity assay against all the viral serotypes by ELISA, HI and viral neutralization with the sera of animals immunized with PLH1.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLH1) | 1:128 000 | <1/100 | <1/100 | <1/100 |
| 2 (PLH1) | >1:128 000 | <1/100 | <1/100 | <1/100 |
| Mixture of sera* | HI** anti-DEN-1 | HI anti-DEN-2 | HI anti-DEN-3 | HI anti-DEN-4 |
| PLH1 | >1:320 | <1/5 | <1/5 | <1/5 |

TABLE 20-continued

Cross-reactivity assay against all the viral serotypes by ELISA, HI and viral neutralization with the sera of animals immunized with PLH1.

| Mixture of sera* | Neutralizing titers*** anti-DEN-1 | Neutralizing titers*** anti-DEN-2 | Neutralizing titers*** anti-DEN-3 | Neutralizing titers*** anti-DEN-4 |
|---|---|---|---|---|
| 1 (PLH1) | 1:160 | <1:5 | <1:5 | <1:5 |
| 2 (PLH1) | 1:320 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 17

Obtaining of pLH2

The nucleotide sequence that codifies for the amino acids from 286 to 426 of the envelope protein from the DEN-1 virus (Sequence No. 32) was amplified with the oligonucleotides identified in the list of sequences as Sequence No. 6 and Sequence No. 8 from a DEN-1 viral strain (Chu M. C., O'Rourke E. J., Trent D. W. Genetic relatedness among structural protein genes of dengue 1 virus strains. J. Gen. Virol. 1989. 70:1701-1712).

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pLH2 (FIG. 5 and Sequence No. 35). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-1 virus. The protein was recognized in Immunoblotting by a HMAF anti-DEN-1 and was denominated PLH2 (Sequence No. 36).

Example 18

Purification of the PLH2 Protein

The biomass obtained from the *E. coli* strain transformed with pLH2 and grown at 37° C. was disrupted by French press. The recombinant protein was obtained in both forms: soluble and insoluble. The protein associated to the insoluble fraction was extracted using Urea 7 M, and the supernatant, containing the PLH2 protein, was loaded onto a G-25 column to eliminate the chaotropic agent. The fraction obtained was then loaded onto the chelating-sepharose FF column (Pharmacia, UK), in the presence of $Cu^{++}$ ions. The column was washed with Imidazolee 40 mM and the protein was eluted with Imidazole 100 mM. Finally, the pure fraction was loaded onto a G-25 column to obtain the protein in the formulation (PBS). This preparation was used for immunological studies.

Example 19

Antigenic Characterization of PLH2

The purified fraction of PLH2 was characterized either by its recognition by different polyclonal sera and/or murine monoclonal antibodies, as well as by positive human sera to Dengue (table 21).

The highest recognitions in Dot blotting were obtained with the HMAF anti-DEN-1 (higher than those obtained with PLH1). The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against five human sera of high titers and three of low titers against DEN-1 was measured, achieving a substantial signal in both cases by Western blotting and Dot blotting.

TABLE 21

| Reactivity of PLH2 protein to monoclonal and polyclonal antibodies. | | |
|---|---|---|
| Abs** | Specificity*** | PLH2 |
| HMAF | DEN-1 | +++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

*A total of 10 μg of purified PLH2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 20

Characterization of the Antibody Response Generated by PLH2

A total of 25 Balb/c mice were i.p immunized with 20 ug of purified PLH2 in Freund adjuvant; 10 animals were bled after four doses and the antibodies anti-DEN were evaluated by ELISA. High antibody titers against DEN-1 were obtained while, no reactivity was obtained against the rest of the serotypes (table 22 and table 25). In addition, the HI assay was done and only positive titers were found against DEN-1 (table 23 and table 25). Finally, the in vitro neutralization assay was done and neutralization titers of 1:1280 against DEN-1 were obtained (table 24). No neutralization of the viral infection was found against the rest of the serotypes. (table 25).

TABLE 22

| Antibody titers against DEN-1 from the sera obtained upon immunization of mice with PLH2. | | |
|---|---|---|
| Mouse | Titers anti-DEN-1 (PLH2) | Titers anti-DEN-1 PBS C(—) |
| 1 | 1:128 000 | <1:100 |
| 2 | >1:128 000 | <1:100 |
| 3 | 1:64000 | <1:100 |
| 4 | >1:128 000 | <1:100 |

TABLE 22-continued

Antibody titers against DEN-1 from the sera obtained upon immunization of mice with PLH2.

| Mouse | Titers anti-DEN-1 (PLH2) | Titers anti-DEN-1 PBS C (—) |
|---|---|---|
| 5 | 1:128 000 | <1:100 |
| 6 | 1:64000 | <1:100 |
| 7 | >1:128 000 | <1:100 |
| 8 | 1:128 000 | <1:100 |
| 9 | >1:128 000 | <1:100 |
| 10 | >1:128 000 | <1:100 |

TABLE 23

Titers by HI of the sera from the animals immunized with PLH2.

| Mouse | Titers by HI* anti-DEN-1 (PLH2) | Titers by HI anti-DEN-1 PBS C (—) |
|---|---|---|
| 1 | <1:5 | <1:5 |
| 2 | >1:640 | <1:5 |
| 3 | 1:320 | <1:5 |
| 4 | 1:320 | <1:5 |
| 5 | >1:640 | <1:5 |
| 6 | >1:640 | <1:5 |
| 7 | >1:640 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 24

Viral neutralization assay with the sera of animals immunized with PLH2.

| Mouse | Neutralizing titers* anti-DEN-1 (PLH2) | Neutralizing titers* anti-DEN-1. C (—) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

*The neutralizing titers were defined as the highest dilution of serum having 50% reduction of the number of viral plaques.

TABLE 25

Cross-reactivity assay against all the viral serotypes by ELISA, HI and viral neutralization with the sera of animals immunized with PLH2.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PLH2) | 1:64 000 | <1/100 | <1/100 | <1/100 |
| 2 (PLH2) | >1:128 000 | <1/100 | <1/100 | <1/100 |

| Mixture of sera* | HI** anti-DEN-1 | HI anti-DEN-2 | HI anti-DEN-3 | HI anti-DEN-4 |
|---|---|---|---|---|
| PLH2 | >1/320 | <1/5 | <1/5 | <1/5 |

TABLE 25-continued

Cross-reactivity assay against all the viral serotypes by ELISA, HI and viral neutralization with the sera of animals immunized with PLH2.

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PLH2) | >1:1280 | <1:5 | <1:5 | <1:5 |
| 2 (PLH2) | >1:1280 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 21

Obtaining of pLH3

The nucleotide sequence that codifies for the amino acids from 286 to 426 of the envelope protein from the DEN-1 virus (Sec. Id. No. 32) was amplified with the oligonucleotides identified in the list of sequences as Sequence No. 9 and Sequence No. 10 from the DEN-1 virus strain (Chu M. C., O'Rourke E. J., Trent D. W. Genetic relatedness among structural protein genes of dengue 1 virus strain. J. Gen. Virol. 1989. 70:1701-1712).

The vector was created by digestion of the pD4 plasmid with Bam HI/Bam HI which contains the nucleotide sequence that codifies for the MDH protein and for a sequence of 6 histidines without stop codon (Sequence No. 29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pLH3 (FIG. 6 and Sequence No. 37). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-1 virus. The protein was recognized in Immunoblotting by a HMAF anti-DEN-1 and was denominated PLH3 (Sequence No. 38).

Example 22

Purification of the PLH3 Protein

The biomass obtained from the *E. coli* strain transformed with pLH3 and grown at 37° C. was disrupted by French press. The recombinant protein was obtained in both forms: soluble and insoluble. From the insoluble fraction, the protein was extracted using Urea 6 M, and the supernatant, containing the PLH3 protein, was loaded onto a G-25 column to eliminate the chaotropic agent. The fraction obtained was then loaded onto the Chelating-Sepharose FF column (Pharmacia, UK), in the presence of $Cu^{++}$ ions. The column was washed with Imidazolee 30 mM and the protein was eluted with Imidazole 250 mM. Finally, the pure fraction of the protein was loaded onto a G-25 column to obtain the protein in the formulation buffer (PBS). This preparation was used for immunological studies.

Example 23

Antigenic Characterization of PLH3

The purified fraction of PLH3 was characterized either by its recognition by different polyclonal sera and/or murine monoclonal antibodies, as well as by positive human sera to Dengue (table 26).

The highest recognitions in Dot blotting were obtained with the HMAF anti-DEN-1. The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against three human sera of high titers and three of low titers against DEN-1 was measured, achieving a substantial signal in both cases by Dot blotting and Western blotting.

TABLE 26

Reactivity of PLH3 protein to monoclonal and polyclonal antibodies.

| Abs** | Specificity*** | PLH3 |
|---|---|---|
| HMAF | DEN-1 | +++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

* A total of 10 µg of purified PLH3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 24

Characterization of the Antibody Response Generated by PLH3

A total of 25 Balb/c mice were i.p immunized with 20 ug of purified PLH3 in Freund adjuvant; 10 animals were bled after four doses and the antibodies anti-DEN were evaluated by ELISA. High antibody titers against DEN-1 were obtained while, no reactivity was obtained against the rest of the serotypes (table 27 and table 30). In addition, the HI assay was done and only positive titers were found against DEN-1 (table 28 and table 30). Finally, the in vitro neutralization assay was done and neutralization titers of 1:1280 against DEN-1 were obtained (table 29). No neutralization of the viral infection was found against the rest of the serotypes (table 30).

TABLE 27

Antibody titers against DEN-1 from the sera obtained upon immunization of mice with PLH3.

| Mouse | Titers anti-DEN-1 PLH3 | Titers anti-DEN-1 PBS Control (—) |
|---|---|---|
| 1 | 1:64 000 | <1:100 |
| 2 | >1:128 000 | <1:100 |
| 3 | 1:64 000 | <1:100 |
| 4 | >1:128 000 | <1:100 |
| 5 | 1:128 000 | <1:100 |
| 6 | 1:128 000 | <1:100 |
| 7 | 1:128 000 | <1:100 |
| 8 | >1:128 000 | <1:100 |
| 9 | 1:64 000 | <1:100 |
| 10 | >1:128 000 | <1:100 |

TABLE 28

Titers by HI of the sera from the animals immunized with PLH3.

| Mouse | Titers by HI* anti-DEN-1 PLH3 | Titers by HI anti-DEN-1 PBS C (—) |
|---|---|---|
| 1 | 1:320 | <1:5 |
| 2 | >1:640 | <1:5 |
| 3 | >1:640 | <1:5 |
| 4 | 1:320 | <1:5 |
| 5 | 1:320 | <1:5 |
| 6 | >1:640 | <1:5 |
| 7 | 1:320 | <1:5 |
| 8 | <1:5 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 29

Viral neutralization assay with the sera of animals immunized with PLH3.

| Mouse | Neutralizing titers* anti-DEN-1 PLH3 | Neutralizing titers* anti-DEN-1 PBS C (—) |
|---|---|---|
| 1 | >1:1280 | <1:5 |
| 2 | >1:1280 | <1:5 |
| 3 | >1:1280 | <1:5 |
| 4 | 1:640 | <1:5 |
| 5 | 1:640 | <1:5 |
| 6 | >1:1280 | <1:5 |
| 7 | >1:1280 | <1:5 |
| 8 | >1:1280 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 30

Cross-reactivity assay against all the viral serotypes by ELISA, HI and viral neutralization with the sera of animals immunized with PLH3.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLH3) | 1:128 000 | <1/100 | <1/100 | <1/100 |
| 2 (PLH3) | >1:128 000 | <1/100 | <1/100 | <1/100 |

| Mixture of sera* | HI** anti-DEN-1 | HI anti-DEN-2 | HI anti-DEN-3 | HI anti-DEN-4 |
|---|---|---|---|---|
| PLH3 | >1/320 | <1/5 | <1/5 | <1/5 |

TABLE 30-continued

Cross-reactivity assay against all the viral serotypes by ELISA, HI and viral neutralization with the sera of animals immunized with PLH3.

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PLH3) | >1:1280 | <1:5 | <1:5 | <1:5 |
| 2 (PLH3) | >1:1280 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 25

Obtaining of pAZ1

The nucleotide sequence that codifies for the amino acids from 286 to 426 of the envelope protein from the DEN-3 virus (Seq. 39) was amplified with the oligonucleotides identified in the list of sequences as Sequence No. 11 and Sequence No. 12 from the DEN-3 virus strain genotype (Osatomi K., Sumiyoshi H. Complete nucleotide sequence of dengue type 3 virus genome RNA. Virology. 1990. 176(2):643-647).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pAZ1 (FIG. 7 and Sequence No. 40). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-3 virus. The protein was recognized in Immunoblotting by polyclonal antibodies (PA) anti-DEN-3 contained in the HMAF. This protein was denominated PAZ1 (Sequence No. 41).

Example 26

Purification of the Protein PAZ1

The biomass obtained from the *E. coli* strain transformed with pAZ1 and grown at 37° C. was disrupted by French press. The recombinant protein was obtained preponderantly as insoluble form associated to the pellet of the cellular disruption. From the pellet, the protein was extracted with urea 7 M and the supernatant, containing the PLH1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 27

Antigenic Characterization of PAZ1

The purified fraction of PAZ1 was characterized either by its recognition by different polyclonal sera and/or murine monoclonal antibodies, as well as by positive human sera to Dengue (table 31).

The highest recognitions in Dot blotting were obtained with the HMAF anti-DEN-3. The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against three human sera of high titers and three of low titers against DEN-3 was measured, achieving a substantial signal in both cases by Dot blotting Western blotting.

TABLE 31

Reactivity of PAZ1 protein to monoclonal and polyclonal antibodies.

| Abs** | Specificity*** | PAZ1 |
|---|---|---|
| HMAF | DEN-1 | − |
| HMAF | DEN-2 | + |
| HMAF | DEN-3 | ++ |
| HMAF | DEN-4 | + |
| HMAF | EEE | − |
| HMAF | YFV | − |
| HMAF | SLV | − |
| Mab 3H5 | NT | − |

* A total of 10 μg of purified PAZ1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 28

Characterization of the Antibody Response Generated by PAZ1

A total of 25 Balb/c mice were i.p immunized with 35 ug of purified PAZ1 in Freund adjuvant; 10 animals were bled after four doses and the antibodies anti-DEN were evaluated by ELISA. High antibody titers against DEN-1 were obtained while, no reactivity was obtained against the rest of the serotypes (table 32 and table 35). In addition, the HI assay was done and only positive titers were found against DEN-3 (table 33 and table 35). Finally, the in vitro neutralization assay was done and neutralization titers of 1:320 against DEN-3 were obtained. However, no neutralization of the viral infection was found against the rest of the serotypes (table 34 and table 35). These results indicate the high serotype-specificity of the antibodies elicited by PAZ1.

TABLE 32

Antibody titers against DEN-3 from the sera obtained upon immunization of mice with PAZ1.

| Mouse | Titers anti-DEN-3 PAZ1 | Titers anti-DEN-3 PBS Control (—) |
|---|---|---|
| 1 | 1/64 000 | <1:100 |
| 2 | 1/128 000 | <1:100 |
| 3 | 1/32 000 | <1:100 |
| 4 | 1/64 000 | <1:100 |
| 5 | 1/64 000 | <1:100 |
| 6 | 1/128 000 | <1:100 |
| 7 | 1/64 000 | <1:100 |
| 8 | 1/64 000 | <1:100 |
| 9 | 1/128 000 | <1:100 |
| 10 | 1/128 000 | <1:100 |

TABLE 33

Titers by HI of the sera from the animals immunized with PAZ1.

| Mouse | Titers by HI* anti-DEN-3 PAZ1 | Titers by HI anti-DEN-3 PBS C (—) |
|---|---|---|
| 1 | >1:640 | <1:5 |
| 2 | 1:320 | <1:5 |
| 3 | 1:320 | <1:5 |
| 4 | 1:640 | <1:5 |
| 5 | <1/5 | <1:5 |
| 6 | 1:320 | <1:5 |
| 7 | <1/5 | <1:5 |
| 8 | 1:320 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 34

Viral neutralization assay with the sera of animals immunized with PAZ1.

| Mouse | Neutralizing titers anti-DEN-3 PAZ1 | Neutralizing titers anti-DEN-3 PBS C (—) |
|---|---|---|
| 1 | 1:160 | <1:5 |
| 2 | 1:320 | <1:5 |
| 3 | 1:320 | <1:5 |
| 4 | 1:320 | <1:5 |
| 5 | 1:40 | <1:5 |
| 6 | 1:40 | <1:5 |
| 7 | 1:320 | <1:5 |
| 8 | 1:320 | <1:5 |
| 9 | 1:160 | <1:5 |
| 10 | 1:320 | <1:5 |

* The neutralizing titers were defined as the highest dilution of serum having 50% reduction of the number of viral plaques.

TABLE 35

Cross-reactivity assay against all the viral serotypes by ELISA, HI and viral neutralization with the sera of animals immunized with PAZ1.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PAZ1) | <1/100 | <1/100 | 1:64 000 | <1/100 |
| 2 (PAZ1) | <1/100 | <1/100 | >1:128 000 | <1/100 |

| Mixture of sera* | HI** anti-DEN-1 | HI anti-DEN-2 | HI anti-DEN-3 | HI anti-DEN-4 |
|---|---|---|---|---|
| PAZ1 | <1/5 | <1/5 | >1:320 | <1/5 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PAZ1) | <1:5 | <1:5 | 1:320 | <1:5 |
| 2 (PAZ1) | <1:5 | <1:5 | 1:320 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 29

Obtaining of pAZ2

The nucleotide sequence that codifies for the amino acids from 286 to 426 of the envelope protein from the DEN-3 virus (Sequence No. 39) was amplified with the oligonucleotides identified in the list of sequences as Sequence No. 11 and Sequence No. 13 from a DEN-3 viral strain (Osatomi K., Sumiyoshi H. Complete nucleotide sequence of dengue type 3 virus genome RNA. Virology. 1990. 176(2):643-647).

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pAZ2 (FIG. 8 and Sequence No. 42). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-3 virus. The protein was recognized in Immunoblotting by a HMAF anti-DEN-3 and was denominated PAZ2 (Sequence No. 43).

Example 30

Purification of the PAZ2 Protein

The biomass obtained from the *E. coli* strain transformed with pAZ2 and grown at 37° C. was disrupted by French press. The recombinant protein was obtained in both forms: soluble and insoluble. The protein associated to the insoluble fraction was extracted using Urea 7 M, and the supernatant, containing the PAZ2 protein, was loaded onto a G-25 column to eliminate the chaotropic agent. The fraction obtained was then loaded onto the Chelating-sepharose FF column (Pharmacia, UK), in the presence of $Cu^{++}$ ions. The column was washed with Imidazolee 40 mM and the protein was eluted with Imidazole 100 mM. Finally, the pure fraction was loaded onto a G-25 column to obtain the protein in the formulation (PBS). This preparation was used for immunological studies.

Example 31

Antigenic Characterization of PAZ2

The purified fraction of PAZ2 was characterized either by its recognition by different polyclonal sera and/or murine monoclonal antibodies, as well as by positive human sera to Dengue (table 36).

The highest recognitions in Dot blotting were obtained with the HMAF anti-DEN-3 (higher than those obtained with PAZ1). The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against five human sera of high titers and three of low titers against DEN-3 was measured, achieving a substantial signal in both cases by Western blotting and Dot blotting.

TABLE 36

Reactivity of PAZ2 protein to monoclonal and polyclonal antibodies.

| Abs** | Specificity*** | PAZ2 |
|---|---|---|
| HMAF | DEN-1 | − |
| HMAF | DEN-2 | − |
| HMAF | DEN-3 | +++ |
| HMAF | DEN-4 | + |
| HMAF | EEE | − |
| HMAF | YFV | − |
| HMAF | SLV | − |
| Mab 3H5 | NT | − |

* A total of 10 μg of purified PAZ2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype Example 32

Characterization of the Antibody Response Generated by PAZ2

A total of 25 Balb/c mice were i.p immunized with 20 ug of purified PAZ2 in Freund adjuvant; 10 animals were bled after four doses and the antibodies anti-DEN were evaluated by ELISA. High antibody titers against DEN-3 were obtained while, no reactivity was obtained against the rest of the serotypes (table 37 and table 40). In addition, the HI assay was done and only positive titers were found against DEN-3 (table 38 and table 40). Finally, the in vitro neutralization assay was done and neutralization titers of 1:1280 against DEN-3 were obtained (table 39). No neutralization of the viral infection was found against the rest of the serotypes (table 40).

TABLE 37

Antibody titers against DEN-3 from the sera obtained upon immunization of mice with PAZ2.

| Mouse | Titers anti-DEN-3 PAZ2 | Titers anti-DEN-3 PBS Control (—) |
|---|---|---|
| 1 | >1:128 000 | <1:100 |
| 2 | 1:128 000 | <1:100 |
| 3 | >1:128 000 | <1:100 |
| 4 | >1:128 000 | <1:100 |
| 5 | 1:128 000 | <1:100 |
| 6 | >1:128 000 | <1:100 |
| 7 | 1:64000 | <1:100 |
| 8 | >1:128 000 | <1:100 |
| 9 | 1:64000 | <1:100 |
| 10 | >1:128 000 | <1:100 |

TABLE 38

Titers by HI of the sera from the animals immunized with PAZ2.

| Mouse | Titers anti-DEN-3 PAZ2 | Titers anti-DEN-3 PBS |
|---|---|---|
| 1 | >1:640 | <1:5 |
| 2 | 1:320 | <1:5 |
| 3 | >1:640 | <1:5 |
| 4 | >1:640 | <1:5 |
| 5 | >1:640 | <1:5 |
| 6 | 1:320 | <1:5 |
| 7 | <1:5 | <1:5 |
| 8 | 1:320 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 39

Viral neutralization assay with the sera of animals immunized with PAZ2.

| Mouse | Neutralizing titers anti-DEN-3 PAZ2 | Neutralizing titers anti-DEN-3 PBS C (—) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | 1:640 | <1:5 |
| 7 | >1:1280 | <1:5 |
| 8 | 1:640 | <1:5 |
| 9 | >1:1280 | <1:5 |
| 10 | 1:640 | <1:5 |

*The neutralizing titers were defined as the highest dilution of serum having 50% reduction of the number of viral plaques.

TABLE 40

Cross-reactivity assay against all the viral serotypes by ELISA, HI and viral neutralization with the sera of animals immunized with PAZ2.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PAZ2) | <1/100 | <1/100 | >1:128 000 | <1/100 |
| 2 (PAZ2) | <1/100 | <1/100 | >1:128 000 | <1/100 |

| Mixture of sera* | HI** anti-DEN-1 | HI anti-DEN-2 | HI anti-DEN-3 | HI anti-DEN-4 |
|---|---|---|---|---|
| PAZ2 | <1/5 | <1/5 | >1/320 | <1/5 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PAZ2) | <1:5 | <1:5 | >1:1280 | <1:5 |
| 2 (PAZ2) | <1:5 | <1:5 | >1:1280 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 33

Obtaining of pAZ3

The nucleotide sequence that codifies for the amino acids from 286 to 426 of the envelope protein from the DEN-3 virus (Seq. 39) was amplified with the oligonucleotides identified in the list of sequences as Sequence No. 14 and Sequence No. 15 from the DEN-3 viral strain (Osatomi K., Sumiyoshi H. Complete nucleotide sequence of dengue type 3 virus genome RNA. Virology. 1990. 176(2):643-647).

Figure 9:
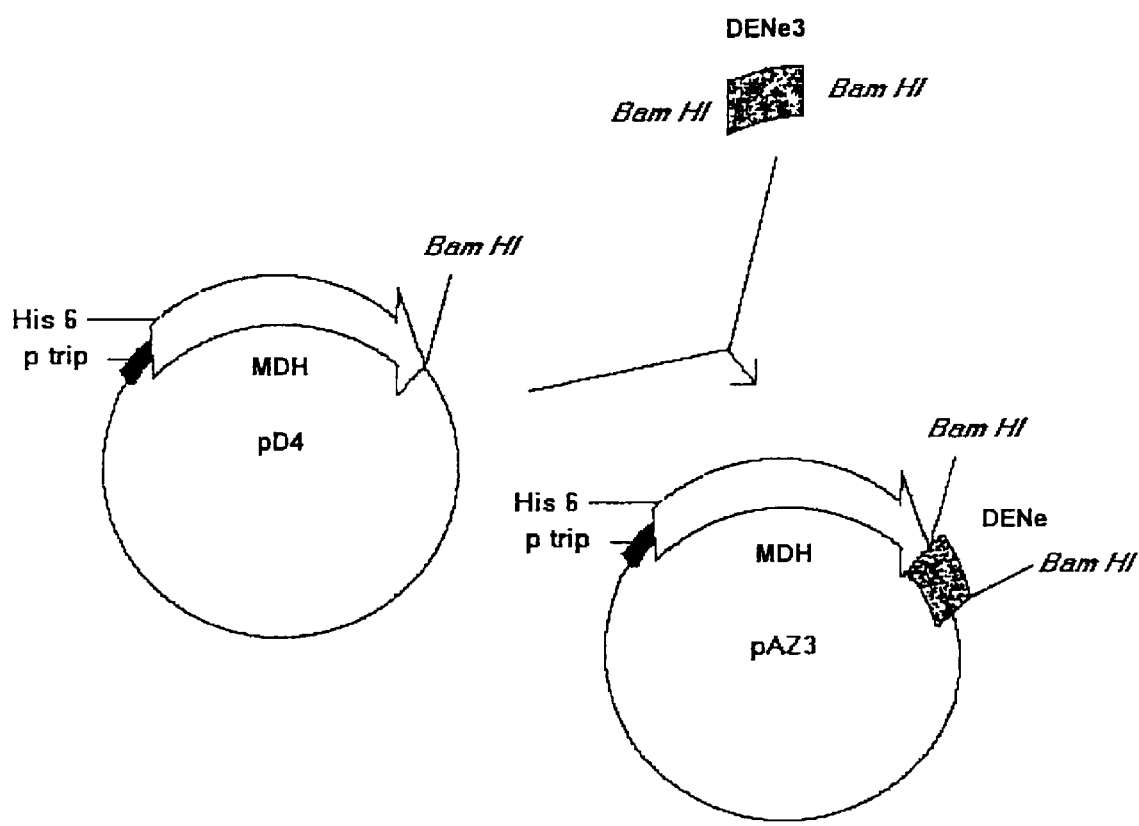

The vector was created by digestion of the pD4 plasmid with Bam HI/Bam HI which contains the nucleotide sequence histidines without stop codon (Sequence No. 29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pAZ3 (FIG. 9 and Sequence No. 44). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-3 virus. The protein was recognized in Immunoblotting by a HMAF anti-DEN-3 and was denominated PAZ3 (Sequence No. 45).

Example 34

Purification of the PAZ3 Protein

The biomass obtained from the *E. coli* strain transformed with pAZ3 and grown at 37° C. was disrupted by French press. The recombinant protein was obtained in both forms: soluble and insoluble. From the insoluble fraction, the protein was extracted using Urea 7 M, and the supernatant, containing the PAZ3 protein, was loaded onto a G-25 column to eliminate the chaotropic agent. The fraction obtained was then loaded onto the Chelating-Sepharose FF column (Pharmacia, UK), in the presence of $Cu^{++}$ ions. The column was washed with Imidazolee 45 mM and the protein was eluted with Imidazole 230 mM. Finally, the pure fraction of the protein was loaded onto a G-25 column to obtain the protein in the formulation buffer (PBS). This preparation was used for immunological studies.

Example 35

Antigenic Characterization of PAZ3

The purified fraction of PAZ3 was characterized either by its recognition by different polyclonal sera and/or murine monoclonal antibodies, as well as by positive human sera to Dengue (table 26).

The highest recognitions in Dot blotting were obtained with the HMAF anti-DEN-3. The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against three human sera of high titers and three of low titers against DEN-3 was measured, achieving a substantial signal in both cases by Dot blotting and Western blotting.

TABLE 41

Reactivity of PAZ3 protein to monoclonal and polyclonal antibodies.

| Abs** | Specificity*** | PAZ3 |
|---|---|---|
| HMAF | DEN-1 | – |
| HMAF | DEN-2 | – |
| HMAF | DEN-3 | +++ |
| HMAF | DEN-4 | + |
| HMAF | EEE | – |
| HMAF | YFV | – |
| HMAF | SLV | – |
| Mab 3H5 | NT | – |

*A total of 10 μg of purified PAZ3 was applied. The intensity of the signal obtained was evaluated from + to ++.

**HMAF were used 1:100 while the Mab 3H5 was used in dilution 1:1000.

***EEE: Equine Encephalitis virus. YFV: Yellow Fever virus. SLV: Saint Louis Encephalitis virus. NT: Neutralizing specific-serotype.

Example 36

Characterization of the Antibody Response Generated by PAZ3

A total of 25 Balb/c mice were i.p immunized with 20 ug of purified PAZ3 in Freund adjuvant; 10 animals were bled after four doses and the antibodies anti-DEN were evaluated by ELISA. High antibody titers against DEN-3 were obtained while, no reactivity was obtained against the rest of the serotypes (table 42 and table 45). In addition, the HI assay was done and only positive titers were found against DEN-3 (table 43 and table 45). Finally, the in vitro neutralization assay was done and neutralization titers of 1:1280 against DEN-3 were obtained (table 44). No neutralization of the viral infection was found against the rest of the serotypes (table 45).

TABLE 42

Antibody titers against DEN-3 from the sera obtained upon immunization of mice with PAZ3.

| Mouse | Titers anti-DEN-3 PAZ3 | Titers anti-DEN-3 PBS Control (—) |
|---|---|---|
| 1 | >1:128 000 | <1:100 |
| 2 | 1:128 000 | <1:100 |
| 3 | >1:128 000 | <1:100 |
| 4 | 1:128 000 | <1:100 |
| 5 | 1:128 000 | <1:100 |
| 6 | >1:128 000 | <1:100 |
| 7 | >1:128 000 | <1:100 |
| 8 | 1:128 000 | <1:100 |
| 9 | 1:128 000 | <1:100 |
| 10 | >1:128 000 | <1:100 |

TABLE 43

Titers by HI of the sera from the animals immunized with PAZ3.

| Mouse | Titers by HI* anti-DEN-3 PAZ3 | Titers by HI anti-DEN-3 PBS C (—) |
|---|---|---|
| 1 | >1:640 | <1:5 |
| 2 | >1:640 | <1:5 |
| 3 | 1:320 | <1:5 |
| 4 | <1:5 | <1:5 |
| 5 | >1:640 | <1:5 |
| 6 | <1:5 | <1:5 |
| 7 | 1:320 | <1:5 |
| 8 | >1:640 | <1:5 |
| 9 | >1:640 | <1:5 |
| 10 | 1:320 | <1:5 |

*The HI titers were defined as the highest dilution capable of inhibiting the hemagglutination of goose's erythrocytes against 8 hemagglutination viral units.

TABLE 44

Viral neutralization assay with the sera of animals immunized with PAZ3.

| Mouse | Neutralizing titers anti-DEN-3 PAZ3 | Neutralizing titers anti-DEN-3 PBS C (—) |
|---|---|---|
| 1 | >1:1280 | <1:5 |
| 2 | 1:640 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 45

Cross-reactivity assay against all the viral serotypes by ELISA, HI and viral neutralization with the sera of animals immunized with PAZ3.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PAZ3) | <1/100 | <1/100 | >1:128 000 | <1/100 |
| 2 (PAZ3) | <1/100 | <1/100 | 1:128 000 | <1/100 |

| Mixture of sera* | HI** anti-DEN-1 | HI anti-DEN-2 | HI anti-DEN-3 | HI anti-DEN-4 |
|---|---|---|---|---|
| PAZ3 | <1/5 | <1/5 | >1/320 | <1/5 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PAZ3) | <1:5 | <1:5 | >1:1280 | <1:5 |
| 2 (PAZ3) | <1:5 | <1:5 | >1:1280 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 37

Obtaining of pID1

The nucleotide sequence that codifies for the amino acids from 286 to 426 of the envelope protein from the DEN-4 virus (Sequence No. 46) was amplified with the oligonucleotides identified in the list of sequences as Sequence No. 17 and Sequence No. 18 from the DEN-4 virus strain genotype (Zhao B., Mackow E. R., Buckler-White A. J., Markoff L., Chancock R. M., Lai C.-J., Makino Y. Cloning full-length Dengue type 4 viral DNA sequences: Analysis of genes coding for structural proteins. Virology 1986. 155:77-88).

Figure 10:
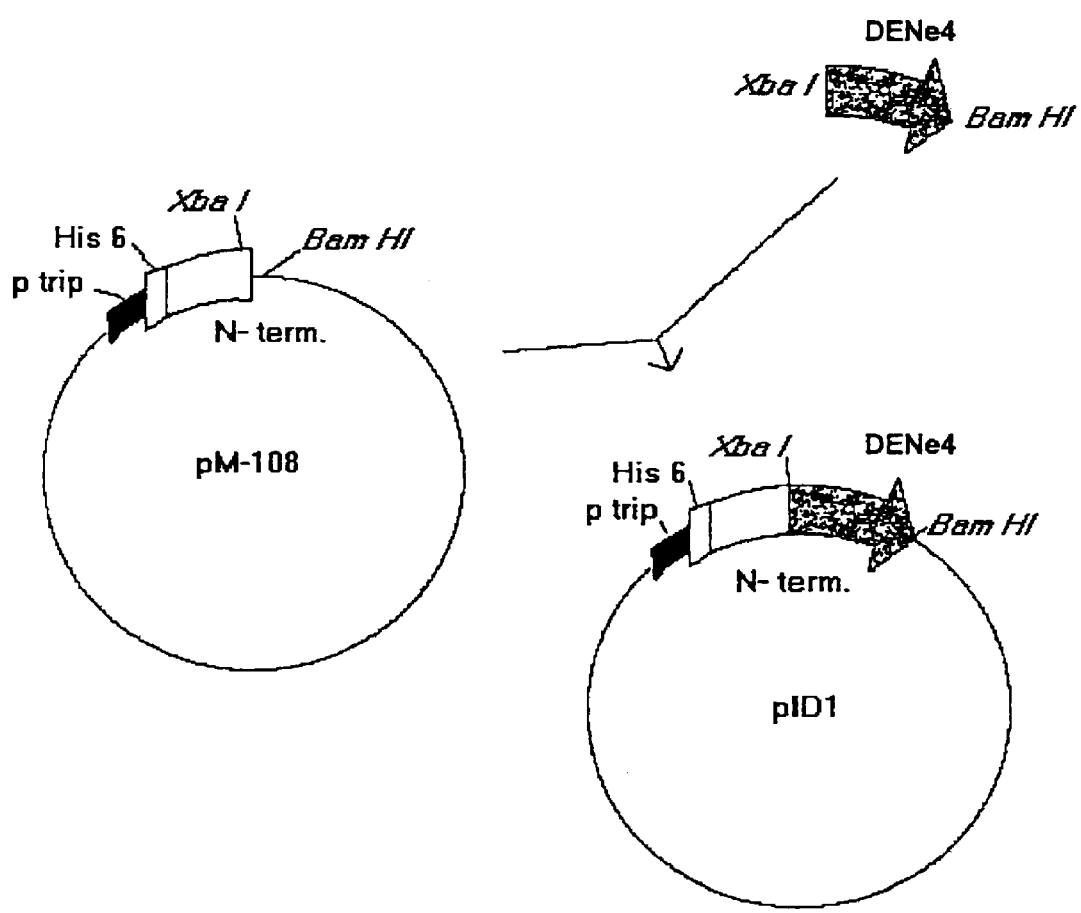
Figure 11:
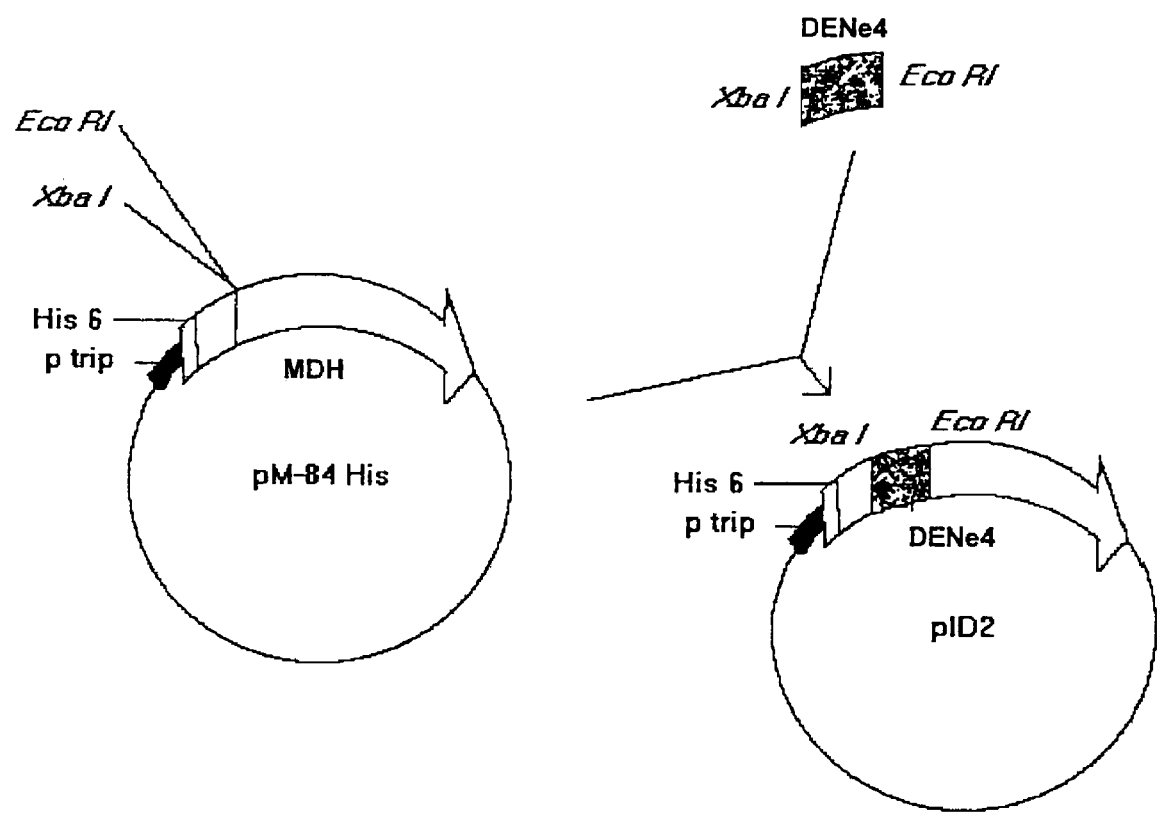
Figure 12:
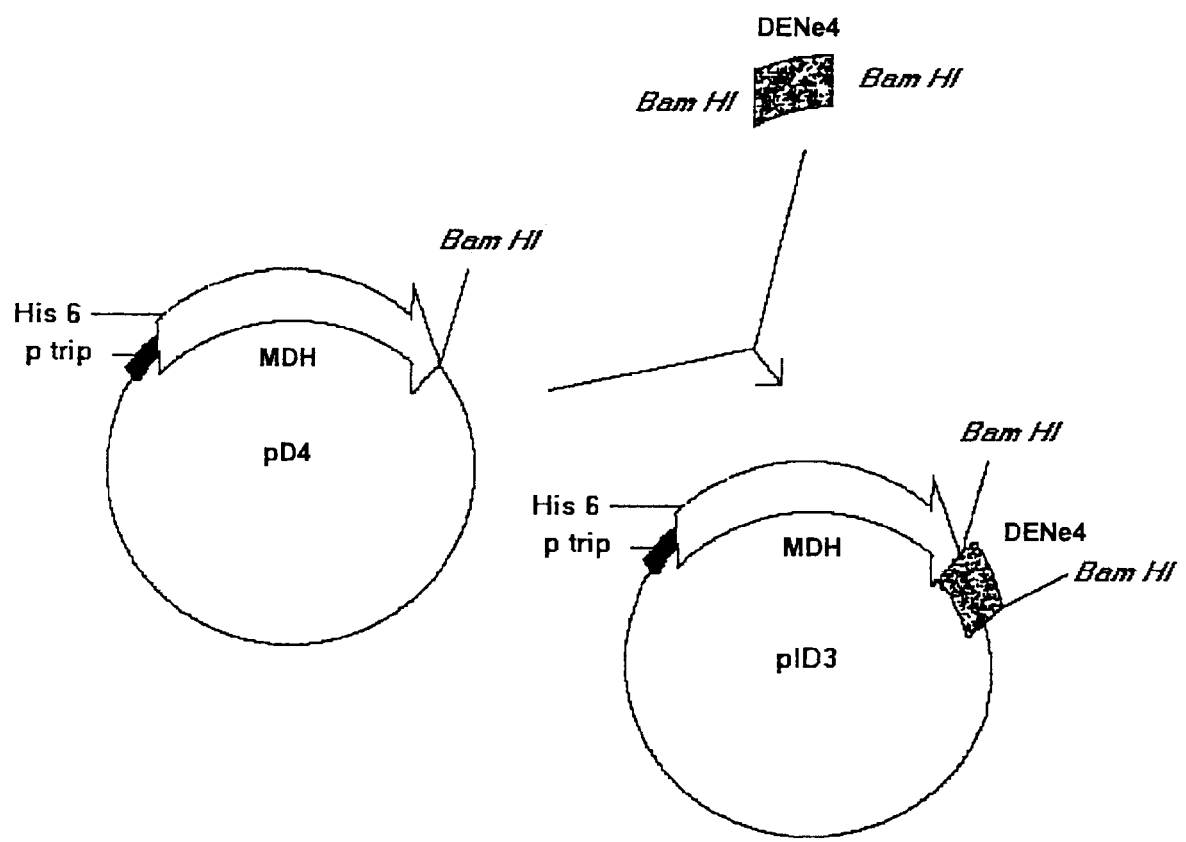
Figure 13:
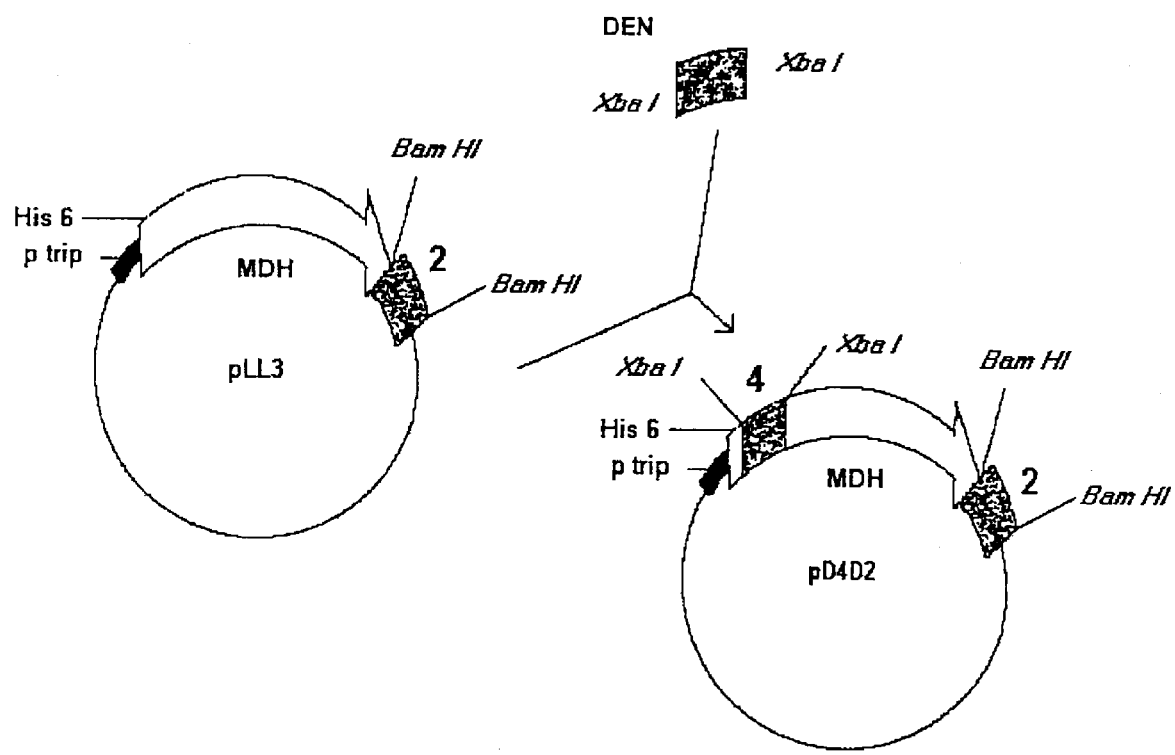

The vector was created by digestion of the pM108 H is plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pID1 (FIG. 10 and Sequence No. 47). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-4 virus. The protein was recognized in Immunoblotting by polyclonal antibodies (PA) anti-DEN-4 contained in the HMAF. This protein was denominated PID1 (Sequence No. 48).

Example 38

Purification of the Protein PID1

The biomass obtained from the E. coli strain transformed with pID1 and grown at 37° C. was disrupted by French press. The recombinant protein was obtained preponderantly as insoluble form associated to the pellet of the cellular disruption. From the pellet, the protein was extracted with urea 6 M and the supernatant, containing the PID1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 39

Antigenic Characterization of PID1

The purified fraction of PID1 was characterized either by its recognition by different polyclonal sera and/or murine monoclonal antibodies, as well as by positive human sera to Dengue (table 46).

The highest recognitions in Dot blotting were obtained with the HMAF anti-DEN-4. The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against three human sera of high titers and three of low titers against DEN-4 was measured, achieving a substantial signal in both cases by Dot blotting Western blotting.

TABLE 46

Reactivity of PID1 protein to monoclonal and polyclonal antibodies.

| Abs** | Specificity*** | PID1 |
|---|---|---|
| HMAF | DEN-1 | – |
| HMAF | DEN-2 | – |
| HMAF | DEN-3 | + |
| HMAF | DEN-4 | ++ |
| HMAF | EEE | – |
| HMAF | YFV | – |
| HMAF | SLV | – |
| Mab 3H5 | NT | – |

*A total of 10 µg of purified PID1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 40

Characterization of the Antibody Response Generated by PID1

A total of 25 Balb/c mice were i.p immunized with 35 ug of purified PID1 in Freund adjuvant; 10 animals were bled after four doses and the antibodies anti-DEN were evaluated by ELISA. High antibody titers against DEN-1 were obtained while, no reactivity was obtained against the rest of the serotypes (table 47 and table 50). In addition, the HI assay was done and only positive titers were found against DEN-4 (table 48 and table 50). Finally, the in vitro neutralization assay was done and neutralization titers of 1:320 against DEN-4 were obtained. However, no neutralization of the viral infection was found against the rest of the serotypes (table 49 and table 50). These results indicate the high serotype-specificity of the antibodies elicited by PID1.

TABLE 47

Antibody titers against DEN-4 from the sera obtained upon immunization of mice with PID1.

| Mouse | Titers anti-DEN-4 PID1 | Titers anti-DEN-4 PBS Control (—) |
|---|---|---|
| 1 | 1/128 000 | <1:100 |
| 2 | 1/128 000 | <1:100 |
| 3 | 1/64 000 | <1:100 |
| 4 | 1/64 000 | <1:100 |
| 5 | 1/128 000 | <1:100 |
| 6 | 1/32 000 | <1:100 |
| 7 | 1/128 000 | <1:100 |
| 8 | 1/32 000 | <1:100 |
| 9 | 1/128 000 | <1:100 |
| 10 | 1/128 000 | <1:100 |

TABLE 48

Titers by HI of the sera from the animals immunized with PID1.

| Mouse | Titers by HI* anti-DEN-4 PID1 | Titers by HI anti-DEN-4 PBS C (—) |
|---|---|---|
| 1 | 1:320 | <1:5 |
| 2 | 1:320 | <1:5 |
| 3 | 1:640 | <1:5 |
| 4 | 1:40 | <1:5 |
| 5 | <1/5 | <1:5 |
| 6 | 1:320 | <1:5 |
| 7 | 1:640 | <1:5 |
| 8 | 1:640 | <1:5 |
| 9 | 1:40 | <1:5 |
| 10 | 1:320 | <1:5 |

*The HI titers were defined as the highest dilution capable of inhibiting the hemagglutination of goose's erythrocytes against 8 hemagglutination viral units.

TABLE 49

Viral neutralization assay with the sera of animals immunized with PID1.

| Mouse | Neutralizing titers anti-DEN-4 PID1 | Neutralizing titers anti-DEN-4 PBS C (—) |
|---|---|---|
| 1 | 1:320 | <1:5 |
| 2 | 1:80 | <1:5 |
| 3 | 1:320 | <1:5 |
| 4 | 1:320 | <1:5 |
| 5 | 1:160 | <1:5 |
| 6 | 1:320 | <1:5 |
| 7 | 1:320 | <1:5 |
| 8 | 1:320 | <1:5 |
| 9 | 1:160 | <1:5 |
| 10 | 1:40 | <1:5 |

*The neutralizing titers were defined as the highest dilution of serum having 50% reduction of the number of viral plaques.

TABLE 50

Cross-reactivity assay against all the viral serotypes by ELISA, HI and viral neutralization with the sera of animals immunized with PID1.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PID1) | <1/100 | <1/100 | <1/100 | 1:64 000 |
| 2 (PID1) | <1/100 | <1/100 | <1/100 | >1:128 000 |

| Mixture of sera* | HI** anti-DEN-1 | HI anti-DEN-2 | HI anti-DEN-3 | HI anti-DEN-4 |
|---|---|---|---|---|
| PID1 | <1/5 | <1/5 | <1/5 | >1:320 |

| Mixture of sera* | Neutralizing titers** anti-DEN-1 | Neutralizing titers anti-DEN-2 | Neutralizing titers anti-DEN-3 | Neutralizing titers anti-DEN-4 |
|---|---|---|---|---|
| 1 (PID1) | <1:5 | <1:5 | <1:5 | 1:160 |
| 2 (PID1) | <1:5 | <1:5 | <1:5 | 1:320 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 41

Obtaining of pID2

The nucleotide sequence that codifies for the amino acids from 286 to 426 of the envelope protein from the DEN-4 virus (Sequence No. 46) was amplified with the oligonucleotides identified in the list of sequences as Sequence No. 16 and Sequence No. 18 from a DEN-4 viral strain (Zhao B., Mackow E. R., Buckler-White A. J., Markoff L., Chancock R. M., Lai C.-J., Makino Y. Cloning full-length Dengue type 4 viral DNA sequences: Analysis of genes coding for structural proteins. Virology 1986. 155:77-88.

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pID2 (FIG. 11 and Sequence No. 49). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-4 virus. The protein was recognized in Immunoblotting by a HMAF anti-DEN-4 and was denominated PID2 (Sequence No. 50).

Example 42

Purification of the PID2 Protein

The biomass obtained from the *E. coli* strain transformed with pID2 and grown at 37° C. was disrupted by French press. The recombinant protein was obtained in both forms: soluble and insoluble. The protein associated to the insoluble fraction was extracted using Urea 6 M, and the supernatant, containing the PID2 protein, was loaded onto a G-25 column to eliminate the chaotropic agent. The fraction obtained was then loaded onto the Chelating-sepharose FF column (Pharmacia, UK), in the presence of $Cu^{++}$ ions. The column was washed with Imidazolee 30 mM and the protein was eluted with Imidazole 250 mM. Finally, the pure fraction was loaded onto a G-25 column to obtain the protein in the formulation (PBS). This preparation was used for immunological studies.

Example 43

Antigenic Characterization of PID2

The purified fraction of PID2 was characterized either by its recognition by different polyclonal sera and/or murine monoclonal antibodies, as well as by positive human sera to Dengue (table 51).

The highest recognitions in Dot blotting were obtained with the HMAF anti-DEN-4 (higher than those obtained with PID1). The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against five human sera of high titers and three of low titers against DEN-3 was measured, achieving a substantial signal in both cases by Western blotting and Dot blotting.

TABLE 51

Reactivity of PID2 protein to monoclonal and polyclonal antibodies.

| Abs** | Specificity*** | PID2 |
|---|---|---|
| HMAF | DEN-1 | − |
| HMAF | DEN-2 | − |
| HMAF | DEN-3 | + |
| HMAF | DEN-4 | +++ |
| HMAF | EEE | − |
| HMAF | YFV | − |
| HMAF | SLV | − |
| Mab 3H5 | NT | − |

*A total of 10 μg of purified PID2 was applied. The intensity of the signal obtained was evaluated from + to ++.

**HMAF were used 1:100 while the Mab 3H5 was used in dilution 1:1000.

***EEE: Equine Encephalitis virus. YFV: Yellow Fever virus. SLV: Saint Louis Encephalitis virus. NT: Neutralizing specific-serotype.

Example 44

Characterization of the Antibody Response Generated by PID2

A total of 25 Balb/c mice were i.p immunized with 20 ug of purified PID2 in Freund adjuvant; 10 animals were bled after four doses and the antibodies anti-DEN were evaluated by ELISA. High antibody titers against DEN-4 were obtained while, no reactivity was obtained against the rest of the serotypes (table 52 and table 55). In addition, the HI assay was done and only positive titers were found against DEN-4 (table 53 and table 55). Finally, the in vitro neutralization assay was done and neutralization titers of 1:1280 against DEN-4 were obtained (table 54). No neutralization of the viral infection was found against the rest of the serotypes (table 55).

TABLE 52

Antibody titers against DEN-4 from the sera obtained upon immunization of mice with PID2.

| Mouse | Titers anti-DEN-4 PID2 | Titers anti-DEN-4 PBSControl (—) |
|---|---|---|
| 1 | 1:64000 | <1:100 |
| 2 | >1:128 000 | <1:100 |
| 3 | 1:128 000 | <1:100 |
| 4 | >1:128 000 | <1:100 |
| 5 | 1:64000 | <1:100 |
| 6 | >1:128 000 | <1:100 |
| 7 | >1:128 000 | <1:100 |
| 8 | >1:128 000 | <1:100 |
| 9 | >1:128 000 | <1:100 |
| 10 | 1:128 000 | <1:100 |

TABLE 53

Titers by HI of the sera from the animals immunized with PID2.

| Mouse | Titers by HI* anti-DEN-4 (PID2) | Titers by HI anti-DEN-4 PBS C (—) |
|---|---|---|
| 1 | 1:320 | <1:5 |
| 2 | 1:320 | <1:5 |
| 3 | 1:640 | <1:5 |
| 4 | 1:40 | <1:5 |
| 5 | <1/5 | <1:5 |
| 6 | 1:320 | <1:5 |
| 7 | 1:640 | <1:5 |
| 8 | 1:640 | <1:5 |
| 9 | 1:40 | <1:5 |
| 10 | 1:320 | <1:5 |

*The HI titers were defined as the highest dilution capable of inhibiting the hemagglutination of goose's erythrocytes against 8 hemagglutination viral units.

TABLE 54

Viral neutralization assay with the sera of animals immunized with PID2.

| Mouse | Neutralizing titers anti-DEN-4 PID2 | Neutralizing titers anti-DEN-4 PBS C (—) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | 1:640 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

* The neutralizing titers were defined as the highest dilution of serum having 50% reduction of the number of viral plaques.

TABLE 55

Cross-reactivity assay against all the viral serotypes by ELISA, HI and viral neutralization with the sera of animals immunized with PID2.

| Mixture of sera* | ELISA (anti-DEN-1) | ELISA (anti DEN-2) | ELISA (anti-DEN-3) | ELISA (anti-DEN-4) |
|---|---|---|---|---|
| 1(PID2) | <1/100 | <1/100 | <1/100 | >1:128 000 |
| 2(PID2) | <1/100 | <1/100 | <1/100 | 1:64 000 |

| Mixture of sera* | HI** anti-DEN-1 | HI anti-DEN-2 | HI anti-DEN-3 | HI anti-DEN-4 |
|---|---|---|---|---|
| PID2 | <1/5 | <1/5 | <1/5 | >1/320 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1(PID2) | <1:5 | <1:5 | <1:5 | >1:1280 |
| 2(PID2) | <1:5 | <1:5 | <1:5 | >1:1280 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 45

Obtaining of pID3

The nucleotide sequence that codifies for the amino acids from 286 to 426 of the envelope protein from the DEN-4 virus (Sequence No. 46) was amplified with the oligonucleotides identified in the list of sequences as Sequence No. 19 and Sequence No. 20 from the DEN-4 viral strain (Zhao B., Mackow E. R., Buckler-White A. J., Markoff L., Chancock R. M., Lai C.-J., Makino Y. Cloning full-length Dengue type 4 viral DNA sequences: Analysis of genes coding for structural proteins. Virology 1986. 155:77-88).

The vector was created by digestion of the pD4 plasmid with Bam HI/Bam HI which contains the nucleotide sequence that codifies for the MDH protein and for a sequence of 6 histidines without stop codon (Sequence No. 29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pID3 (FIG. 12 and Sequence No. 51). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-4 virus. The protein was recognized in Immunoblotting by a HMAF anti-DEN-4 and was denominated PID3 (Sequence No. 52).

Example 46

Purification of the Protein PID3

The biomass obtained from the *E. coli* strain transformed with pID3 and grown at 37° C. was disrupted by French press. The recombinant protein was obtained in both forms: soluble and insoluble. From the insoluble fraction, the protein was extracted using Urea 6 M, and the supernatant, containing the PID3 protein, was loaded onto a G-25 column to eliminate the chaotropic agent. The fraction obtained was then loaded onto the Chelating-Sepharose FF column (Pharmacia, UK), in the presence of $Cu^{++}$ ions. The column was washed with Imidazolee 45 mM and the protein was eluted with Imidazole 200 mM. Finally, the pure fraction of the protein was loaded onto a G-25 column to obtain the protein in the formulation buffer (PBS). This preparation was used for immunological studies.

Example 47

Antigenic Characterization of PID3

The purified fraction of PID3 was characterized either by its recognition by different polyclonal sera and/or murine monoclonal antibodies, as well as by positive human sera to Dengue (table 56).

The highest recognitions in Dot blotting were obtained with the HMAF anti-DEN-4. The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against three human sera of high titers and three of low titers against DEN-4 was measured, achieving a substantial signal in both cases by Dot blotting and Western blotting.

TABLE 56

Reactivity of PID3 protein to monoclonal and polyclonal antibodies.

| Abs** | Specificity*** | PID3 |
|---|---|---|
| HMAF | DEN-1 | − |
| HMAF | DEN-2 | − |
| HMAF | DEN-3 | + |
| HMAF | DEN-4 | +++ |
| HMAF | EEE | − |
| HMAF | YFV | − |
| HMAF | SLV | − |
| Mab 3H5 | NT | − |

*A total of 10 μg of purified PID3 was applied. The intensity of the signal obtained was evaluated from + to ++.

**HMAF were used 1:100 while the Mab 3H5 was used in dilution 1:1000.

***EEE: Equine Encephalitis virus. YFV: Yellow Fever virus. SLV: Saint Louis Encephalitis virus. NT: Neutralizing specific-serotype.

Example 48

Characterization of the Antibody Response Generated by PID3

A total of 25 Balb/c mice were i.p immunized with 20 ug of purified PAZ3 in Freund adjuvant; 10 animals were bled after four doses and the antibodies anti-DEN were evaluated by ELISA. High antibody titers against DEN-4 were obtained while, no reactivity was obtained against the rest of the serotypes (table 57 and table 60). In addition, the HI assay was done and only positive titers were found against DEN-4 (table 58 and table 60). Finally, the in vitro neutralization assay was done and neutralization titers of 1:1280 against DEN-4 were obtained (table 59). No neutralization of the viral infection was found against the rest of the serotypes (table 60).

TABLE 57

Antibody titers against DEN-4 from the sera obtained upon immunization of mice with PID3.

| Mouse | Titers anti-DEN-4 (PID3) | Titers anti-DEN-4 PBS Control (—) |
|---|---|---|
| 1 | >1:128 000 | <1:100 |
| 2 | >1:128 000 | <1:100 |
| 3 | >1:128 000 | <1:100 |
| 4 | 1:64 000 | <1:100 |
| 5 | 1:64 000 | <1:100 |
| 6 | >1:128 000 | <1:100 |
| 7 | 1:128 000 | <1:100 |
| 8 | >1:128 000 | <1:100 |
| 9 | 1:128 000 | <1:100 |
| 10 | >1:128 000 | <1:100 |

TABLE 58

Titers by HI of the sera from the animals immunized with PID3.

| Mouse | Titers by HI* anti-DEN-4 PID3 | Titers by HI anti-DEN-4 PBS C (—) |
|---|---|---|
| 1 | >1:640 | <1:5 |
| 2 | 1:320 | <1:5 |
| 3 | >1:640 | <1:5 |
| 4 | >1:640 | <1:5 |
| 5 | <1:5 | <1:5 |
| 6 | >1:640 | <1:5 |
| 7 | 1:320 | <1:5 |
| 8 | >1:640 | <1:5 |
| 9 | 1:320 | <1:5 |
| 10 | >1:640 | <1:5 |

*The HI titers were defined as the highest dilution capable of inhibiting the hemagglutination of goose's erythrocytes against 8 hemagglutination viral units.

TABLE 59

Viral neutralization assay with the sera of animals immunized with PID3.

| Mouse | Neutralizing titers* anti-DEN-4 PID3 | Neutralizing titers anti-DEN-4 PBS C (—) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | 1:640 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 60

Cross-reactivity assay against all the viral serotypes by ELISA, HI and viral neutralization with the sera of animals immunized with PID3.

| Mixture of sera* | ELISA (anti-DEN-1) | ELISA (anti-DEN-2) | ELISA (anti-DEN-3) | ELISA (anti-DEN-4) |
|---|---|---|---|---|
| 1(PID3) | <1/100 | <1/100 | <1/100 | >1:128 000 |
| 2(PID3) | <1/100 | <1/100 | <1/100 | 1:128 000 |

| Mixture of sera* | HI** anti-DEN-1 | HI anti-DEN-2 | HI anti-DEN-3 | HI anti-DEN-4 |
|---|---|---|---|---|
| PID3 | <1/5 | <1/5 | <1/5 | >1/320 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1(PID3) | <1:5 | <1:5 | <1:5 | >1:1280 |
| 2(PID3) | <1:5 | <1:5 | <1:5 | >1/1280 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 49

Obtaining of pD4D2

The nucleotide sequence that codifies for the amino acids 286 to 426 of the E protein from the DEN-4 virus (Sequence No. 46) was amplified with the oligonucleotides identified in the sequencing list as Sequence No. 16 and Sequence No. 21 from the viral strain of DEN-4 (Zhao B., Mackow E. R., Buckler-White A. J., Markoff L., Chancock R. M., Lai C.-J., Makino Y. Cloning full-length Dengue type 4 viral DNA sequences: Analysis of genes coding for structural proteins. Virology 1986. 155:77-88).

The vector was created by digestion Xba /Xba I of the pLL3 plasmid, which contains the MDH gene plus a sequence of 6 histidines in the 3' region of the gene and the sequence of the E fragment from DEN-2 in the 3' end. As result, two regions of the E protein from serotypes 2 and 4 were obtained, fused to the same MDH gene. Upon ligation, the potential recombinants were analyzed by restriction enzyme digestion and positive clones were sequenced to check up the junctions. Competent cells MM294 were transformed with the selected clone, called pD4D2 (FIG. 13 and Sequence No. 53). Upon growing the colony in LB medium, a SDS-PAGE of the cellular lysate was done. As a result a 110 kDa band was obtained, which accounted for 20% of the total cellular proteins. The size of the protein obtained corresponded to the sum of the MDH protein and the two fragments of the DENe protein from Dengue virus. This protein was recognized by polyclonal antibodies anti-DEN-2 and anti-DEN-4 contained in the HMAF. This protein was denominated PD4D2 (Sequence No. 54).

Example 50

Purification of the PD4D2 Protein

The biomass obtained from the *E. coli* strain transformed with pD4D2 and grown at 37° C. was disrupted by French press. The recombinant protein was obtained either soluble or insoluble. From the pellet the protein was extracted with urea 6 M and the supernatant, containing the PD4D2 protein, was loaded onto a G-25 column to eliminate the chaotropic agent. The fraction obtained was then loaded onto the Chelating-sepharose FF column (Pharmacia, UK), in the presence of $Cu^{++}$ ions. A washing step was done with Imidazolee 30 mM and the protein was eluted with Imidazole 250 mM. Finally, the pure preparation was loaded onto a G-25 column to obtain the protein in the formulation buffer and use it for immunological studies.

Example 51

Antigenic Characterization of PD4D2

The purified fraction of PD4D2 was characterized either by its recognition by different polyclonal sera and/or murine monoclonal antibodies, as well as by positive human sera to Dengue (table 61).

The highest recognitions in Dot blotting were obtained with the HMAF anti-DEN-2 and anti-DEN-4. The recognition of the two other serotypes was less than for the case of serotypes 2 and 4. The antibodies generated by other flavivirus like the Yellow Fever virus and the Saint Louis Encephalitis virus had not any recognition at all. On the other hand, the Mab 3H5 had reactivity indeed, similar to that obtained for PLL2 and PLL3. Finally, the reactivity against human sera of high and low titers against DEN-2 and DEN-4 was measured, achieving a substantial signal for both cases by Western blotting and Dot blotting.

TABLE 61

Reactivity of PD4D2 protein against monoclonal and polyclonal antibodies.

| Abs** | Specificity*** | PD4D2 |
|---|---|---|
| HMAF | DEN-1 | – |
| HMAF | DEN-2 | +++ |
| HMAF | DEN-3 | – |
| HMAF | DEN-4 | +++ |
| HMAF | EEE | – |
| HMAF | YFV | – |
| HMAF | SLV | – |
| Mab 3H5 | NT | – |

*A total of 10 μg of purified PD4D2 was applied. The intensity of the signal obtained was evaluated from + to ++.

**HMAF were used 1:100 while the Mab 3H5 was used in dilution 1:1000.

***EEE: Equine Encephalitis virus. YFV: Yellow Fever virus. SLV: Saint Louis Encephalitis virus. NT: Neutralizing specific-serotype.

Example 52

Characterization of the Antibody Response Generated by PD4D2

A total of 25 Balb/c mice were i.p immunized with 20 ug of purified PD4D2 in Freund adjuvant; 10 animals were bled after four doses and the antibodies anti-DEN were evaluated by ELISA. High antibody titers against DEN-2 and DEN-4 were obtained while, no reactivity was obtained against the rest of the serotypes (table 62 and table 65). In addition, the hemagglutination inhibition assay (HI) was done and only positive titers were found against DEN-2 and DEN-4 (table 63 and table 65). Finally, the in vitro neutralization assay was done and neutralization titers of >1:1280 against DEN-2 and >1:1280 against DEN-4 were obtained (table 64). No neutralization of the viral infection was found against the rest of the serotypes (table 65).

TABLE 62

Antibody titers against DEN-2 and DEN-4 from the sera obtained upon immunization of mice with PD4D2.

| | Titers by ELISA (PD4D2) | | Titers by ELISA PBS C (—) | |
|---|---|---|---|---|
| Mouse | Anti-DEN-4 | Anti-DEN-2 | Anti-DEN-4 | Anti-DEN-2 |
| 1 | >1:128 000 | >1:128 000 | <1:100 | <1:100 |
| 2 | 1:128 000 | 1:128 000 | <1:100 | <1:100 |
| 3 | >1:128 000 | >1:128 000 | <1:100 | <1:100 |
| 4 | >1:128 000 | >1:128 000 | <1:100 | <1:100 |
| 5 | 1:64 000 | >1:128 000 | <1:100 | <1:100 |
| 6 | >1:128 000 | 1:128 000 | <1:100 | <1:100 |
| 7 | 1:64 000 | >1:128 000 | <1:100 | <1:100 |
| 8 | >1:128 000 | >1:128 000 | <1:100 | <1:100 |
| 9 | >1:128 000 | 1:128 000 | <1:100 | <1:100 |
| 10 | 1:128 000 | >1:128 000 | <1:100 | <1:100 |

TABLE 63

Titers by HI of the sera from the animals immunized with PD4D2.

| | Titers by HI (PD4D2) | | Titers by HI PBS C (—) | |
|---|---|---|---|---|
| Mouse | Anti-DEN-4 | Anti-DEN-2 | Anti-DEN-4 | Anti-DEN-2 |
| 1 | >1:640 | >1:640 | <1:5 | <1:5 |
| 2 | >1:640 | >1:640 | <1:5 | <1:5 |
| 3 | >1:640 | 1:320 | <1:5 | <1:5 |
| 4 | >1:640 | >1:640 | <1:5 | <1:5 |
| 5 | 1:320 | 1:640 | <1:5 | <1:5 |
| 6 | >1:640 | >1:640 | <1:5 | <1:5 |
| 7 | >1:640 | >1:640 | <1:5 | <1:5 |
| 8 | 1:320 | 1:320 | <1:5 | <1:5 |
| 9 | 1:320 | 1:320 | <1:5 | <1:5 |
| 10 | >1:640 | >1:640 | <1:5 | <1:5 |

*The HI titers were defined as the highest dilution capable of inhibiting the hemagglutination of goose's erythrocytes against 8 hemagglutination viral units.

TABLE 64

Viral neutralization assay with the sera of animals immunized with PD4D2.

| | Neutralizing titers* (PD4D2) | | Neutralizing titers PBS C (—) | |
|---|---|---|---|---|
| Mouse | Anti-DEN-4 | Anti-DEN-2 | Anti-DEN-4 | Anti-DEN-2 |
| 1 | >1:1280 | >1:1280 | <1:5 | <1:5 |
| 2 | >1:1280 | >1:1280 | <1:5 | <1:5 |
| 3 | 1:1280 | 1:1280 | <1:5 | <1:5 |
| 4 | >1:1280 | >1:1280 | <1:5 | <1:5 |
| 5 | 1:640 | 1:1280 | <1:5 | <1:5 |
| 6 | >1:1280 | >1:1280 | <1:5 | <1:5 |
| 7 | >1:1280 | >1:1280 | <1:5 | <1:5 |
| 8 | 1:640 | >1:1280 | <1:5 | <1:5 |
| 9 | >1:1280 | >1:1280 | <1:5 | <1:5 |
| 10 | >1:1280 | >1:1280 | <1:5 | <1:5 |

*The neutralizing titers were defined as the highest dilution of serum having 50% reduction of the number of viral plaques.

TABLE 65

Cross-reactivity assay against all the viral serotypes by ELISA, HI and viral neutralization with the sera of animals immunized with PD4D2.

| Mixture of sera* | ELISA (anti-DEN-1) | ELISA (anti-DEN-2) | ELISA (anti-DEN-3) | ELISA (anti-DEN-4) |
|---|---|---|---|---|
| 1(PD4D2) | <1/100 | >1:128 000 | <1/100 | 1:64 000 |
| 2(PD4D2) | <1/100 | >1:128 000 | <1/100 | >1:128 000 |

| Mixture of sera* | HI** anti-DEN-1 | HI anti-DEN-2 | HI anti-DEN-3 | HI anti-DEN-4 |
|---|---|---|---|---|
| PD4D2 | <1:5 | >1:320 | <1:5 | >1:320 |

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1(PD4D2) | <1:5 | >1:1280 | <1:5 | >1:1280 |
| 2(PD4D2) | <1:5 | >1:1280 | <1:5 | >1:1280 |

*Each mixture was formed by three sera.

**The HI titers were defined as the highest dilution capable of inhibiting the hemagglutination of goose's erythrocytes against 8 hemagglutination viral units.

***The neutralizing titers were defined as the highest dilution of serum having 50% reduction of the number of viral plaques.

Example 53

Protection Assay

For the evaluation of the protection conferred to mice immunized with all the assayed variants upon challenge with homologous lethal DEN, 15 mice of each group were used. Each animal received one dose of 100 $LD_{50}$ of lethal DEN by intracraneal inoculation and they were observed during 21 days to study the percentage of lethality. As positive controls, groups of 15 mice immunized with the four viral preparations (DEN-1, DEN-2, DEN-3 and DEN-4) were used. All the mice of these control groups survived while mice from the negative control group become sick between 7-11 days after challenge; therefore, achieving a 100% of mortality. Finally, groups immunized with the fusion proteins under study had between an 80% and 100% of protection and in all the cases, significant differences with respect to the control group were found (table 66).

TABLE 66

Percentage of survival in mice immunized with the protein variants assayed upon challenge with the homologous lethal Dengue virus.

| Immunogen | Percentage of survival* |
|---|---|
| PBS | 0 |
| DEN-1 | 100 |
| DEN-2 | 100 |
| DEN-3 | 100 |
| DEN-4 | 100 |
| PLL1 | 86 |
| PLL2 | 100 |
| PLL3 | 100 |
| PLH1 | 80 |
| PLH2 | 100 |
| PLH3 | 100 |
| PAZ1 | 80 |

TABLE 66-continued

| Percentage of survival in mice immunized with the protein variants assayed upon challenge with the homologous lethal Dengue virus. | |
|---|---|
| Immunogen | Percentage of survival* |
| PAZ2 | 100 |
| PAZ3 | 100 |
| PID1 | 86 |
| PID2 | 100 |
| PID3 | 100 |
| PD4D2 | 100 (DEN-4)<br>100 (DEN-2) |

*It was calculated: (# of mice survived)/(# total of mice). Data of survivors were taken 21 after challenge. In the case of mice immunized with pD4D2, 15 were challenged with DEN-4 and 15 with DEN-2.

Example 54

Lymphoproliferative Response

Animals from different groups immunized with the chimeric proteins containing the E fragment from DEN-2 (PLL1, PLL2 and PLL3), and a placebo group, were scarified 15 days after the last dose. Then, the spleen of the animals was harvested and the lymphoproliferative response against the four serotypes of Dengue virus was studied. Table 67 shows the results of the stimulation indexes obtained, which demonstrate that a serotype specific response was achieved.

TABLE 67

Stimulation indexes, against the four Dengue viral serotypes, of lymphocytes from mice immunized with PLL1, PLL2 and PLL3.

| | PLL1 | PLL2 | PLL3 | C (—) |
|---|---|---|---|---|
| DEN-1 | 1.3* | 1.0 | 0.8 | 1.2 |
| DEN-2 | 12.5 | 10.3 | 8.9 | 1.4 |
| DEN-3 | 1.0 | 1.6 | 1.8 | 1.4 |
| DEN-4 | 1.7 | 1.5 | 1.7 | 1.1 |
| Control Antigen | 1.1 | 1.0 | 1.3 | 0.9 |
| PHA** | 13.3 | 16.5 | 11.1 | 12.0 |

*Stimulation index: cocient of the counts per minute of the samples between the counts per minute of the control of the spontaneous synthesis of DNA.
**mitogen: Phytohemagglutinin.

The invention claimed is:

1. A chimeric protein PAZ3 comprising SEQ. ID. NO: 45.

2. A pharmaceutical preparation comprising a chimeric protein comprising SEQ ID NO: 45 and a pharmacological vehicle, wherein the preparation is capable of inducing a protective immune response against Dengue virus in a recipient.

3. A pharmaceutical preparation according to claim 2, wherein said preparation is a protective or therapeutic agent against the Dengue viruses, for oral, intramuscular, subcutaneous, mucosal or intravenous use.

4. A diagnostic composition comprising a PAZ3 protein comprising SEQ. ID. NO: 45 useful for the diagnosis and serotyping of the Dengue virus.

* * * * *